(12) United States Patent
Macdonald et al.

(10) Patent No.: US 8,821,944 B1
(45) Date of Patent: *Sep. 2, 2014

(54) POLYMORPH COMPOSITIONS, METHODS OF MAKING, AND USES THEREOF

(71) Applicant: Edge Therapeutics, Inc., Berkeley Heights, NJ (US)

(72) Inventors: R. Loch Macdonald, Toronto (CA); Cara R. Davis, Clanton, AL (US); Kevin Burton, Hoover, AL (US); Gary Winchester, Warrior, AL (US); Angela R. Stella, Pelham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/943,547

(22) Filed: Jul. 16, 2013

Related U.S. Application Data

(63) Continuation of application No. 13/800,480, filed on Mar. 13, 2013.

(51) Int. Cl.
| | | |
|---|---|---|
| *A61K 9/16* | (2006.01) | |
| *A61K 9/50* | (2006.01) | |
| *A61K 9/52* | (2006.01) | |
| *A61K 9/10* | (2006.01) | |
| *A61K 31/4422* | (2006.01) | |
| *A61K 9/14* | (2006.01) | |

(52) U.S. Cl.
CPC .................... *A61K 9/146* (2013.01); *A61K 31/4422* (2013.01)
USPC ............................ 424/501; 424/489; 514/356

(58) Field of Classification Search
USPC .................... 424/501, 489; 514/356
See application file for complete search history.

(56) References Cited

U.S. PATENT DOCUMENTS

| | | | |
|---|---|---|---|
| 3,932,645 A | 1/1976 | Meyer et al. | |
| 4,757,128 A | 7/1988 | Domb et al. | |
| 5,399,665 A | 3/1995 | Barrera et al. | |
| 5,407,609 A | 4/1995 | Tice et al. | |
| 5,491,154 A | 2/1996 | Ciceri et al. | |
| 5,599,824 A | 2/1997 | Grunenberg et al. | |
| 5,747,058 A | 5/1998 | Tipton et al. | |
| 5,968,542 A | 10/1999 | Tipton | |
| 5,977,163 A | 11/1999 | Li et al. | |
| 6,455,526 B1 * | 9/2002 | Kohn et al. ................ 514/248 |
| 2003/0012892 A1 * | 1/2003 | Lee et al. ................ 427/600 |
| 2007/0092574 A1 | 4/2007 | Cook | |
| 2007/0190154 A1 | 8/2007 | Zeigerson | |
| 2007/0207211 A1 | 9/2007 | Zeigerson | |
| 2008/0305147 A1 * | 12/2008 | Macdonald et al. ......... 424/423 |

(Continued)

OTHER PUBLICATIONS

Papgeorgiou et al. AAPS Journal vol. 8, No. 4, pp. E623-E631; publication year: 2006.*

(Continued)

*Primary Examiner* — Richard Schnizer
*Assistant Examiner* — Katherine Peebles
(74) *Attorney, Agent, or Firm* — Beverly W. Lubit

(57) ABSTRACT

The described invention provides a biodegradable, biocompatible delivery system of flowable sustained release microparticulate composition of a substantially pure crystalline form of a bioactive agent such as, for example, nimodipine, a process of preparing a therapeutic form of a substantially pure crystalline form of the bioactive agent and a method for treating an interruption of a cerebral artery in a subarachnoid space at risk of interruption caused by brain injury in a mammal, which reduces signs or symptoms of at least one delayed complication associated with brain injury.

21 Claims, 13 Drawing Sheets

(56) References Cited

U.S. PATENT DOCUMENTS

| | | |
|---|---|---|
| 2009/0162407 A1 | 6/2009 | Biggs et al. |
| 2010/0063179 A1 | 3/2010 | Atkinson et al. |
| 2010/0069602 A1 | 3/2010 | Raiche et al. |
| 2010/0189763 A1 | 7/2010 | Nettles |
| 2010/0215737 A1 | 8/2010 | Coulter |
| 2010/0216948 A1 | 8/2010 | Tipton |
| 2010/0239665 A1 | 9/2010 | Coulter |
| 2010/0291027 A1 | 11/2010 | Campbell |
| 2011/0204533 A1 | 8/2011 | Winchester et al. |
| 2011/0236497 A1 | 9/2011 | Tice et al. |
| 2013/0059008 A1 | 3/2013 | Atkinson et al. |

OTHER PUBLICATIONS

Coplin, W. M. et al., "Cerebrospinal fluid creatine kinase-BB isoenzyme activity and outcome after subarachnoid hemorrhage", Arch. Neurol., Nov. 1999, vol. 56, No. 11, pp. 1348-1352.

Langer, R., "New methods of drug delivery", Science, Sep. 28, 1990, vol. 248, No. 4976, pp. 1527-1533.

Sawhney, A.S. et al., "Bioerodible hydrogels based on photopolymerized poly(ethylene glycol)-co-poly(.alpha.- hydroxy acid) diacrylate macromers", Macromolecules, 1993, vol. 26, No. 4, pp. 581-587.

Grunenberg, A. et al., "Polymorphism in binary mixtures, as exemplified by nimodipine", International Journal of Pharmaceutics, (1995), 118: 11-21.

Grunenberg, A. et al., "Theoretical derivation and practical application of energy/temperature diagrams as an instrument in preformulation studies of polymorphic drug substances", International Journal of Pharmaceutics, (1996), 129: 147-158.

Docoslis, A. et al., "Characterization of the distribution, polymorphism, and stability of nimodipine in its solid dispersions in polyethylene glycol by micro-Raman spectroscopy and powder X-ray diffraction", The AAPS Journal, 2007, 9(3): Article 43.

Papageorgiou, G.Z. et al., "The effect of physical state on the drug dissolution rate: Miscibility studies of nimodipine with PVP", Journal of Thermal Analysis and Calorimetry, 2009, 95(3): 903-915.

Dreier, J.P. et al., "Cortical spreading ischemia is a novel process involved in ischaemic damage in patients with aneurysmal subarachnoid haemorrhage", Brain 132: 1866-81 (2009).

Degim, T. et al., "Controlled Delivery of Peptides and Proteins", Curr Pharm Des, 13(1), 99 (2007).

Kandel, E., Principles of Neural Sciences, 2d Ed., Eric R. Kandel and James H. Schwartz, Elsevier Science Publishing Co., Inc., New York, pp. 854-56 (1985).

Chusid, J., Correlative Neuroanatomy & Functional Neurology, 18th Ed., p. 50, 1982.

Mainardes, R. et al., "Drug Delivery Systems: Past, Present, and Future", Curr Drug Targets, 5(5), 449 (2004).

Malik, D. et al., "Recent Advances in Protein and Peptide Drug Delivery Systems", Curr Drug Deliv., 4(2), 141 (2007).

Nair, L. et al., "Polymers as Biomaterials for Tissue Engineering and Controlled Drug Delivery", Adv Biochem Engin/Biotechnol, 102, 47 (2006).

* cited by examiner

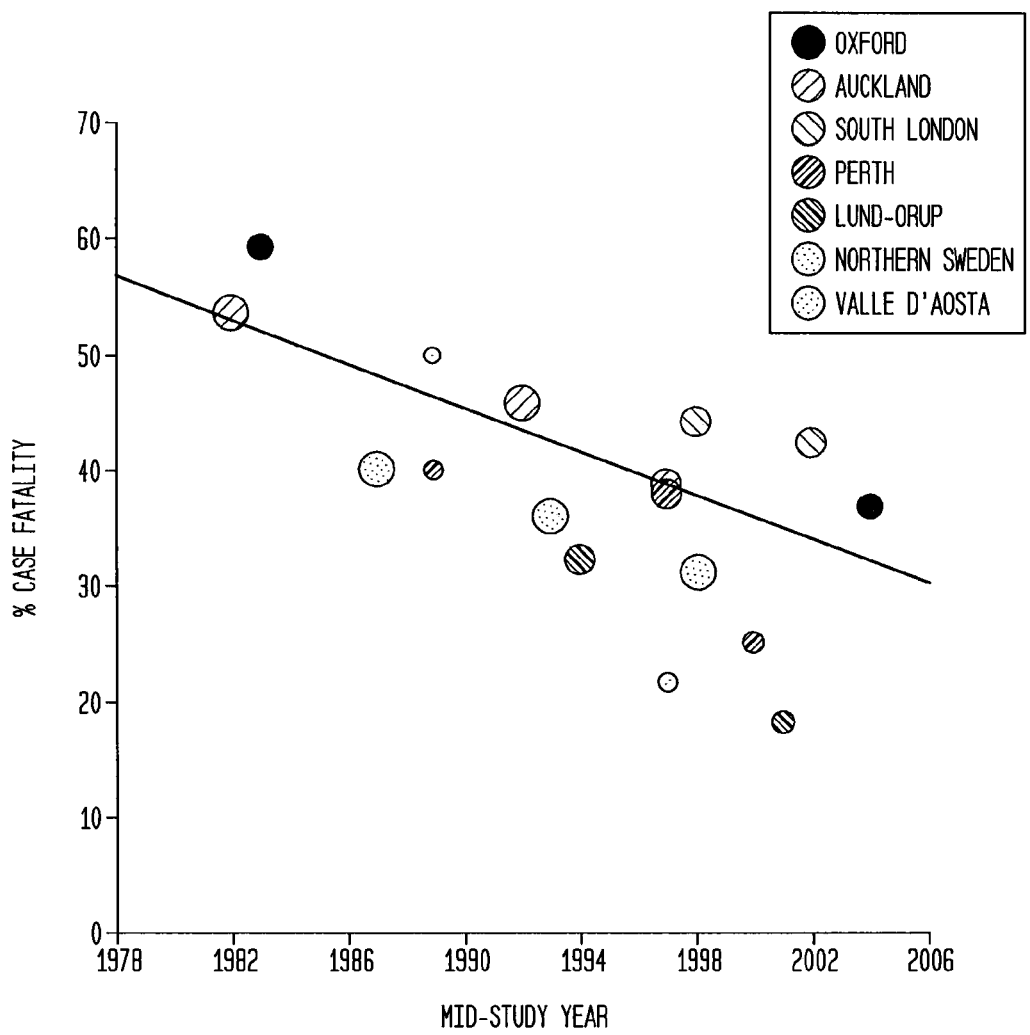

POLYMORPH COMPOSITIONS, METHODS OF MAKING, AND USES THEREOF

CROSS-REFERENCE TO RELATED APPLICATIONS

This application is a continuation of U.S. application Ser. No. 13/800,480 (filed Mar. 13, 2013), which claims the benefit of priority to U.S. Provisional Application 61/644,523 (filed May 9, 2012), the contents of which are incorporated by reference in its entirety.

FIELD OF THE INVENTION

The described invention relates to stable sustained release particulate formulations of active pharmaceutical ingredients.

BACKGROUND

The design and development of long-acting or sustained-release delivery formulations have been the focus of considerable efforts in the pharmaceutical industry for decades. Confounding these efforts is the formation of polymorphic drug forms.

Specifically, active pharmaceutical ingredients (APIs) are often administered to patients in their solid-states. Molecular solids or solid phases have been defined in thermodynamic terms as states of matter that are uniform in chemical composition and physical state. Molecular solids can exist in crystalline or noncrystalline (amorphous) phases depending on the extent of their three-dimensional order and relative thermodynamic stability. Crystalline states are characterized by a periodic array of molecules within a three-dimensional framework, termed a lattice, which are influenced by intra- and inter-molecular interactions. Crystalline forms may also include hydrates and/or solvates of the same compound.

A given crystalline form of a particular API often constitutes an important determinant of the API's ease of preparation, hygroscopicity, stability, solubility, shelf-life, ease of formulation, rate of dissolution in the gastrointestinal tract and other fluids, and in vivo bioavailability. Choice of a crystalline form will depend on a comparison of physical property variables of the different forms. In certain circumstances, one form may be preferred for ease of preparation and stability leading to longer shelf-lives. In other cases, an alternate form may be preferred for higher dissolution rate and/or better bioavailability.

Polymorphism refers to the ability of a molecule to exist in two or more crystalline forms in which the molecules within a crystal lattice may differ in structural arrangement (packing polymorphism) and/or in conformation (conformational polymorphism). A single enantiomer of a molecule may exhibit polymorphism. Polymorphic structures have the same chemical composition but different lattice structures and/or conformations resulting in different thermodynamic and kinetic properties. Thus, in the solid phase, polymorphic forms of an API exhibit different physical, chemical and pharmacological properties, such as in solubility, stability, melting point, density, bioavailability, X-ray diffraction patterns, molecular spectra, etc. However, in liquid or gaseous phases, polymorphic forms lose their structural organization and hence have identical properties. Phase transitions from one form to another may be reversible or irreversible. Polymorphic forms that are able to transform to another form without passing through a liquid or gaseous phase, are known as enantiotropic polymorphs, whereas those that are unable to interconvert under these conditions, are monotropic.

Enantiomers of chiral APIs may crystallize in three forms: (1) a racemate form in which the crystal lattice contains a regular arrangement of both enantiomers in equal amounts; (2) enantiopure forms in which the crystal lattice contains a regular arrangement of one enantiomer and not the other and vice versa; and (3) a conglomerate form in which there is a 1:1 physical mixture of two crystal lattices, one made up of a regular arrangement of one enantiomer and the other a regular arrangement of the other enantiomer.

Nimodipine [isopropyl(2-methoxyethyl)-1,4-dihydro-2,6-dimethyl-4-(3-nitrophenyl)-3,5-pyridinedicarboxylate] is a member of the dihydropyridine class of drugs belonging to the calcium channel antagonist family of pharmaceutical agents. Nimodipine is manufactured and marketed by Bayer AG as Nimotop™. Unsymmetrical esters of 1,4-dihydropyridine 3,5-dicarboxylic acids, processes and use as coronary and antihypertensive agents are disclosed in U.S. Pat. No. 3,799,934, incorporated herein by reference. Pharmaceutical compositions comprising nimodipine and an inert non-toxic carrier are disclosed for example in U.S. Pat. No. 3,932,645, incorporated herein by reference. When formulated as a flowable pharmaceutical composition for sustained release comprising a carrier comprising a plurality of microparticles, such that the nimodipine is dispersed throughout each micropoarticle, for surgical injection it is known as NimoGel™

Nimodipine can exist in amorphous or crystalline forms depending on treatment and storage conditions. Two distinct crystal forms of Nimodipine have been identified: Form I, which is the racemic crystal form with a lattice containing equal amounts of the two opposite enantiomers; and Form II, which is the conglomerate form, a 1:1 mixture of two crystal lattices, one containing one enantiomer and the other containing the opposite enantiomer (U.S. Pat. No. 5,599,824, incorporated herein by reference; Grunenberg, A. et al., "Polymorphism in binary mixtures, as exemplified by nimodipine", International Journal of Pharmaceutics, (1995), 118: 11-21; Grunenberg, A. et al., "Theoretical derivation and practical application of energy/temperature diagrams as an instrument in preformulation studies of polymorphic drug substances", International Journal of Pharmaceutics, (1996), 129: 147-158; Docoslis, A. et al., "Characterization of the distribution, polymorphism, and stability of nimodipine in its solid dispersions in polyethylene glycol by micro-Raman spectroscopy and powder X-ray diffraction", The AAPS Journal, 2007, 9(3): Article 43). Nimodipine Form I melts at +124° C. and Nimodipine Form II melts at +116° C. At +25° C. and +37° C., Form II has lower solubility but higher stability when compared to Form I. Form I can transform to Form II when stirred at room temperature to +80° C.

Nimodipine has been indicated for use in neurological conditions such as aneurysms, subarachnoid hemorrhage, neuropathic pain, arthritis, etc. It is currently used in the U.S. to treat subarachnoid hemorrhage and migraine. Due to low solubility, nimodipine is only administered as oral soft-gels, commercially sold as Nimotop™. Despite its high permeability, oral administration of nimodipine is associated with lower bioavailability due to slow dissolution in gastrointestinal fluids and/or cytochrome P450 digestion. Due to limited stability and bioavailability, patients need to be administered one or two 30 mg capsules of Nimotop™ up to six times a day, causing significant inconvenience to subarachnoid hemorrhage patients who are frequently fed through tubes because they are unable to swallow due to their neurological injury. In addition, as calcium channel antagonists, IV formulations of nimodipine cannot be used because of the high risk of inducing hypotension. Various controlled release and combinatorial formulations of nimodipine, for example, for immediate release (within 0-12 hours of administration) or slower release (within 12-24 hours) of administration are disclosed, for example, in US Patent Publication No. US 2010/0215737, US 2010/0239665, etc.

The commercial available nimodipine exists primarily as Form I. An orally administered immediate release formulation containing a co-precipitate of essentially amorphous nimodipine with poly-vinyl-pyrrolidone (PVP) is described in U.S. Pat. No. 5,491,154. A pharmaceutical preparation containing a suspension of a mixture of nimodipine Form II crystals in a suspension solution is described in U.S. Pat. No. 5,599,824. A solid dispersion of nimodipine Form II in PVP with fast release kinetics is described in Papageorgiou, G. Z. et al., "The effect of physical state on the drug dissolution rate: Miscibility studies of nimodipine with PVP", Journal of Thermal Analysis and calorimetry, 2009, 95(3): 903-915.

Thus the formation of different polymorphic drug forms in a microparticle can impact product performance and stability. What are needed are formulation strategies that can control to formation of drug polymorphs. These needs and other needs are satisfied by the delivery systems and methods of the present invention. Additionally, the present invention describes sustained release microparticle formulations of nimodipine polymorphs with delayed release kinetics and improved stability.

SUMMARY

According to one aspect disclosed herein are processes for producing a substantially pure polymorphic form of a bioactive agent encapsulated into microparticles, wherein the process comprises: (a) providing a substantially pure crystalline form of the bioactive agent; (b) adding the substantially pure crystalline form of the bioactive agent to a polymer solution, thereby creating a mixture of the bioactive agent and the polymer solution; (c) homogenizing the mixture to form a disperse phase; (d) mixing the disperse phase with a continuous phase comprising a continuous process medium, thereby forming an emulsion comprising the bioactive agent; (e) forming and extracting the microparticles comprising the substantially pure polymorphic form of the bioactive agent; and (f) drying the microparticles.

According to a further aspect, the polymer solutions of the aforementioned processes comprise a polymer and a solvent. It is understood and herein contemplated that the disclosed polymers comprise in one aspect polylactide, polylactide-co-glycolide, poly(orthoester), and poly(anhydride). In a further aspect, the polymer comprises 8515 DLG 6A, 8515 DLG 5A, 8515 DLG 4.5E, 88515 DLG 5E, 515 DLG 7A, 7525 DLG 7A, 7525 DLG 7E, 7525 DLG 5E, 6535DLG 5E, 6353 DLG 2E, 6535 DLG 4A, 5050DLG 4A, 5050 DLG2A, and 2000 MW DLPL. In another aspect, the solvent can comprise ethyl acetate or dichloromethane.

According to another aspect, the processes disclosed herein comprise drying the microparticle over a 4 to 48 hour period.

According to another aspect, disclosed herein are semi-solid, biodegradable, biocompatible delivery systems capable of sustained release kinetics comprising (i) a flowable microparticulate formulation comprising substantially pure crystalline form of a bioactive agent, and (ii) a pharmaceutically acceptable carrier, wherein the microparticulate formulation comprises a plurality of microparticles of uniform size distribution, wherein the bioactive agent is dispersed throughout each microparticle, and wherein the delivery system is further characterized in that the microparticulate formulation is capable of delayed release of the bioactive agent within a half life from 1 day to 30 days.

According to another aspect, disclosed herein are methods for treating at least one cerebral artery in a subarachnoid space at risk of interruption due to a brain injury in a human subject, comprising: (a) providing a flowable sustained release microparticle composition comprising: (i) a microparticulate formulation comprising a therapeutic amount of a substantially pure crystalline form I of nimodipine having an X-ray Powder Diffraction (XRPD) spectrum substantially the same as the X-ray Powder Diffraction (XRPD) spectrum shown in FIG. 11, wherein the microparticulate formulation comprises a plurality microparticles of uniform size distribution, wherein the therapeutic amount is effective to treat a delayed complication of the constriction of a cerebral artery, and (ii) a pharmaceutical carrier; and (b) administering the composition locally into a cerebral ventricle so that the microparticulate formation flows from the cerebrospinal fluid (CSF) in the cerebral ventricle into the cerebrospinal fluid (CSF) in the subarachnoid space before releasing the nimodipine form I in the subarachnoid space, wherein the nimodipine form I contacts and flows around the at least one cerebral artery in the subarachnoid space without entering systemic circulation in an amount to cause unwanted side effects.

According to another aspect, disclosed herein are methods for treating a cerebral vasospasm in a human subject, the method comprising: (a) providing a flowable sustained release microparticle composition comprising: (i) a microparticulate formulation comprising a therapeutic amount of a substantially pure crystalline form I of nimodipine having an X-ray Powder Diffraction (XRPD) spectrum substantially the same as the X-ray Powder Diffraction (XRPD) spectrum shown in FIG. 11, wherein the microparticulate formulation comprises a plurality microparticles of uniform size distribution, wherein the therapeutic amount is effective to treat a delayed complication of the constriction of a cerebral artery, and (ii) a pharmaceutical carrier; and b) administering the pharmaceutical composition to the human subject locally via surgical injection in a cistern closest to a cerebral artery at risk for vasospasm, such that the composition flows around the cerebral artery without entering the systemic circulation in an amount to cause unwanted side effects; wherein the pharmaceutical composition produces a localized pharmacologic effect; and wherein the therapeutic amount is effective to treat the cerebral vasospasm.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10 shows time trends in outcome of subarachnoid hemorrhage in seven population-based studies of subarachnoid hemorrhage (SAH), which shows 50% decrease in mortality over 20 years.

FIG. 12 shows differential scanning calorimetry (DSC) analysis of nimodipine prepared with different solvents and microencapsulated.

DETAILED DESCRIPTION

Glossary

Figure 1:
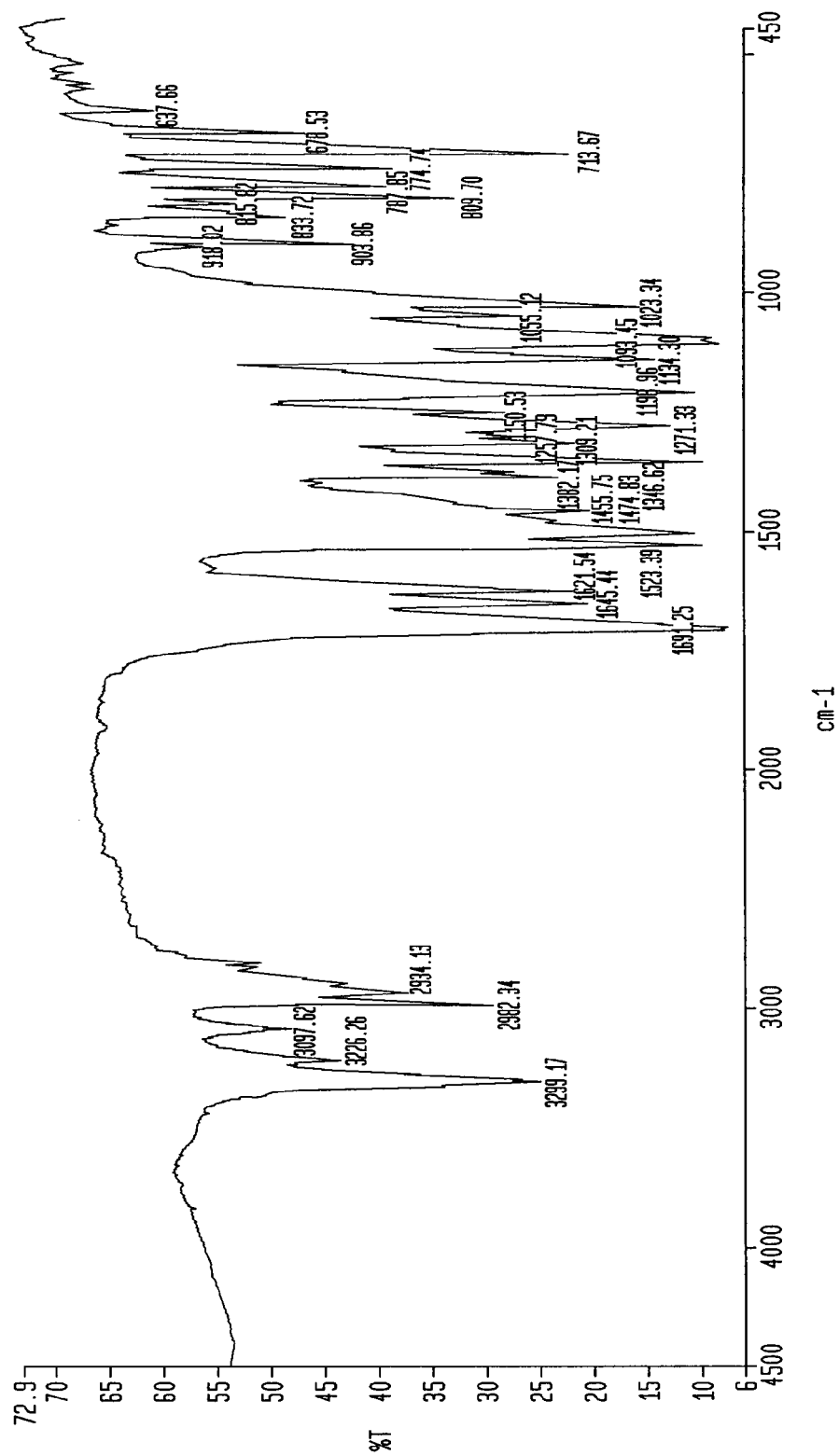
FIG. 1 shows an IR spectrum of nimodipine Form I as obtained using a sample of commercially available USP nimodipine Form I RS.

The term "active" as used herein refers to the ingredient, component or constituent of the compositions of the present invention responsible for the intended therapeutic effect. The term "active ingredient" ("AI", "active pharmaceutical ingredient", "API", or "bulk active") is the substance in a drug that is pharmaceutically active. As used herein, the phrase "additional active ingredient" refers to an agent, other than a compound of the described composition, that exerts a pharmacological, or any other beneficial activity.

As used herein, a "wt. %" or "weight percent" or "percent by weight" of a component, unless specifically stated to the contrary, refers to the ratio of the weight of the component to the total weight of the composition in which the component is included, expressed as a percentage.

The term "additive effect", as used herein, refers to a combined effect of two chemicals that is equal to the sum of the effect of each agent given alone.

"Admixture" or "blend" is generally used herein to refer to a physical combination of two or more different components. In the case of polymers, an admixture, or The term "administer" as used herein means to give or to apply.

The term "administering" as used herein includes in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired, or may be locally administered by means such as, but not limited to, injection, implantation, grafting, topical application, or parenterally.

The term "agent" is used herein to refer generally to compounds that are contained in or on the long-acting formulation. Agent may include an antibody or nucleic acid or an excipient or, more generally, any additive in the long-acting formulation. "Agent" includes a single such compound and is also intended to include a plurality of such compounds.

The term "agonist" as used herein refers to a chemical substance capable of activating a receptor to induce a pharmacological response. Receptors can be activated or inactivated by either endogenous or exogenous agonists and antagonists, resulting in stimulating or inhibiting a biological response. A physiological agonist is a substance that creates the same bodily responses, but does not bind to the same receptor. An endogenous agonist for a particular receptor is a compound naturally produced by the body which binds to and activates that receptor. A superagonist is a compound that is capable of producing a greater maximal response than the endogenous agonist for the target receptor, and thus an efficiency greater than 100%. This does not necessarily mean that it is more potent than the endogenous agonist, but is rather a comparison of the maximum possible response that can be produced inside a cell following receptor binding. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. An irreversible agonist is a type of agonist that binds permanently to a receptor in such a manner that the receptor is permanently activated. It is distinct from a mere agonist in that the association of an agonist to a receptor is reversible, whereas the binding of an irreversible agonist to a receptor is believed to be irreversible. This causes the compound to produce a brief burst of agonist activity, followed by desensitization and internalization of the receptor, which with long-term treatment produces an effect more like an antagonist. A selective agonist is specific for one certain type of receptor.

The terms "anastomosis" and "anastomoses" are used interchangeably to refer to interconnections between blood vessels. These interconnections protect the brain when part of its vascular supply is compromised. At the circle of Willis, the two anterior cerebral arteries are connected by the anterior communicating artery and the posterior cerebral arteries are connected to the internal carotid arteries by the posterior communicating arteries. Other important anastomoses include connections between the ophthalmic artery and branches of the external carotid artery through the orbit, and connections at the brain surface between branches of the middle, anterior, and posterior cerebral arteries (Principles of Neural Sciences, 2d Ed., Eric R. Kandel and James H. Schwartz, Elsevier Science Publishing Co., Inc., New York, pp. 854-56 (1985)).

The term "angiographic vasospasm" as used herein refers to the reduction of vessel size that can be detected on angiographic exams, including, but not limited to, computed tomographic, magnetic resonance or catheter angiography, occurring in approximately 67% of patients following subarachnoid hemorrhage. On the other hand, the term "clinical vasospasm" or "delayed cerebral ischemia" (DCI) as used herein refers to the syndrome of confusion and decreased level of consciousness associated with reduced blood flow to the brain parenchyma, occurring in approximately 30% of patients, and is now defined as DCI.

The term "antagonist" as used herein refers to a substance that interferes with the effects of another substance. Functional or physiological antagonism occurs when two substances produce opposite effects on the same physiological function. Chemical antagonism or inactivation is a reaction between two substances to neutralize their effects. Dispositional antagonism is the alteration of the disposition of a substance (its absorption, biotransformation, distribution, or excretion) so that less of the agent reaches the target or its persistence there is reduced. Antagonism at the receptor for a substance entails the blockade of the effect of an antagonist with an appropriate antagonist that competes for the same site.

The term "ataxia" as used herein refers to an inability to coordinate muscle activity during voluntary movement.

The term "bioactive agent" is used herein to include a compound of interest contained in or on a pharmaceutical formulation or dosage form that is used for pharmaceutical or medicinal purposes to provide some form of therapeutic effect or elicit some type of biologic response or activity. "Bioactive agent" includes a single such agent and is also intended to include a plurality of bioactive agents including, for example, combinations of two or more bioactive agents.

The term "biocompatible" as used herein refers to a material that is generally non-toxic to the recipient and does not possess any significant untoward effects to the subject and, further, that any metabolites or degradation products of the material are non-toxic to the subject. Typically a substance that is "biocompatible" causes no clinically relevant tissue irritation, injury, toxic reaction, or immunological reaction to living tissue.

The term "biodegradable" as used herein refers to a material that will erode to soluble species or that will degrade under physiologic conditions to smaller units or chemical species that are, themselves, non-toxic (biocompatible) to the subject and capable of being metabolized, eliminated, or excreted by the subject.

Figure 7:
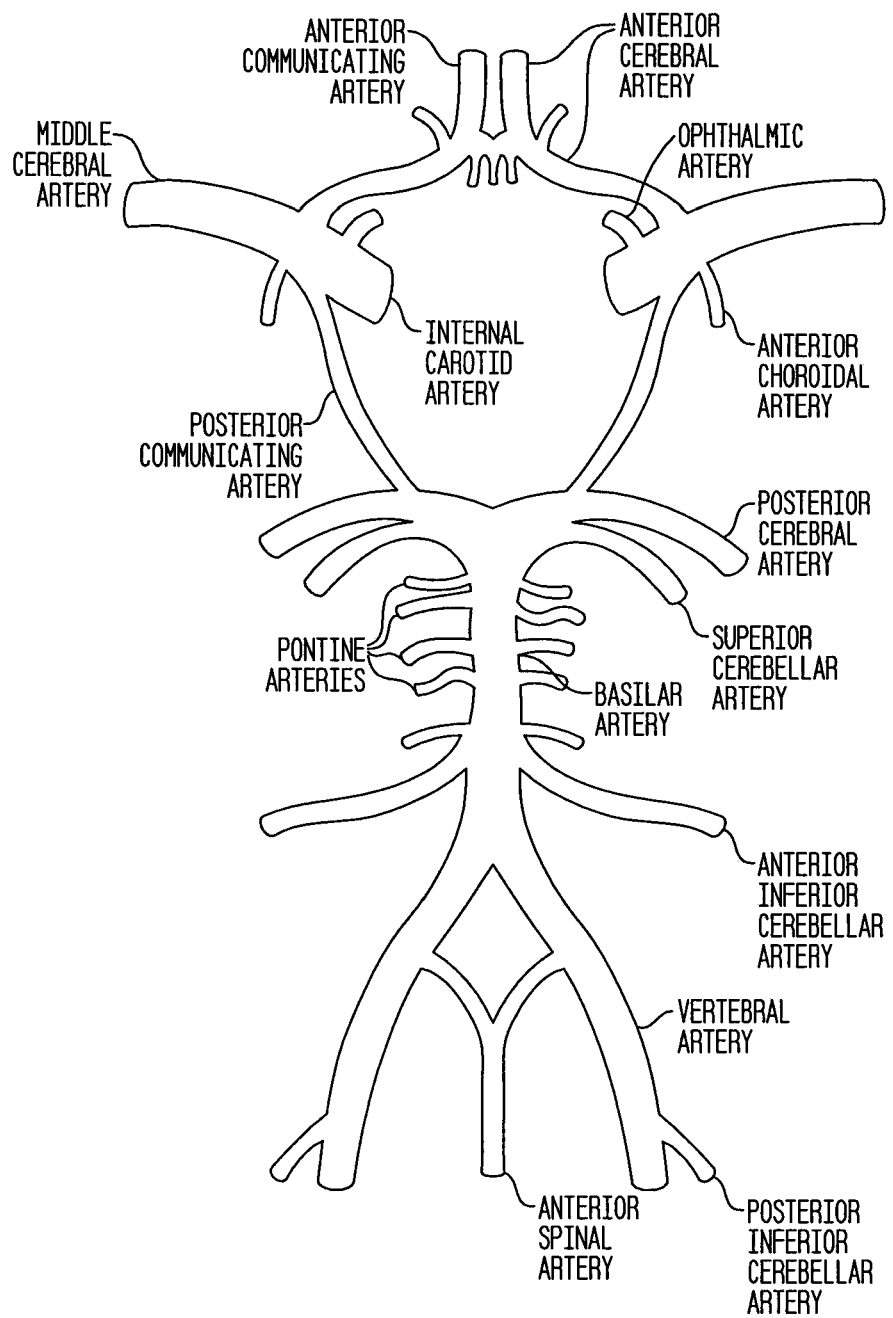
FIG. 7 shows an illustrative view of the cerebral arteries.
Figure 8:
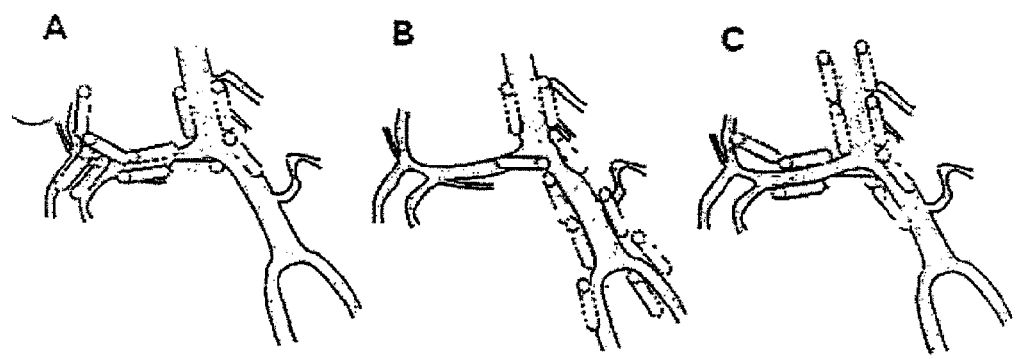
FIG. 8A shows an exemplary view of the application of a calcium channel antagonist, endothelin receptor antagonist, or putative transient receptor potential protein antagonist gel, slow-release solid or semisolid compound to the anterior communicating artery according to one embodiment of the present invention.
FIG. 8B shows a view of one embodiment of the application of a calcium channel antagonist, endothelin receptor antagonist, or putative transient receptor potential protein antagonist gel, slow-release solid or semisolid compound to the middle cerebral artery.
FIG. 8C shows a view of one embodiment of the application of a calcium channel antagonist, endothelin antagonist, or putative transient receptor potential protein antagonist gel, slow-release solid or semisolid compound to the internal carotid artery.
Figure 9A:
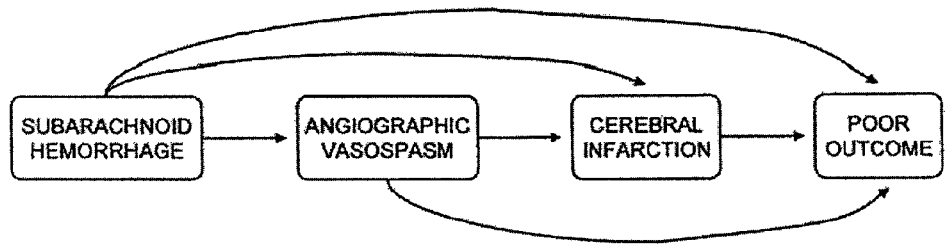
FIG. 9A shows a flow diagram for prognosis following subarachnoid hemorrhage.
Figure 9B:
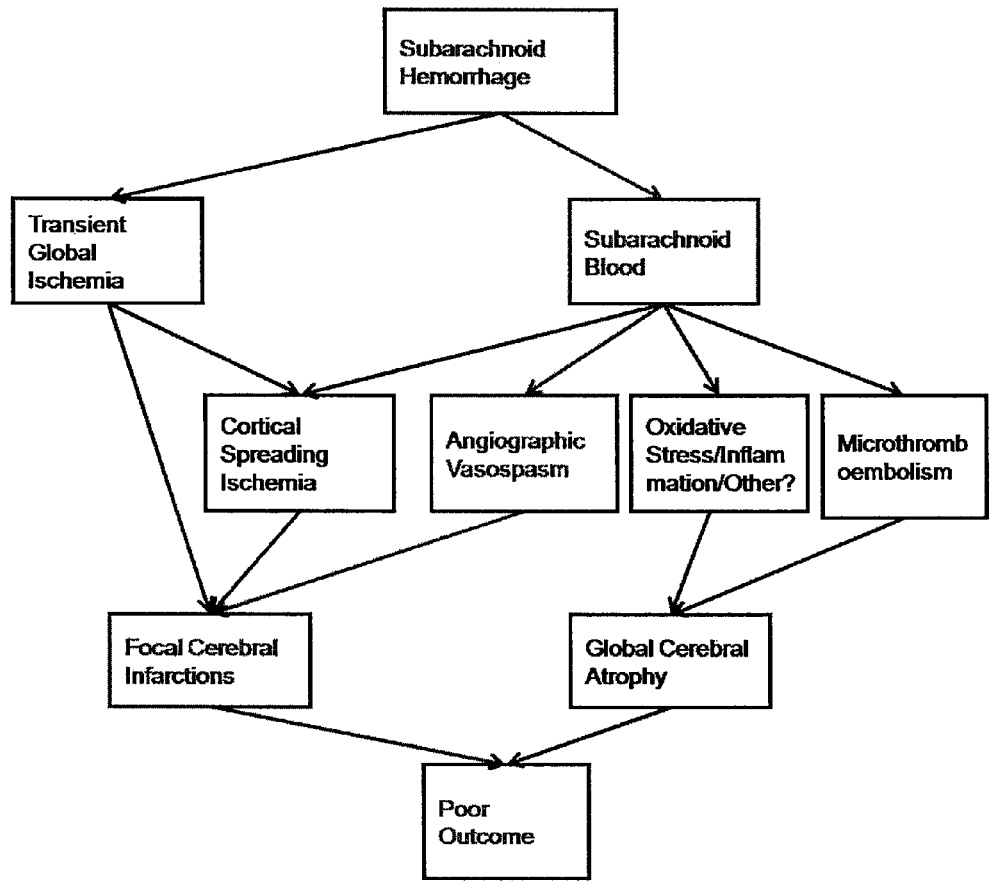
FIG. 9B shows a flow diagram of pathways proposed to be involved in delayed complications after subarachnoid hemorrhage.

The term "cerebral artery" or its numerous grammatical forms refers to the anterior communication artery, middle cerebral artery, internal carotid artery, anterior cerebral artery, ophthalmic artery, anterior choroidal artery, posterior communicating artery, basilar artery, and vertebral artery, among others. The Circle of Willis at the base of the brain is the principal arterial anastomotic trunk of the brain (See FIG. 7). Blood reaches it mainly via the vertebral and internal carotid arteries; anastomoses occur between arterial branches of the circle of Willis over the cerebral hemispheres and via extracranial arteries that penetrate the skull through various foramina. The circle of Willis is formed by anastomoses between the internal carotid, basilar, anterior cerebral, anterior communicating, posterior cerebral, and posterior communicating arteries. The internal carotid artery terminates in the anterior cerebral and middle cerebral arteries. Near its termination, the internal carotid artery gives rise to the posterior communicating artery, which joins caudally with the posterior cerebral artery. The anterior cerebral arteries connect via the anterior communicating artery.

The blood supply to the cerebral cortex mainly is via cortical branches of the anterior cerebral, middle cerebral, and posterior cerebral arteries, which reach the cortex in the pia mater. (Correlative Neuroanatomy & Functional Neurology, 18th Ed., p. 50, 1982).

The lateral surface of each cerebral hemisphere is supplied mainly by the middle cerebral artery. The medial and inferior surfaces of the cerebral hemispheres are supplied by the anterior cerebral and posterior cerebral arteries.

The middle cerebral artery, a terminal branch of the internal carotid artery, enters the lateral cerebral fissure and divides into cortical branches that supply the adjacent frontal, temporal, parietal and occipital lobes. Small penetrating arteries, the lenticulostriate arteries, arise from the basal portion of the middle cerebral artery to supply the internal capsule and adjacent structures.

The anterior cerebral artery extends medially from its origin from the internal carotid artery into the longitudinal cerebral fissure to the genu of the corupus callosum, where it turns posteriorly close to the corpus callosum. It gives branches to the medial frontal and parietal lobes and to the adjacent cortex along the medial surface of these lobes.

The posterior cerebral artery arises from the basilar artery at its rostral end usually at the level of the midbrain, curves dorsally around the cerebral peduncle, and sends branches to the medial and inferior surfaces of the temporal lobe and to the medial occipital lobe. Branches include the calcarine artery and perforating branches to the posterior thalamus and subthalamus.

The basilar artery is formed by the junction of the vertebral arteries. It supplies the upper brain stem via short paramedian, short cicumferential, and long circumferential branches.

Venous drainage from the brain chiefly is into the dural sinuses, vascular channels lying within the tough structure of the dura. The dural sinuses contain no valves and, for the most part, are triangular in shape. The superior longitudinal sinus is in the falx cerebri.

The term "cerebral vasospasm" as used herein refers to the delayed occurrence of narrowing of large capacitance arteries at the base of the brain after subarachnoid hemorrhage, often associated with diminished perfusion in the territory distal to the affected vessel. Cerebral vasospasm may occur any time after rupture of an aneurysm but most commonly peaks at seven days following the hemorrhage and often resolves within 14 days when the blood has been absorbed by the body.

The term "chiral" is used to describe asymmetric molecules that are nonsuperposable since they are mirror images of each other and therefore have the property of chirality. Such molecules are also called enantiomers and are characterized by optical activity.

The term "chirality" refers to the geometric property of a rigid object (or spatial arrangement of points or atoms) of being non-superposable on its mirror image; such an object has no symmetry elements of the second kind (a mirror plane, σ=S1, a center of inversion, i=S2, a rotation-reflection axis, S2n). If the object is superposable on its mirror image, the object is described as being achiral.

The term "chirality axis" refers to an axis about which a set of ligands is held so that it results in a spatial arrangement which is not superposable on its mirror image. For example, with an allene abC=C=Ccd the chiral axis is defined by the C=C=C bonds; and with an ortho-substituted biphenyl C-1, C-1', C-4 and C-4' lie on the chiral axis.

The term "chirality center" refers to an atom holding a set of ligands in a spatial arrangement, which is not superposable on its mirror image. A chirality center may be considered a generalized extension of the concept of the asymmetric carbon atom to central atoms of any element.

The terms "chiroptic" or "chiroptical" refer to the optical techniques (using refraction, absorption or emission of anisotropic radiation) for investigating chiral substances (for example, measurements of optical rotation at a fixed wavelength, optical rotary dispersion (ORD), circular dichroism (CD) and circular polarization of luminescence (CPL)).

The term "chirotopic" refers to an atom (or point, group, face, etc. in a molecular model) that resides within a chiral environment. One that resides within an achiral environment has been called achirotopic.

The term "cistern" or "cisterna" as used herein means a cavity or enclosed space serving as a reservoir.

The term "compounds of the present invention", unless indicated otherwise, refers to crystalline Form I and Form II of Nimodipine and the amorphous form of Nimodipine.

The term "complication" as used herein refers to a pathological process or event during a disorder that is not an essential part of the disease, although it may result from it or from independent causes. A delayed complication is one that occurs some time after a triggering effect. Complications associated with subarachnoid hemorrhage include, but are not limited to, angiographic vasospasm, microthromboemboli, and cortical spreading ischemia.

The term "condition", as used herein, refers to a variety of health states and is meant to include disorders or diseases caused by any underlying mechanism or disorder, or injury.

The term "contact" and all its grammatical forms as used herein refers to an instance of exposure by close physical contact of at least one substance to another substance.

The term "controlled release" is intended to refer to any drug-containing formulation in which the manner and profile of drug release from the formulation are regulated. This refers to immediate as well as non-immediate release formulations, with non-immediate release formulations including, but not limited to, sustained release and delayed release formulations.

The term "cortical spreading depolarization" or "CSD" as used herein refers to a wave of near-complete neuronal depolarization and neuronal swelling in the brain that is ignited when passive cation influx across the cellular membrane exceeds ATP-dependent sodium and calcium pump activity. The cation influx is followed by water influx and shrinkage of the extracellular space by about 70%. If normal ion homoeostasis is not restored through additional recruitment of sodium and calcium pump activity, the cell swelling is maintained—a process then termed "cytotoxic edema," since it potentially leads to cell death through a protracted intracellular calcium surge and mitochondrial depolarization. CSD induces dilation of resistance vessels in healthy tissue; hence regional cerebral blood flow increases during the neuronal depolarization phase. (Dreier, J. P. et al., Brain 132: 1866-81 (2009).

The term "cortical spreading ischemia" or "CSI," or "inverse hemodynamic response" refers to a severe microvascular spasm that is coupled to the neuronal depolarization phase. The resulting spreading perfusion deficit prolongs neuronal depolarization [as reflected by a prolonged negative shift of the extracellular direct current (DC) potential] and the intracellular sodium and calcium surge. The hypoperfusion is significant enough to produce a mismatch between neuronal energy demand and supply. (Id.).

As used herein, the term "crystalline form" or "crystal form" means that a certain material has definite shape and an orderly arrangement of structural units, which are arranged in fixed geometric patterns or lattices.

The term "delayed cerebral ischemia" or "DCI" as used herein refers to the occurrence of focal neurological impairment (such as hemiparesis, aphasia, apraxia, hemianopia, or neglect), or a decrease in the Glasgow coma scale (either on the total score or on one of its individual components [eye, motor on either side, verbal]). This may or may not last for at least one hour, is not apparent immediately after aneurysm occlusion and cannot be attributed to other causes by means of clinical assessment, CT or magnetic resonance imaging (MRI) scanning of the brain, and appropriate laboratory studies. Angiographic cerebral vasospasm is a description of a radiological test (either CT angiography [CTA], MR angiography [MRA] MRA or catheter angiography [CA]), and may be a cause of DCI.

The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

The term "diastereoisomerism" refers to stereoisomerism other than enantiomerism. Diastereoisomers (or diastereomers) are stereoisomers not related as mirror images. Diastereoisomers are characterized by differences in physical properties, and by some differences in chemical behavior towards achiral as well as chiral reagents. Diastereomers have similar chemical properties, since they are members of the same family. Their chemical properties are not identical, however. Diastereomers have different physical properties: different melting points, boiling points, solubilities in a given solvent, densities, refractive indexes, and so on. Diastereomers also differ in specific rotation; they may have the same or opposite signs of rotation, or some may be inactive. The presence of two chiral centers can lead to the existence of as many as four stereoisomers. For compounds containing three chiral centers, there could be as many as eight stereoisomers; for compounds containing four chiral centers, there could be as many as sixteen stereoisomers, and so on. The maximum number of stereoisomers that can exist is equal to 2n, where n is the number of chiral centers. The term "diastereotopic" refers to constitutionally equivalent atoms or groups of a molecule which are not symmetry related. Replacement of one of two diastereotopic atoms or groups results in the formation of one of a pair of diastereoisomers. For example, the two hydrogen atoms of the methylene group

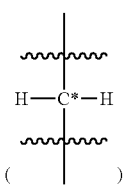

are diastereotopic.

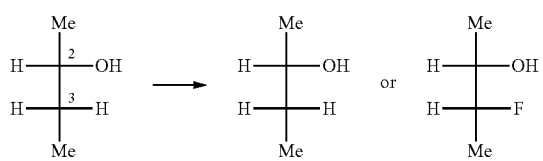

The term "disease" or "disorder", as used herein, refers to an impairment of health or a condition of abnormal functioning.

The term "dispersion", as used herein, refers to a two-phase system, in which one phase is distributed as droplets in the second, or continuous phase. In these systems, the dispersed phase frequently is referred to as the discontinuous or internal phase, and the continuous phase is called the external phase and comprises a continuous process medium. For example, in course dispersions, the particle size is 0.5 µm. In colloidal dispersions, size of the dispersed particle is in the range of approximately 1 nm to 0.5 µm. A molecular dispersion is a dispersion in which the dispersed phase consists of individual molecules; if the molecules are less than colloidal size, the result is a true solution.

The term "disposed", as used herein, refers to being placed, arranged or distributed in a particular fashion.

The term "drug" as used herein refers to a therapeutic agent or any substance, other than food, used in the prevention, diagnosis, alleviation, treatment, or cure of disease.

The term "effective amount" refers to the amount necessary or sufficient to realize a desired biologic effect.

The term "emulsion" as used herein refers to a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil.

The term "enantiomer" as used herein refers to one of a pair of optical isomers containing one or more asymmetric carbons (C*) whose molecular configurations have left- and right-hand (chiral) configurations. Enantiomers have identical physical properties, except as to the direction of rotation of the plane of polarized light. For example, glyceraldehyde and its mirror image have identical melting points, boiling points, densities, refractive indexes, and any other physical constant one might measure, expect that they are non-superimposable and one rotates the plane-polarized light to the right, while the other to the left by the same amount of rotation.

The term "essentially the same" with reference to X-ray diffraction peak positions means that typical peak position and intensity variability are taken into account. For example, one skilled in the art will appreciate that the peak positions (2Θ) will show some inter-apparatus variability, typically as much as 0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only.

The term "excipient" is used herein to include any other agent or compound that may be contained in a long-acting formulation that is not the bioactive agent. As such, an excipient should be pharmaceutically or biologically acceptable or relevant (for example, an excipient should generally be non-toxic to the subject). "Excipient" includes a single such compound and is also intended to include a plurality of such compounds.

The term "flowable", as used herein, refers to that which is capable of movement in, or as if in, a stream by continuous change of relative position.

The term "hydrogel" as used herein refers to a substance resulting in a solid, semisolid, pseudoplastic, or plastic structure containing a necessary aqueous component to produce a gelatinous or jelly-like mass.

The term "hypertension" as used herein refers to high systemic blood pressure; transitory or sustained elevation of systemic blood pressure to a level likely to induce cardiovascular damage or other adverse consequences.

The term "hypotension" as used herein refers to subnormal systemic arterial blood pressure; reduced pressure or tension of any kind The term "implanting" as used herein refers to grafting, embedding or inserting a substance, composition, or device into a pre-determined location within a tissue. The term "implant" as used herein is intended to refer generally to a controlled release preformed macroscopic device.

The term "impregnate", as used herein in its various grammatical forms refers to causing to be infused or permeated throughout; to fill interstices with a substance.

The phrase "in close proximity" as used herein refers to in the subarachnoid space within about 0.001 mm to about 10 mm, about 0.010 mm to about 10 mm, about 0.020 mm to about 10 mm, about 0.030 mm to about 10 mm, about 0.040 mm to about 10 mm, 0.050 mm to about 10 mm, about 0.060 mm to about 10 mm, about 0.070 mm to about 10 mm, about 0.080 mm to about 10 mm, about 0.090 mm to about 10 mm, about 0.1 mm to about 10 mm, about 0.2 mm to about 10 mm, about 0.3 mm to about 10 mm, about 0.4 mm to about 10 mm, about 0.5 mm to about 10 mm, about 0.6 mm to about 10 mm, about 0.7 mm to about 10 mm, about 0.8 mm to about 10 mm, about 0.9 mm to about 10 mm, about 1.0 mm to about 10 mm, about 1.1 mm to about 10 mm, about 1.2 mm to about 10 mm, about 1.3 mm to about 10 mm, about 1.4 mm to about 10 mm, about 1.5 mm to about 10 mm, about 1.6 mm to about 10 mm, about 1.7 mm to about 10 mm, about 1.8 mm to about 10 mm, about 1.9 mm to about 10 mm, about 2.0 mm to about 10 mm, about 2.1 mm to about 10 mm, about 2.2 mm to about 10 mm, about 2.3 mm to about 10 mm, about 2.4 mm to about 10 mm, about 2.5 mm to about 10 mm, about 2.6 mm to about 10 mm, about 2.7 mm to about 10 mm, about 2.8 mm to about 10 mm, about 2.9 mm to about 10 mm, about 3.0 mm to about 10 mm, about 3.1 mm to about 10 mm, about 3.2 mm to about 10 mm, about 3.3 mm to about 10 mm, about 3.4 mm to about 10 mm, about 3.5 mm to about 10 mm, about 3.6 mm to about 10 mm, about 3.7 mm to about 10 mm, about 3.8 mm to about 10 mm, about 3.9 mm to about 10 mm, about 4.0 mm to about 10 mm, about 4.1 mm to about 10 mm, about 4.2 mm to about 10 mm, about 4.3 mm to about 10 mm, about 4.4 mm to about 10 mm, about 4.5 mm to about 10 mm, about 4.6 mm to about 10 mm, about 4.7 mm to about 10 mm, about 4.8 mm to about 10 mm, about 4.9 mm to about 10 mm, about 5.0 mm to about 10 mm, about 5.1 mm to about 10 mm, about 5.2 mm to about 10 mm, about 5.3 mm to about 10 mm, about 5.4 mm to about 10 mm, about 5.5 mm to about 10 mm, about 5.6 mm to about 10 mm, about 5.7 mm to about 10 mm, about 5.8 mm to about 10 mm, about 5.9 mm to about 10 mm, about 6.0 mm to about 10 mm, about 6.1 mm to about 10 mm, about 6.2 mm to about 10 mm, about 6.3 mm to about 10 mm, about 6.4 mm to about 10 mm, about 6.5 mm to about 10 mm, about 6.6 mm to about 10 mm, about 6.7 mm to about 10 mm, about 6.8 mm to about 10 mm, about 6.9 mm to about 10 mm, about 7.0 mm to about 10 mm, about 7.1 mm to about 10 mm, about 7.2 mm to about 10 mm, about 7.3 mm to about 10 mm, about 7.4 mm to about 10 mm, about 7.5 mm to about 10 mm, about 7.6 mm to about 10 mm, about 7.7 mm to about 10 mm, about 7.8 mm to about 10 mm, about 7.9 mm to about 10 mm, about 8.0 mm to about 10 mm, about 8.1 mm to about 10 mm, about 8.2 mm to about 10 mm, about 8.3 mm to about 10 mm, about 8.4 mm to about 10 mm, about 8.5 mm to about 10 mm, about 8.6 mm to about 10 mm, about 8.7 mm to about 10 mm, about 8.8 mm to about 10 mm, about 8.9 mm to about 10 mm, about 9.0 mm to about 10 mm, about 9.1 mm to about 10 mm, about 9.2 mm to about 10 mm, about 9.3 mm to about 10 mm, about 9.4 mm to about 10 mm, about 9.5 mm to about 10 mm, about 9.6 mm to about 10 mm, about 9.7 mm to about 10 mm, about 9.8 mm to about 10 mm, or about 9.9 mm to about 10 mm of a site of brain injury or into a blood vessel in close proximity to the site of brain injury.

The terms "in the body", "void volume", "resection pocket", "excavation", "injection site", "deposition site" or "implant site" or "site of delivery" as used herein are meant to include all tissues of the body without limit, and may refer to spaces formed therein from injections, surgical incisions, tumor or tissue removal, tissue injuries, abscess formation, or any other similar cavity, space, or pocket formed thus by action of clinical assessment, treatment or physiologic response to disease or pathology as non-limiting examples thereof.

The term "injury," as used herein, refers to damage or harm to a structure or function of the body caused by an outside agent or force, which may be physical or chemical.

The term "isolated molecule" as used herein refers to a molecule that is substantially pure and is free of other substances with which it is ordinarily found in nature or in vivo systems to an extent practical and appropriate for its intended use.

The term "isomer" as used herein refers to one of two or more molecules having the same number and kind of atoms and hence the same molecular weight, but differing in chemical structure. Isomers may differ in the connectivities of the atoms (structural isomers), or they may have the same atomic connectivities but differ only in the arrangement or configuration of the atoms in space (stereoisomers). Stereoisomers may include, but are not limited to, L/Z double bond isomers, enantiomers, and diastereomers. Structural moieties that, when appropriately substituted, can impart stereoisomerism include, but are not limited to, olefinic, imine or oxime double bonds; tetrahedral carbon, sulfur, nitrogen or phosphorus atoms; and allenic groups. Enantiomers are non-superimposable mirror images. A mixture of equal parts of the optical forms of a compound is known as a racemic mixture or racemate. Diastereomers are stereoisomers that are not mirror images. The invention provides for each pure stereoisomer of any of the compounds described herein. Such stereoisomers may include enantiomers, diastereomers, or E or Z alkene, imine or oxime isomers. The invention also provides for stereoisomeric mixtures, including racemic mixtures, diastereomeric mixtures, or E/Z isomeric mixtures. Stereoisomers can be synthesized in pure form (Nogradi, M.; Stereoselective Synthesis, (1987) VCH Editor Ebel, H. and Asymmetric Synthesis, Volumes 3-5, (1983) Academic Press, Editor Morrison, J.) or they can be resolved by a variety of methods such as crystallization and chromatographic techniques (Jaques, J.; Collet, A.; Wilen, S.; Enantiomer, Racemates, and Resolutions, 1981, John Wiley and Sons and Asymmetric Synthesis, Vol. 2, 1983, Academic Press, Editor Morrison, J). In addition the compounds of the described invention may be present as enantiomers, diasteriomers, isomers or two or more of the compounds may be present to form a racemic or diastereomeric mixture.

The phrase "localized administration", as used herein, refers to administration of a therapeutic agent in a particular location in the body that may result in a localized pharmacologic effect or a diffuse pharmacologic effect. Local delivery of a bioactive agent to locations such as organs, cells or tissues can also result in a therapeutically useful, long-lasting presence of a bioactive agent in those local sites or tissues, since the routes by which a bioactive agent is distributed, metabolized, and eliminated from these locations may be different than the routes that define the pharmacokinetic duration of a bioactive agent delivered to the general systemic circulation. The present invention can deliver to any variety of sites, locations, organs, cells, or tissues throughout the body. In one aspect, the delivery is to locations that historically are limited in the volume of administered formulation, that is, only a small amount of formulation volume is capable of being administered. This aspect includes, but is not limited to, a local delivery, an interarticular delivery, such as between the joints, orthopedic sites (bones, bone defects, joints, and the like), CNS locations (including, for example, spinal, cerebrospinal or intrathecal delivery or delivery into the brain or to specific sites in and around the brain), intradermal, intratumor, peritumor, or ocular delivery (to sites adjacent to or on the eye, sites within ocular tissue, or intravitreal delivery inside the eye).

The phrase "localized pharmacologic effect", as used herein, refers to a pharmacologic effect limited to a certain location, i.e. in proximity to a certain location, place, area or site. The phrase "predominantly localized pharmacologic effect", as used herein, refers to a pharmacologic effect of a drug limited to a certain location by at least 1 to 3 orders of magnitude achieved with a localized administration as compared to a systemic administration.

The methods of the present invention includes the use of any type of long-acting formulation or dosage form that may be used for delivery of bioactive agent to prolong or extend a bioactive agent, such as a bioactive agent release, bioavailability, pharmacokinetics, pharmacodynamic effects or profiles.

The term "long-term" release, as used herein, refers to an implant constructed and arranged to deliver therapeutic levels of the active ingredient for at least 7 days, and potentially up to about 30 to about 60 days. Terms such as "long-acting", "sustained-release" or "controlled release" are used generally to describe a formulation, dosage form, device or other type of technologies used, such as, for example, in the art to achieve the prolonged or extended release or bioavailability of bioactive agent to a subject; it may refer to technologies that provide prolonged or extended release or bioavailability of a bioactive agent to the general systemic circulation or a subject or to local sites of action in a subject including (but not limited to) cells, tissues, organs, joints, regions, and the like. Furthermore, these terms may refer to a technology that is used to prolong or extend the release of a bioactive agent from a formulation or dosage form or they may refer to a technology used to extend or prolong the bioavailability or the pharmacokinetics or the duration of action of a bioactive agent to a subject or they may refer to a technology that is used to extend or prolong the pharmacodynamic effect elicited by a formulation. A "long-acting formulation," a "sustained release formulation," or a "controlled release formulation" (and the like) is a pharmaceutical formulation, dosage form, or other technology that is used to provide long-acting release of a bioactive agent to a subject.

Generally, long-acting or sustained release formulations comprise a bioactive agent or agents (including, for example, an antibody or nucleic acid, steroid, or nimodipine) that is/are incorporated or associated with a biocompatible polymer in one manner or another. The polymers typically used in the preparation of long-acting formulations include, but are not limited, to biodegradable polymers (such as the polyesters poly(lactide), poly(lactide-co-glycolide), poly(caprolactone), poly(hydroxybutyrates), and the like) and non-degradable polymers (such as ethylenevinyl acetate (EVA), silicone polymers, and the like). The agent may be blended homogeneously throughout the polymer or polymer matrix or the agent may be distributed unevenly (or discontinuously or heterogeneously) throughout the polymer or polymer matrix (as in the case of a bioactive agent-loaded core that is surrounded by a polymer-rich coating or polymer wall forming material as in the case of a microcapsule, nanocapsule, a coated or encapsulated implant, and the like). The dosage form may be in the physical form of particles, film, a fiber, a filament, a cylindrical implant, a asymmetrically-shaped implant, or a fibrous mesh (such as a woven or non-woven material; felt; gauze, sponge, and the like). When in the form of particles, the formulation may be in the form of microparticles, nanoparticles, microspheres, nanospheres, microcapsules or nanocapsules, and particles, in general, and combinations thereof. As such, the long-acting (or sustained-release) formulations of the present invention may include any variety of types or designs that are described, used or practiced in the art.

Long-acting formulations containing bioactive agents can be used to deliver those agents to the systemic circulation or they can be used to achieve local or site-specific delivery to cells, tissues, organs, bones and the like that are located nearby the site of administration. Further, formulations can be used to achieve systemic delivery of the bioactive agent and/or local delivery of the bioactive agent. Formulations can be delivered by injection (through, for example, needles, syringes, trocars, cannula, and the like) or by implantation. Delivery can be made via any variety of routes of administration commonly used for medical, clinical, surgical purposes including, but not limited to, intravenous, intraarterial, intramuscular, intraperitoneal, subcutaneous, intradermal, infusion and intracatheter delivery (and the like) in addition to delivery to specific locations (such as local delivery) including intrathecal, intracardiac, intraosseous (bone marrow), stereotactic-guided delivery, infusion delivery, CNS delivery, stereo-tactically administered delivery, orthopedic delivery (for example, delivery to joints, into bone, into bone defects and the like), cardiovascular delivery, inter- and intra- and para-ocular (including intravitreal and scleral and retrobulbar and sub-tenons delivery and the like), any delivery to any multitude of other sites, locations, organs, tissues, etc.

In one aspect, the methods of the present invention therefore envision utilizing any technology that is used (or may be envisioned to be used) in the field for parenteral routes of administration including, for example but without being limited to those described by: Maindares and Silva, Curr Drug Targets, 5(5), 449 (2004); or, Degim and Celebi, Curr Pharm Des, 13(1), 99 (2007); or, Encyclopedia of Pharmaceutical Technology, James Swarbrick and James Boylan (Editors), Marcel Dekker, New York (2004); or, Encyclopedia of Controlled Drug Delivery, Edith Mathiowitz (Editor); John Wiley & Sons, New York (1999); or Controlled Release Veterinary Drug Delivery, Robert Gurny and Michael J. Rathbone (Editors); Elsevier Science B.V., Amsterdam, The Netherlands (2000); or Encyclopedia of Nanoscience and Nanotechnology, James Schwarz, Cristian Contescu, Karol Putyera (Editors), Marcel Dekker, Inc., New York (2004); or Encyclopedia of Biomaterials and Biomedical Engineering, Gary Wnek and Gary Bowlin (Editors), Marcel Dekker, Inc., New York (2004); or, Malik, Baboota, Ahuja, and Hassan, Curr Drug Deliv., 4(2), 141 (2007); or Nair and Laurencin, Adv Biochem Eng Biotechnol, 102, 47 (2006); and the like. All of the above references are incorporated herein by this reference for all of their teachings as well as for the specific teachings of parenteral route technology methods.

In one aspect, the methods of the present invention include long-acting formulations that can be administered by needle, injection, infusion, implantation (as might be conducted either clinically or surgically), and the like.

The term "meninges" refers to three distinct connective tissue membranes that enclose and protect the brain and spinal cord; they are named (from outer to inner layer) the dura mater, the arachnoid, and the pia mater.

The dura mater is a dense fibrous structure that covers the brain and spinal cord. It has an inner meningeal and an outer periosteal or endosteal layer. The dural layers over the brain generally are fused, except where they separate to provide space for the venous sinuses and where the inner layer forms septa between brain portions. The outer layer attaches firmly to the inner surface of the cranial bones and sends vascular and fibrous extensions into the bone itself. Around the margin of the foramen magnum (the large opening in the base of the skull forming the passage from the cranial cavity to the spinal cavity) it is closely adherent to the bone, and is continuous with the spinal dura mater. The dura mater sends inward four processes that divide the cavity of the skull into a series of freely communicating compartments and further provides for the protection of the different parts of the brain. The processes of the cranial dura mater, which project into the cavity of the skull, are formed by reduplications of the inner (or meningeal) layer of the membrane. These processes include: (1) the falx cerebri, (2) the tentorium cerebelli, (3) the falx cerebelli, and (4) the diaphragma sellae.

The falx cerebri is a strong, arched process with a sickle-like form which descends vertically in the longitudinal fissure between the cerebral hemispheres. It is narrow in front, where it is attached to the ethmoid bone (the bone at the base of the cranium and the root of the nose) at the crista galli (the triangular midline process of the ethmoid bone); and broad behind, where it is connected with the upper surface of the tentorium cerebelli (an arched fold of dura mater that covers the upper surface of the cerebellum). Its upper margin is convex, and attached to the inner surface of the skull in the middle line, as far back as the internal occipital protuberance; it contains the superior sagittal sinus. Its lower margin is free and concave, and contains the inferior sagittal sinus.

The tentorium cerebelli is an arched lamina, elevated in the middle, and inclining downward toward the circumference. It covers the superior surface of the cerebellum, and supports the occipital lobes of the brain. Its anterior border is free and concave, and bounds a large oval opening (the incisura tentorii) for the transmission of the cerebral peduncles (the massive bundle of corticofugal nerve fibers passing longitudinally over the ventral surface of the midbrain on each side of the midline) as well as ascending sensory and autonomic fibers and other fiber tracts. The tentorium cerebelli is attached, behind, by its convex border, to the transverse ridges upon the inner surface of the occipital bone, and there encloses the transverse sinuses; and, in front, to the superior angle of the petrous part of the temporal bone on either side, enclosing the superior petrosal sinuses. At the apex of the petrous part of the temporal bone the free and attached borders meet, and, crossing one another, are continued forward to be fixed to the anterior and posterior clinoid processes respectively. The posterior border of the falx cerebri is attached to the middle line of its upper surface. The straight sinus is placed at the junction of the falx cerebri and the tentorium cerebelli.

The falx cerebelli is a small triangular process of dura mater that separates the two cerebellar hemispheres. Its base is attached, above, to the under and back part of the tentorium; and its posterior margin is attached to the lower division of the vertical crest on the inner surface of the occipital bone. As it descends, it sometimes divides into two smaller folds, which are lost on the sides of the foramen magnum.

The diaphragma sellae is a small circular horizontal fold, which roofs in the sella turcica (a saddlelike prominence on the upper surface of the sphenoid bone of the skull, situated in the middle cranial fossa and dividing it into two halves) and almost completely covers the pituitary gland (hypophysis); a central opening of variable size transmits the infundibulum (a funnel-shaped extension of the hypothalamus connecting the pituitary gland to the base of the brain).

The arteries of the dura mater are numerous. The meningeal branches of the anterior and posterior ethmoidal arteries and of the internal carotid artery, and a branch from the middle meningeal artery supply the dura of the anterior cranial fossa. The middle and accessory meningeal arteries of the internal maxillary artery; a branch from the ascending pharyngeal artery, which enters the skull through the foramen lacerum; branches from the internal carotid artery, and a recurrent branch from the lacrimal artery supply the dura of the middle cranial fossa. Meningeal branches from the occipital artery, one entering the skull through the jugular foramen, and another through the mastoid foramen; the posterior meningeal artery from the vertebral artery; occasional meningeal branches from the ascending pharyngeal artery, entering the skull through the jugular foramen and hypoglossal canal; and a branch from the middle meningeal artery supply the dura of the posterior cranial fossa.

The veins returning the blood from the cranial dura mater anastomose with the diploic veins or end in the various sinuses. Many of the meningeal veins do not open directly into the sinuses, but open indirectly through a series of ampullae, termed venous lacunae. These are found on either side of the superior sagittal sinus, especially near its middle portion, and are often invaginated by arachnoid granulations; they also exist near the transverse and straight sinuses. They communicate with the underlying cerebral veins, and also with the diploic and emissary veins.

The nerves of the cranial dura mater are filaments derived from the trigeminal, glossopharyngeal, vagal, second and third spinal, sphenopalatine, otic, and superior cervical ganglia and supply unmyelinated and myelinated sensory and autonomic fibers.

The middle meningeal layer, the arachnoid, is a delicate avascular membrane lying between the pia mater and the dura mater. It is separated from the overlying dura mater by the subdural space and from the underlying pia mater by the subarachnoid space, which contains cerebrospinal fluid.

The arachnoid consists of an outer cell layer of low cuboidal mesothelium. There is a space of variable thickness filled with cerebrospinal fluid and traversed by trabeculae and membranes consisting of collagen fibrils and cells resembling fibroblasts. The inner layer and the trabecula are covered by a somewhat low type of cuboidal mesothelium, which in places are flattened to a pavement type and blends on the inner deep layer with the cells of the pia mater. The arachnoid further contains a plexus of nerves derived from the motor root of the trigeminal, the facial, and the accessory cranial nerves.

The cranial part (arachnoidea encephali) of the arachnoid invests the brain loosely, and does not dip into the sulci (depressions or fissures in the surface of the brain) between the gyri (upraised folds or elevations in the surface of the brain), nor into the fissures, with the exception of the longitudinal fissure and several other larger sulci and fissures. On the upper surface of the brain, the arachnoid is thin and transparent; at the base it is thicker. It is slightly opaque toward the central part of the brain, where it extends across between the two temporal lobes in front of the pons so as to leave a considerable space between the pons and the brain.

The arachnoid surrounds the cranial and spinal nerves, and encloses them in loose sheaths as far as their points of exit from the skull.

The arachnoid villi are tufted prolongations of pia-arachnoid that protrude through the meningeal layer of the dura mater and have a thin limiting membrane. Tufted prolongations of pia-arachnoid composed of numerous arachnoid villi that penetrate dural venous sinuses and effect transfer of cerebrospinal fluid to the venous system are called arachnoid granulations.

An arachnoidal villus represents an invasion of the dura by the arachnoid membrane, whereby arachnoid mesothelial cells come to lie directly beneath the vascular endothelium of the great dural sinuses. Each villus consists of the following parts: (1) in the interior is a core of subarachnoid tissue, continuous with the meshwork of the general subarachnoid tissue through a narrow pedicle, by which the villus is attached to the arachnoid; (2) around this tissue is a layer of arachnoid membrane, limiting and enclosing the subarachnoid tissue; (3) outside this is the thinned wall of the lacuna, which is separated from the arachnoid by a potential space, which corresponds to and is continuous with the potential subdural space; and (4) if the villus projects into the sagittal sinus, it will be covered by the greatly thinned wall of the sinus, which may consist merely of endothelium. Fluid injected into the subarachnoid cavity will find its way into these villi. Such fluid passes from the villi into the venous sinuses into which they project.

The pia mater is a thin connective tissue membrane that is applied to the surface of the brain and spinal cord. It forms sheaths for the cranial nerves. Blood vessels supplying the brain travel through the pia into the brain. The pia mater is absent at the foramen of Majendie and the two foramina of Luschka and is perforated by all the blood vessels as they enter or leave the nervous system, and therefore is considered to be an incomplete membrane. In perivascular spaces, the pia apparently enters as a mesothelial lining of the outer surface of the space; a variable distance from the exterior, these cells become unrecognizable and are apparently lacking, replaced by neuroglia elements. The inner walls of the perivascular spaces likewise seem to be covered for a certain distance by the mesothelial cells, reflected with the vessels from the arachnoid covering of these vascular channels as they traverse the subarachnoid spaces.

The cranial pia mater (pia mater encephali; pia of the brain) invests the entire surface of the brain, dips between the cerebral gyri and cerebellar lamine, and is invaginated to form the tela chorioidea of the third ventricle, and the choroid plexuses of the lateral and third ventricles. As it passes over the roof of the fourth ventricle, it forms the tela chorioidea and the choroid plexuses of the fourth ventricle. On the cerebellum the membrane is more delicate; the vessels from its deep surface are shorter, and its relations to the cortex are not so intimate.

The term "microparticulate composition", as used herein, refers to a composition comprising a microparticulate formulation and a pharmaceutically acceptable carrier, where the microparticulate formulation comprises a therapeutic agent and a plurality of microparticles.

The terms "microencapsulated" and "encapsulated" are used herein to refer generally to a bioactive agent that is incorporated into any sort of long-acting formulation or technology regardless of shape or design; therefore, a "microencapsulated" or "encapsulated" bioactive agent may include bioactive agents that are incorporated into a particle or a microparticle and the like or it may include a bioactive agent that is incorporated into a solid implant and so on.

The term "modified bioactive agent" and the like is used herein to refer, generally, to a bioactive agent that has been modified with another entity through either covalent means or by non-covalent means. The term also is used to include prodrug forms of bioactive agents, where the prodrug form could be a polymeric prodrug or non-polymeric prodrug. Modifications conducted using polymers could be carried out with synthetic polymers (such as polyethylene glycol, PEG; polyvinylpyrrolidone, PVP; polyethylene oxide, PEO; propylene oxide, PPO; copolymers thereof; and the like) or biopolymers (such as polysaccharides, proteins, polypeptides, among others) or synthetic or modified biopolymers.

The term "modulate" as used herein means to regulate, alter, adapt, or adjust to a certain measure or proportion.

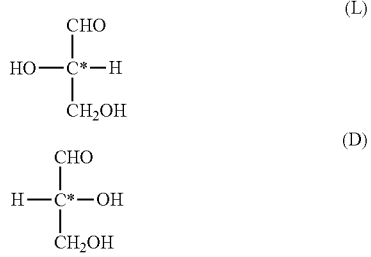

The term "optical rotation" refers to the change of direction of the plane of polarized light to either the right or the left as it passes through a molecule containing one or more asymmetric carbon atoms or chirality centers. The direction of rotation, if to the right, is indicated by either a plus sign (+) or a d−; if to the left, by a minus (−) or an l−. Molecules having a right-handed configuration (D) usually are dextrorotatory, D(+), but may be levorotatory, L(−). Molecules having left-handed configuration (L) are usually levorotatory, L(−), but may be dextrorotatory, D(+). Compounds with this property are said to be optically active and are termed optical isomers. The amount of rotation of the plane of polarized light varies with the molecule but is the same for any two isomers, though in opposite directions.

The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord or under the arachnoid membrane of the brain), intrasternal injection, or infusion techniques. A parenterally administered composition is delivered using a needle, e.g., a surgical needle.

The term "particles" as used herein refers to an extremely small constituent, e.g., nanoparticles or microparticles) that may contain in whole or in part at least one therapeutic agent as described herein. The term "microparticle" is used herein to refer generally to a variety of substantially structures having sizes from about 10 nm to 2000 microns (2 millimeters) and includes microcapsule, microsphere, nanoparticle, nanocapsule, nanosphere as well as particles, in general, that are less than about 2000 microns (2 millimeters). The particles may contain therapeutic agent(s) in a core surrounded by a coating. Therapeutic agent(s) also may be dispersed throughout the particles. Therapeutic agent(s) also may be adsorbed into the particles. The particles may be of any order release kinetics, including zero order release, first order release, second order release, delayed release, sustained release, immediate release, etc., and any combination thereof. The particle may include, in addition to therapeutic agent(s), any of those materials routinely used in the art of pharmacy and medicine, including, but not limited to, erodible, nonerodible, biodegradable, or nonbiodegradable material or combinations thereof. The particles may be microcapsules that contain the voltage-gated calcium channel antagonist in a solution or in a semi-solid state. The particles may be of virtually any shape.

The term "pharmaceutical composition" is used herein to refer to a composition that is employed to prevent, reduce in intensity, cure or otherwise treat a target condition or disease.

As used herein the phrase "pharmaceutically acceptable carrier" refers to any substantially non-toxic carrier useable for formulation and administration of the composition of the described invention in which the product of the described invention will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition. The term "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

The term "pharmacologic effect", as used herein, refers to a result or consequence of exposure to an active agent.

As used herein, the term "polymorph" refers to crystalline forms having the same chemical composition but different spatial arrangements of the molecules, atoms, and/or ions forming the crystal.

The term "racemate" as used herein refers to an equimolar mixture of two optically active components that neutralize the optical effect of each other and is therefore optically inactive.

The term "release" and its various grammatical forms, refers to dissolution of an active drug component and diffusion of the dissolved or solubilized species by a combination of the following processes: (1) hydration of a matrix, (2) diffusion of a solution into the matrix; (3) dissolution of the drug; and (4) diffusion of the dissolved drug out of the matrix.

The term "reduce" or "reducing" as used herein refers to a diminution, a decrease, an attenuation, limitation or abatement of the degree, intensity, extent, size, amount, density, number or occurrence of disorder in individuals at risk of developing the disorder.

The term "subarachnoid cavity" or "subarachnoid space" refers to the space between the outer cellular layer of the arachnoid and the pia mater, is occupied by tissue consisting of trabeculae of delicate connective tissue and intercommunicating channels in which the cerebrospinal fluid is contained. This cavity is small on the surface of the hemispheres of the brain; on the summit of each gyrus the pia mater and the arachnoid are in close contact; but triangular spaces are left in the sulci between the gyri, in which the subarachnoid trabecular tissue is found, because the pia mater dips into the sulci, whereas the arachnoid bridges across them from gyrus to gyrus. At certain parts of the base of the brain, the arachnoid is separated from the pia mater by wide intervals, which communicate freely with each other and are named subarachnoid cisternae; the subarachnoid tissue in these cisternae is less abundant.

The subarachnoid cisternae (cisternae subarachnoidales)" include the cisterna cerebellomedularis, the cisterna pontis, the cisterna interpeduncularis, cisterna chiasmatis, cisterna fossae cerebri lateralis and cisterna venae magnae cerebri.

The cisterna cerebellomedullaris (cisterna magna) is triangular on sagittal section, and results from the arachnoid bridging over the space between the medulla oblongata and the under surfaces of the hemispheres of the cerebellum; it is continuous with the subarachnoid cavity of the spinal cord at the level of the foramen magnum.

The cisterna pontis is a considerable space on the ventral aspect of the pons. It contains the basilar artery, and is continuous behind the ponswith the subarachnoid cavity of the spinal cord, and with the cisterna cerebellomedullaris; in front of the pons, it is continuous with the cisterna interpeduncularis.

The cisterna interpeduncularis (cisterna basalis) is a wide cavity where the arachnoid extends across between the two temporal lobes. It encloses the cerebral peduncles and the structures contained in the interpeduncular fossa, and contains the arterial circle of Willis. In front, the cisterna interpeduncularis extends forward across the optic chiasma, forming the cisterna chiasmatis, and on to the upper surface of the corpus callosum. The arachnoid stretches across from one cerebral hemisphere to the other immediately beneath the free border of the falx cerebri, and thus leaves a space in which the anterior cerebral arteries are contained. The cisterna fossae cerebri lateralis is formed in front of either temporal lobe by the arachnoid bridging across the lateral fissure. This cavity contains the middle cerebral artery. The cisterna venae magnae cerebri occupies the interval between the splenium of the corpus callosum and the superior surface of the cerebellum; it extends between the layers of the tela chorioidea of the third ventricle and contains the great cerebral vein.

The subarachnoid cavity communicates with the general ventricular cavity of the brain by three openings; one, the foramen of Majendie, is in the middle line at the inferior part of the roof of the fourth ventricle; the other two (the foramina of Luschka) are at the extremities of the lateral recesses of that ventricle, behind the upper roots of the glossopharyngeal nerves.

The term "subarachnoid hemorrhage" or "SAH" is used herein to refer to a condition in which blood collects beneath the arachnoid mater. This area, called the subarachnoid space, normally contains cerebrospinal fluid. The accumulation of blood in the subarachnoid space may lead to stroke, seizures, and other complications. Additionally, SAH may cause permanent brain damage and a number of harmful biochemical events in the brain. Causes of SAH include bleeding from a cerebral aneurysm, vascular anomaly, trauma and extension into the subarachnoid space from a primary intracerebral hemorrhage. Symptoms of SAH include, for example, sudden and severe headache, nausea and/or vomiting, symptoms of meningeal irritation (e.g., neck stiffness, low back pain, bilateral leg pain), photophobia and visual changes, and/or loss of consciousness. SAH is often secondary to a head injury or a blood vessel defect known as an aneurysm. In some instances, SAH can induce cerebral vasospasm that may in turn lead to an ischemic stroke. A common manifestation of a SAH is the presence of blood in the CSF. Subjects having a SAH may be identified by a number of symptoms. For example, a subject having an SAH will present with blood in the subarachnoid space. Subjects having an SAH can also be identified by an intracranial pressure that approximates mean arterial pressure at least during the actual hemorrhage from a ruptured aneurysm, by a fall in cerebral perfusion pressure, or by the sudden severe headache, sudden transient loss of consciousness (sometimes preceded by a painful headache), sudden loss of consciousness or sometimes sudden collapse and death. In about half of cases, subjects present with a severe headache which may be associated with physical exertion. Other symptoms associated with subarachnoid hemorrhage include nausea, vomiting, memory loss, hemiparesis and aphasia. Subjects having a SAH also may be identified by the presence of creatine kinase-BB isoenzyme activity in their CSF. This enzyme is enriched in the brain but normally is not present in the CSF. Thus, its presence in the CSF is indicative of "leak" from the brain into the subarachnoid space. Assay of creatinekinase BB isoenzyme activity in the CSF is described by Coplin et al. (Coplin et al 1999 Arch Neurol 56, 1348-1352) Additionally, a spinal tap or lumbar puncture may be used to demonstrate whether blood is present in the CSF, a strong indication of an SAH. A cranial CT scan or an MRI also may be used to identify blood in the subarachnoid region. Angiography also may be used to determine not only whether a hemorrhage has occurred, but also the location of the hemorrhage. Subarachnoid hemorrhage commonly results from rupture of an intracranial saccular aneurysm or from malformation of the arteriovenous system in the brain. Accordingly, a subject at risk of having an SAH includes a subject having a saccular aneurysm as well as a subject having a malformation of the arteriovenous system. Common sites of saccular aneurysms are the anterior communicating artery region, the origin of the posterior communicating artery from the internal carotid artery, the middle cerebral artery, the top of the basilar artery and the junction of the basilar artery with the superior cerebellar or the anterior inferior cerebellar artery. Subjects having SAH may be identified by an eye examination, whereby hemorrhage into the vitreous humor or slowed eye movement may indicate brain damage. A subject with a saccular aneurysm may be identified through routine medical imaging techniques, such as CT and MRI. A saccular or cerebral aneurysm forms a mushroom-like or berry-like shape (sometimes referred to as "a dome with a neck" shape).

The terms "subject" or "individual" or "patient" are used interchangeably to refer to a member of an animal species of mammalian origin, including humans.

The phrase "a subject having microthromboemboli" as used herein refers to a subject who presents with diagnostic markers associated with microthromboemboli. Diagnostic markers include, but are not limited to, the presence of blood in the CSF and/or a recent history of a SAH and/or development of neurological deterioration one to 14 days after SAH when the neurological deterioration is not due to another cause that can be diagnosed, including but not limited to seizures, hydrocephalus, increased intracranial pressure, infection, intracranial hemorrhage or other systemic factors. Another diagnostic marker may be embolic signals detected on transcranial Doppler ultrasound of large conducting cerebral arteries. Microthromboemboli-associated symptoms include, but are not limited to, paralysis on one side of the body, inability to vocalize the words or to understand spoken or written words, and inability to perform tasks requiring spatial analysis. Such symptoms may develop over a few days, or they may fluctuate in their appearance, or they may present abruptly.

The phrase "a subject having cortical spreading ischemia" as used herein means refers to a subject who presents with diagnostic markers associated with cortical spreading ischemia. Diagnostic markers include, but are not limited to, the presence of blood in the CSF and/or a recent history of a SAH and/or development of neurological deterioration one to 14 days after SAH when the neurological deterioration is not due to another cause that can be diagnosed, including but not limited to seizures, hydrocephalus, increased intracranial pressure, infection, intracranial hemorrhage or other systemic factors. Another diagnostic marker may be detection of propagating waves of depolarization with vasoconstriction detected by electrocorticography. Cortical spreading ischemia-associated symptoms include, but are not limited to, paralysis on one side of the body, inability to vocalize the words or to understand spoken or written words, and inability to perform tasks requiring spatial analysis. Such symptoms may develop over a few days, or they may fluctuate in their appearance, or they may present abruptly.

A subject at risk of DCI, microthromboemboli, cortical spreading ischemia, or angiographic vasospasm is one who has one or more predisposing factors to the development of these conditions. A predisposing factor includes, but is not limited to, existence of a SAH. A subject who has experienced a recent SAH is at significantly higher risk of developing angiographic vasospasm and DCI than a subject who has not had a recent SAH. MR angiography, CT angiography and catheter angiography can be used to diagnose at least one of DCI, microthromboemboli, cortical spreading ischemia or angiographic vasospasm. Angiography is a technique in which a contrast agent is introduced into the blood stream in order to view blood flow and/or arteries. A contrast agent is required because blood flow and/or arteries sometimes are only weakly apparent in a regular MR scan, CT scan or radiographic film for catheter angiography. Appropriate contrast agents will vary depending upon the imaging technique used. For example, gadolinium is commonly used as a contrast agent used in MR scans. Other MR appropriate contrast agents are known in the art.

As used herein, the term "substantially pure" with reference to a particular polymorphic form means that the polymorphic form includes less than 30%, less than 25%, less than 20%, less than 15%, less than 10%, less than 5%, less than 4%, less than 3%, less than 2%, less than 1% by weight of any other physical forms of the compound.

By "sufficient amount" and "sufficient time" means an amount and time needed to achieve the desired result or results, e.g., dissolve a portion of the polymer.

The term "surfactant" or "surface-active agent" as used herein refers to an agent, usually an organic chemical compound that is at least partially amphiphilic, i.e., typically containing a hydrophobic tail group and hydrophilic polar head group The term "surgical needle" as used herein, refers to any needle adapted for delivery of fluid (i.e., capable of flow) compositions into a selected anatomical structure. Injectable preparations, such as sterile injectable aqueous or oleaginous suspensions, may be formulated according to the known art using suitable dispersing or wetting agents and suspending agents.

The term "sustained release" (also referred to as "extended release") is used herein in its conventional sense to refer to a drug formulation that provides for gradual release of a drug over an extended period of time, and that preferably, although not necessarily, results in substantially constant blood levels of a drug over an extended time period. Alternatively, delayed absorption of a parenterally administered drug Form Is accomplished by dissolving or suspending the drug in an oil vehicle. Nonlimiting examples of sustained release biodegradable polymers include polyesters, polyester polyethylene glycol copolymers, polyamino-derived biopolymers, polyanhydrides, polyorthoesters, polyphosphazenes, SAIB, photopolymerizable biopolymers, protein polymers, collagen, polysaccharides, chitosans, and alginates The term "syndrome," as used herein, refers to a pattern of symptoms indicative of some disease or condition.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

The term "therapeutically effective amount", "effective amount", or an "amount effective" of one or more of the active agents is an amount that is sufficient to provide the intended benefit of treatment. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen may be planned which does not cause substantial toxicity and yet is effective to treat the particular subject. A therapeutically effective amount of the active agents that can be employed ranges from generally 0.1 mg/kg body weight and about 50 mg/kg body weight. The therapeutically effective amount for any particular application may vary depending on such factors as the disease or condition being treated, the particular calcium channel inhibitor, calcium channel antagonist, transient receptor potential protein antagonist, or endothelin antagonist being administered, the size of the subject, or the severity of the disease or condition. One of ordinary skill in the art may determine empirically the effective amount of a particular inhibitor and/or other therapeutic agent without necessitating undue experimentation. It is preferred generally that a maximum dose be used, that is, the highest safe dose according to some medical judgment. "Dose" and "dosage" are used interchangeably herein.

The term "therapeutic agent" as used herein refers to a drug, molecule, nucleic acid, protein, composition or other substance that provides a therapeutic effect. The terms "therapeutic agent" and "active agent" are used interchangeably.

The therapeutic agent(s), may be provided in particles. The term "particles" as used herein refers to nano or microparticles (or in some instances larger) that may contain in whole or in part the calcium channel inhibitor, calcium channel antagonist, or the other therapeutic agent(s) as described herein, including, but not limited to, endothelin antagonist and transient receptor potential protein antagonist. The particles may contain the therapeutic agent(s) in a core surrounded by a coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, etc., and any combination thereof. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules that contain the calcium channel antagonist in a solution or in a semi-solid state. The particles may be of virtually any shape.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50 which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

The term "topical" refers to administration of a composition to provide site-specific placement at, or immediately beneath, the point of application. The phrase "topically applying" describes application onto one or more surfaces(s) including epithelial surfaces. Topical administration, in contrast to transdermal administration, generally provides a local rather than a systemic effect.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The term "vasospasm" as used herein refers to a decrease in the internal diameter of a cerebral artery that results from contraction of smooth muscle within the wall of the artery which causes a decrease in blood flow, but generally without an increase in systemic vascular resistance. Vasospasm results in decreased cerebral blood flow and increased cerebral vascular resistance. Without being limited by theory, it generally is believed that vasospasm is caused by local injury to vessels, such as that which results from atherosclerosis and other structural injury including traumatic head injury, aneurismal SAH and other causes of SAH. Cerebral vasospasm is a naturally occurring vasoconstriction that also may be triggered by the presence of blood in the CSF, a common occurrence after rupture of an aneurysm or following traumatic head injury. Cerebral vasospasm ultimately can lead to brain cell damage, in the form of cerebral ischemia and infarction, due to interrupted blood supply. The term "cerebral vasospasm" as used herein refers to the delayed occurrence of narrowing of large capacitance arteries at the base of the brain after SAH, often associated with diminished perfusion in the territory distal to the affected vessel. Cerebral vasospasm may occur any time after rupture of an aneurysm but most commonly peaks at seven days following the hemorrhage and often resolves within 14 days when the blood has been absorbed by the body. Angiographic vasospasm is a consequence of SAH, but also can occur after any condition that deposits blood in the subarachnoid space. More specifically, the term "angiographic cerebral vasospasm" refers to the narrowing of the large capacitance arteries at the base of the brain (i.e., cerebral arteries) following hemorrhage into the subarachnoid space, and leads to reduced perfusion of distal brain regions.

Polymers and Excipients

Polymers used to prepare the long-acting formulation can be any biocompatible polymer. One of skill in the art would know how to select without undue experimentation the proper polymer composition to achieve the desired effect of, in one aspect, allowing the bioactive agent to provide its effect, and then, staging in the release of the bioactive agent from the long-acting formulation at an appropriate time about on or after the bioactive agent provides its effect, as described above. In one aspect the polymer is selected to delay the release of the bioactive agent until some time after the free agent has provided its effect, thereby extending the total effect period. Such selection of the polymer can include criteria, such as, for example, the type of polymer, the selection of a polymer or a co-polymer, the type of co-monomers used in the co-polymer, the ratio of the types of monomers used in the co-polymer, the molecular weight of the polymer, the size of the microparticle, and any other criteria that is used by one of skill in the art to control the release profile of a microparticle.

Without intending to be limiting, examples may include any biocompatible polymers used in the art. For example, biocompatible non-degradable polymers can be used including, for example, a polyacrylate; a polymer of ethylene-vinyl acetate, EVA; cellulose acetate; an acyl-substituted cellulose acetate; a non-degradable polyurethane; a polystyrene; a polyvinyl chloride; a polyvinyl fluoride; a poly(vinyl imidazole); a silicone-based polymer (for example, Silastic® and the like), a chlorosulphonate polyolefin; a polyethylene oxide; or a blend or copolymer thereof. Biocompatible biodegradable polymers can be used including, but not limited to, a poly(lactide); a poly(glycolide); a poly(lactide-co-glycolide); a poly(lactic acid); a poly(glycolic acid); a poly(lactic acid-co-glycolic acid); a poly(caprolactone); a poly(orthoester); a polyanhydride; a poly(phosphazene); a polyhydroxyalkanoate; a poly(hydroxybutyrate); a poly(hydroxybutyrate) synthetically derived; a poly(hydroxybutyrate) biologically derived; a polyester synthetically derived; a polyester biologically derived; a poly(lactide-co-caprolactone); a poly(lactide-co-glycolide-co-caprolactone); a polycarbonate; a tyrosine polycarbonate; a polyamide (including synthetic and natural polyamides, polypeptides, poly(amino acids) and the like); a polyesteramide; a polyester; a poly(dioxanone); a poly(alkylene alkylate); a polyether (such as polyethylene glycol, PEG, and polyethylene oxide, PEO); polyvinyl pyrrolidone or PVP; a polyurethane; a polyetherester; a polyacetal; a polycyanoacrylate; a poly(oxyethylene)/poly(oxypropylene) copolymer; a polyacetal, a polyketal; a polyphosphate; a (phosphorous-containing) polymer; a polyphosphoester; a polyhydroxyvalerate; a polyalkylene oxalate; a polyalkylene succinate; a poly(maleic acid); biopolymers or modified biopolymers including chitin, chitosan, modified chitosan, among other biocompatible polysaccharides; or biocompatible copolymers (including block copolymers or random copolymers) herein; or combinations or mixtures or admixtures of any polymers herein. Examples of copolymers that could be used include block copolymers containing blocks of hydrophilic or water-soluble polymers (such as polyethylene glycol, PEG, or polyvinyl pyrrolidone, PVP) with blocks of other biocompatible or biodegradable polymers (for example, poly(lactide) or poly(lactide-co-glycolide or polycaprolcatone or combinations thereof).

Furthermore, the present invention also relates to long-acting formulations prepared from copolymers that are comprised of the monomers of lactide (including L-lactide, D-lactide, and combinations thereof) or hydroxybutyrates or caprolactone or combinations thereof; and to long-acting formulations prepared from copolymers that are comprised of the monomers of DL-lactide, glycolide, hydroxybutyrate, and caprolactone and to long-acting formulations prepared from copolymers comprised of the monomers of DL-lactide or glycolide or caprolactone or hydroxybutyrates or combinations therein. Additionally, the present invention also relates to long-acting formulations prepared from admixtures containing the aforementioned copolymers (comprised of DL-lactide or glycolide or caprolactone or hydroxybutyrates or combinations therein) along with other biodegradable polymers including poly(DL-lactide-co-glycolide) or poly(DL-lactide) or PHA's, among others. The present invention can further include long-acting formulations prepared from block copolymers comprised with blocks of either hydrophobic or hydrophilic biocompatible polymers or biopolymers or biodegradable polymers such as polyethers (including polyethylene glycol, PEG; polyethylene oxide, PEO; polypropylene oxide, PPO and block copolymers comprised of combinations thereof) or polyvinyl pyrrolidone (PVP), polysaccharides, conjugated polysaccharides, modified polysaccharides, such as fatty acid conjugated polysaccharides, polylactides, polyesters, among others.

With the practice of the aspects herein, such as the combination of a delivery of the bioactive agent along with the delivery of a long-acting formulation of the bioactive agent, the polymer material (and in some aspects the excipient material) system mass is reduced due to bioactive agent needed in the long-acting formulation.

Composition

Generally, the disclosed controlled release systems such as the semisolid, biodegradable, biocompatibly delivery systems disclosed herein comprise a polymer or polymer matrix wherein the polymer matrix comprises a first polymer and a second polymer that is different from the first polymer; and bioactive agent encapsulated in the polymer or polymer matrix. The term "polymer matrix" as used herein is intended to refer a portion (or all) of the controlled release system which comprises the polymer mixture. The polymer matrix does not necessarily, but can, comprise cross-linked or intertwined polymer chains. In one aspect, the polymer matrix is a polymer composition, wherein the polymer composition encapsulates the bioactive agent. In a further aspect, portions of the polymer matrix can comprise only one of the first and second polymer. Thus, the controlled release system polymer matrix need not be homogenous, although in another aspect the polymer matrix can be homogenous.

The first and second polymer of the polymer matrix can be present in the controlled release system in any desired ratio, which is the weight ratio of the first polymer to the second polymer. In one aspect, the ratio of the first polymer to the second polymer is from about 90:10 to about 40:60, including ratios without limitation of about 85:15, 80:20, 70:30, 75:25, 65:35, and 50:50, among others. In addition, more than two polymers can be present in a blend, for example, 3, 4, 5, or more polymers can be present.

In one aspect, the first and second polymers have at least one different property. Depending on the desired degradation profile of the controlled release system, a wide variety of properties can be different among the polymers, including without limitation, chemical composition, viscosity (e.g., intrinsic viscosity), molecular weight, thermal properties, such as glass transition temperature ($T_g$), the chemical composition of a non-repeating unit therein, such as an end group, degradation rate, hydrophilicity, porosity, density, or a combination thereof. In one aspect, the first polymer and the second polymer have different degradation rates in an aqueous medium. In one aspect, a degradation profile of a controlled release system is selected, and a combination of polymers having properties that, when combined, are believed to achieve the selected degradation profile are used to make the controlled release system.

In one aspect, the polymer and first polymer and the second polymer of the polymer matrix have one or more different non-repeating units, such as, for example, an end group, or a non-repeating unit in the backbone of the polymer. In a further aspect, the first polymer and the second polymer of the polymer matrix have one or more different end groups. For example, the first polymer can have a more polar end group than one or more end group(s) of the second polymer. Thus, in this aspect, the first polymer will typically be more hydrophilic and thus lead to faster water uptake, relative to a controlled release system comprising the second polymer (with the less polar end group) alone. In a specific aspect, the first polymer can have one or more carboxylic acid end groups, and the second polymer can have one or more ester end groups. In another aspect a single polymer can have one or more ester or carboxylic end groups depending on the desire for faster water uptake or a more controlled release system.

In another aspect, the first polymer and the second polymer of the polymer matrix have different molecular weights. In one aspect, the first polymer has a molecular weight that is at least about 3000 Daltons greater than the molecular weight of the second polymer. The molecular weight can have any suitable value, which can, in various aspects, depend on the desired properties of the controlled release system. If, for example, a controlled release system having high mechanical strength is desired, at least one of the polymers can have a high molecular weight. In this example, if it is also desired that the controlled release system have short term release capability (e.g., less than about 2 weeks), then a lower molecular weight polymer can be combined with the high molecular weight polymer. In this aspect, the high molecular weight polymer will typically provide good structural integrity for the controlled release system, while the lower molecular weight polymer can provide short term release capability.

Non-limiting examples of polymers for use as part of a controlled release delivery system or in a polymer matrix for use in a controlled release delivery system include polyesters, polyhydroxyalkanoates, polyhydroxybutyrates, polydioxanones, polyhydroxyvalerates, polyanhydrides, polyorthoesters, polyphosphazenes, polyphosphates, polyphosphoesters, polydioxanones, polyphosphoesters, polyphosphates, polyphosphonates, polyphosphates, polyhydroxyalkanoates, polycarbonates, polyalkylcarbonates, polyorthocarbonates, polyesteramides, polyamides, polyamines, polypeptides, polyurethanes, polyalkylene alkylates, polyalkylene oxalates, polyalkylene succinates, polyhydroxy fatty acids, polyacetals, polycyanoacrylates, polyketals, polyetheresters, polyethers, polyalkylene glycols, polyalkylene oxides, polyethylene glycols, polyethylene oxides, polypeptides, polysaccharides, or polyvinyl pyrrolidones. Other non-biodegradable but durable polymers include without limitation ethylene-vinyl acetate co-polymer, polytetrafluoroethylene, polypropylene, polyethylene, and the like. Likewise, other suitable non-biodegradable polymers include without limitation silicones and polyurethanes.

In a further aspect, the polymer can be a poly(lactide), a poly(glycolide), a poly(lactide-co-glycolide), a poly(caprolactone), a poly(orthoester), a poly(phosphazene), a poly(hydroxybutyrate) or a copolymer containing a poly(hydroxybutarate), a poly(lactide-co-caprolactone), a polycarbonate, a polyesteramide, a polyanhydride, a poly(dioxanone), a poly (alkylene alkylate), a copolymer of polyethylene glycol and a polyorthoester, a biodegradable polyurethane, a poly(amino acid), a polyamide, a polyesteramide, a polyetherester, a polyacetal, a polycyanoacrylate, a poly(oxyethylene)/poly (oxypropylene) copolymer, polyacetals, polyketals, polyphosphoesters, polyhydroxyvalerates or a copolymer containing a polyhydroxyvalerate, polyalkylene oxalates, polyalkylene succinates, poly(maleic acid), and copolymers, terpolymers, combinations, or blends thereof.

In a still further aspect, useful biocompatible polymers are those that comprise one or more residues of lactic acid, glycolic acid, lactide, glycolide, caprolactone, hydroxybutyrate, hydroxyvalerates, dioxanones, polyethylene glycol (PEG), polyethylene oxide, or a combination thereof. In a still further aspect, useful biocompatible polymers are those that comprise one or more residues of lactide, glycolide, caprolactone, or a combination thereof.

In one aspect, useful biodegradable polymers are those that comprise one or more blocks of hydrophilic or water soluble polymers, including, but not limited to, polyethylene glycol, (PEG), or polyvinyl pyrrolidone (PVP), in combination with one or more blocks another biocompabible or biodegradable polymer that comprises lactide, glycolide, caprolactone, or a combination thereof.

In specific aspects, the biodegradable polymer can comprise one or more lactide residues. To that end, the polymer can comprise any lactide residue, including all racemic and stereospecific forms of lactide, including, but not limited to, L-lactide, D-lactide, and D,L-lactide, or a mixture thereof. Useful polymers comprising lactide include, but are not limited to poly(L-lactide), poly(D-lactide), and poly(DL-lactide); and poly(lactide-co-glycolide), including poly(L-lactide-co-glycolide), poly(D-lactide-co-glycolide), and poly (DL-lactide-co-glycolide); or copolymers, terpolymers, combinations, or blends thereof. Lactide/glycolide polymers can be conveniently made by melt polymerization through ring opening of lactide and glycolide monomers. Additionally, racemic DL-lactide, L-lactide, and D-lactide polymers are commercially available. The L-polymers are more crystalline and resorb slower than DL-polymers. In addition to copolymers comprising glycolide and DL-lactide or L-lactide, copolymers of L-lactide and DL-lactide are commercially available. Homopolymers of lactide or glycolide are also commercially available.

When the biodegradable polymer is poly(lactide-co-glycolide), poly(lactide), or poly(glycolide), the amount of lactide and glycolide in the polymer can vary. In a further aspect, the biodegradable polymer contains 0 to 100 mole %, 40 to 100 mole %, 50 to 100 mole %, 60 to 100 mole %, 70 to 100 mole %, or 80 to 100 mole % lactide and from 0 to 100 mole %, 0 to 60 mole %, 10 to 40 mole %, 20 to 40 mole %, or 30 to 40 mole % glycolide, wherein the amount of lactide and glycolide is 100 mole %. In a further aspect, the biodegradable polymer can be poly(lactide), 95:5 poly(lactide-co-glycolide) 85:15 poly(lactide-co-glycolide), 75:25 poly(lactide-co-glycolide), 65:35 poly(lactide-co-glycolide), or 50:50 poly(lactide-co-glycolide), where the ratios are mole ratios.

In a specific aspect, the first and second polymers are both poly(lactide-co-glycolide) polymers. In a further specific aspect, the ratio of lactide to glycolide is from about 90:10 to about 40:60. In still a further specific aspect, the ratio of lactide to glycolide is from about 85:15 to about 50:50.

In a further aspect, the polymer or first and second polymers of the polymer matrix can be a poly(caprolactone) or a poly(lactide-co-caprolactone). In one aspect, the polymer can be a poly(lactide-caprolactone), which, in various aspects, can be 95:5 poly(lactide-co-caprolactone), 85:15 poly(lactide-co-caprolactone), 75:25 poly(lactide-co-caprolactone), 65:35 poly(lactide-co-caprolactone), or 50:50 poly(lactide-co-caprolactone), where the ratios are mole ratios.

It is understood that any combination of the aforementioned biodegradable polymers can be used, including, but not limited to, copolymers thereof, mixtures thereof, or blends thereof. Likewise, it is understood that when a residue of a biodegradable polymer is disclosed, any suitable polymer, copolymer, mixture, or blend, that comprises the disclosed residue, is also considered disclosed. To that end, when multiple residues are individually disclosed (i.e., not in combination with another), it is understood that any combination of the individual residues can be used.

Non-limiting specific examples of polymer mixtures for use in a disclosed controlled release system, with their targeted delivery profile, include those mixtures listed in Table 1.

TABLE 1

Exemplary Polymer Mixtures for controlled release systems.

| First polymer | Second polymer | First polymer: | Second Polymer | Targeted delivery profile |
|---|---|---|---|---|
| 8515 DLG 4.5E | 8515 DLG 6A | 1. | 50:50 | 4-6 months delivery |
| 7525 DLG 7A | 6535 DLG 2E | 2. | 85:15 | 4-6 months delivery |
| 7525 DLG 5E | 6535 DLG 4A | 3. | 80:20 | 4-6 months delivery |
| 8515 DLG 5A | 7525 DLG 5E | 4. | 50:50 | 4-6 months delivery |
| 8515 DLG 7A | 7525 DLG 7E | 5. | 50:50 | 4-6 months delivery |
| 6535 DLG 4A | 2000 MW DLPL | 6. | various ratios | about 1 month delivery |
| 5050 DLG 4A | 2000 MW DLPL | 7. | various ratios | about 1 month delivery |
| 6535 DLG 4A | 5050 DLG 2A | 8. | various ratios | about 1 month delivery |
| 5050 DLG 4A | 5050 DLG 2A | 9. | various ratios | about 1 month delivery |

The following example defines the nomenclature used for the polymers in Table 1. The polymer, (8515 DLG 4.5E) refers to poly(D-lactide-co-glycolide), wherein the lactide to glycolide mole ratio is 85:15, wherein the copolymer exhibits an intrinsic viscosity of 0.45 dL/g, and wherein the copolymer comprises an ester (E) end group. The abbreviated (A) refers to an acid (e.g. a carboxylic acid) end group. The polymer 2000 MW DLPL refers to poly(D,L-lactide) having a molecular weight of about 2000 Daltons. The molecular weight of the polymers can be a measured value, or a value provided by a commercial supplier. As such, it is understood that molecular weights may only be close to the molecular weight of the polymer.

Thus, in one aspect, disclosed herein are polymers for use in the controlled release systems disclosed herein including but not limited to 8515 DLG 6A, 8515 DLG 5A, 8515 DLG 4.5E, 88515 DLG 5E, 515 DLG 7A, 7525 DLG 7A, 7525 DLG 7E, 7525 DLG 5E, 6535DLG 5E, 6353 DLG 2E, 6535 DLG 4A, 5050DLG 4A, 5050 DLG2A, and 2000 MW DLPL. Though not wishing to be tied to theory, it is generally understood that the greater the molecular weight of the polymer, the more viscous the polymer is. As viscosity increases the selection for a more purified polymeric form increases.

The solvents useful in the disclosed processes include "halogenated solvents" and "non-halogenated solvents." Non-limiting examples of non-halogenated solvents include: dimethylsulfoxide (DMSO), triacetin, N-methylpyrrolidone (NMP), 2-pyrrolidone, dimethylformamide (DMF), miglyol, isopropyl myristate, triethyl citrate, propylene glycol, ethyl carbonate, ethyl acetate, ethyl formate, methyl acetate, glacial acetic acid, polyethylene glycol (200), polyethylene glycol (400), acetone, methyl ethyl ketone, methanol, ethanol, n-propanol, iso-propanol, benzyl alcohol, glycerol, diethyl ether, tetrahydrofuran, glyme, diglyme, n-pentane, iso-pentane, hexane, heptane, isooctane, benzene, toluene, xylene (all isomers), and the like. Non-limiting examples of halogenated solvents include carbon tetrachloride, chloroform, methylene chloride (i.e., dicholoro methane,DCM), chloroethane, 1,1-dichloroethane, 1,1,1-trichloroethane, and 1,2-dichloroethane. Thus, in one aspect, the polymer solutions disclosed herein and for use in the disclosed methods and processes can comprise a bioactive agent and a solvent such as, for example, ethyl acetate or methylene chloride. It is understood that depending on the polymer in use, a movement from dichloromethoane to ethylacetate can increase the purity of the end product.

In one aspect, the disclosed microparticles can be dried by any conventional means known in the art such as via lyophilization or under nitrogen flow. Typically, the slower the drying rate the more pure the end product. Additionally, as the drying rate is still further slowed selection towards the most stable form of the polymorph increases. For example, lyophilization typically dries samples between 12 and 14 hours. By slowing the drying rate by merely passing nitrogen over the sample or allowing to air dry (time to dry 24-48 hours), selection for a more stable structure occurs. It is understood that typically lyophilizaton is a fast drying process whereas nitrogen flow is a slower rate process, but can be varied. Thus, in one aspect, drying time can be from 4 to 12 hours, from 4 to 16 hours, from 4 to 24 hours, from 4 to 48 hours, from 4 to 60 hours, from 12 to 14 hours, from 16 to 24 hours, or from 24 to 48 hours. For nitrogen flow, drying rate can be between 0.2 mLs per minute and 10 liters per minute (LPM), 0.1 and 5.0 LPM, 0.2 and 3.0 LPM, 0.2 and 2.0 LPM, or 0.2 and 1.0 LPM. Thus, in one aspect, the drying rate for the microparticle can be 0.1, 0.2, 0.3, 0.4, 0.5, 0.6, 0.7, 0.8, 0.9, 1.0, 1.1, 1.2, 1.3, 1.4, 1.5, 2.0, 2.5, 3.0, 3.5, 4.0, 4.5, 5.0, 6.0, 7.0, 8.0, 9.0, or 10 LPM.

A wide variety of bioactive agents can be used with the methods described herein. In one aspect, the bioactive agent can be a releasable bioactive agent, i.e., a bioactive agent that can be released from the controlled release system into adjacent tissues or fluids of a subject. In certain aspects, the bioactive agent can be in or on the controlled release system.

Various forms of the bioactive agent can be used, which are capable of being released from the controlled release system into adjacent tissues or fluids. To that end, a liquid or solid bioactive agent can be incorporated into the controlled release system described herein. The bioactive agents are at least very slightly water soluble, and preferably moderately water soluble. The bioactive agents can include salts of the active ingredient. As such, the bioactive agents can be acidic, basic, or amphoteric salts. They can be nonionic molecules, polar molecules, or molecular complexes capable of hydrogen bonding. The bioactive agent can be included in the compositions in the form of, for example, an uncharged molecule, a molecular complex, a salt, an ether, an ester, an amide, polymer drug conjugate, or other form to provide the effective biological or physiological activity.

Examples of bioactive agents that incorporated into systems herein include, but are not limited to, peptides, proteins such as hormones, enzymes, antibodies and the like, nucleic acids such as aptamers, iRNA, DNA, RNA, antisense nucleic acid or the like, antisense nucleic acid analogs or the like, low-molecular weight compounds, or high-molecular-weight compounds. Bioactive agents contemplated for use in the disclosed implantable composites include anabolic agents, antacids, anti-asthmatic agents, anti-cholesterolemic and anti-lipid agents, anti-coagulants, anti-convulsants, anti-diarrheals, anti-emetics, anti-infective agents including antibacterial and antimicrobial agents, anti-inflammatory agents, anti-manic agents, antimetabolite agents, anti-nauseants, anti-neoplastic agents, anti-obesity agents, anti-pyretic and analgesic agents, anti-spasmodic agents, anti-thrombotic agents, anti-tussive agents, anti-uricemic agents, anti-anginal agents, antihistamines (e.g., terfenadine), appetite suppressants, biologicals, cerebral dilators, coronary dilators, bronchiodilators, cytotoxic agents, decongestants, diuretics, diagnostic agents, erythropoietic agents, expectorants, gastrointestinal sedatives, hyperglycemic agents, hypnotics, hypoglycemic agents, immunomodulating agents, ion exchange resins, laxatives, mineral supplements, mucolytic agents, neuromuscular drugs, peripheral vasodilators, psychotropics, sedatives, stimulants, thyroid and anti-thyroid agents, tissue growth agents, uterine relaxants, vitamins, or antigenic materials.

Other bioactive agents include androgen inhibitors, polysaccharides, growth factors (e.g., a vascular endothelial growth factor-VEGF), hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestryramine, N-acetylprocainamide, acetaminophen, aspirin, ibuprofen, phenyl propanolamine hydrochloride, caffeine, guaifenesin, aluminum hydroxide, magnesium hydroxide, peptides, polypeptides, proteins, amino acids, interferons, cytokines, and vaccines.

Representative drugs that can be used as bioactive agents in the controlled release systems include, but are not limited to, peptide drugs, protein drugs, desensitizing materials, antigens, anti-infective agents such as antibiotics, antimicrobial agents, antiviral, antibacterial, antiparasitic, antifungal substances and combination thereof, antiallergenics, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, nonsteroidal anti-inflammatory agents, antiparkinsonian agents, antihypertensive agents, β-adrenergic blocking agents, nutritional agents, and the benzophenanthridine alkaloids. The agent can further be a substance capable of acting as a stimulant, sedative, hypnotic, analgesic, anticonvulsant, and the like.

The controlled release system can comprise a large number of bioactive agents either singly or in combination. Other bioactive agents include but are not limited to analgesics such as acetaminophen, acetylsalicylic acid, and the like; anesthetics such as lidocaine, xylocalne, and the like; anorexics such as dexadrine, phendimetrazine tartrate, and the like; antiarthritics such as methylprednisolone, ibuprofen, and the like; antiasthmatics such as terbutaline sulfate, theophylline, ephedrine, and the like; antibiotics such as sulfisoxazole, penicillin G, ampicillin, cephalosporins, amikacin, gentamicin, tetracyclines, chloramphenicol, erythromycin, clindamycin, isoniazid, rifampin, and the like; antifungals such as amphotericin B, nystatin, ketoconazole, and the like; antivirals such as acyclovir, amantadine, and the like; anticancer agents such as cyclophosphamide, methotrexate, etretinate, and the like; anticoagulants such as heparin, warfarin, and the like; anticonvulsants such as phenyloin sodium, diazepam, and the like; antidepressants such as isocarboxazid, amoxapine, and the like; antihistamines such as diphenhydramine HCl, chlorpheniramine maleate, and the like; hormones such as insulin, progestins, 17-alpha-hydroxy-porgesterone caproate, iso-allo-pregnanolonetestosterone, prenisolone, prednisone, dexamethasone estrogens (e.g.,. estradiol), corticoids, glucocorticoids, androgens, and the like; tranquilizers such as thorazine, diazepam, chlorpromazine HCl, reserpine, chlordiazepoxide HCl, and the like; antispasmodics such as belladonna alkaloids, dicyclomine hydrochloride, and the like; vitamins and minerals such as essential amino acids, calcium, iron, potassium, zinc, vitamin $B_{12}$, and the like; cardiovascular agents such as prazosin HCl, nitroglycerin, propranolol HCl, hydralazine HCl, pancrelipase, succinic acid dehydrogenase, and the like; peptides and proteins such as LHRH, somatostatin, calcitonin, growth hormone, glucagon-like peptides, growth releasing factor, angiotensin, FSH, EGF, bone morphogenic protein (BMP), erythopoeitin (EPO), interferon, interleukin, collagen, fibrinogen, insulin, Factor VIII, Factor IX, ENBREL®, RITUXAM®, HERCEPTIN®, alpha-glucosidase, Cerazyme/CEREDOSE®, vasopressin, ACTH, human serum albumin, gamma globulin, structural proteins, blood product proteins, complex proteins, enzymes, antibodies, monoclonal antibodies, and the like; prostaglandins; nucleic acids; carbohydrates; fats; narcotics such as morphine, codeine, and the like, psychotherapeutics; antimalarials, L-dopa, diuretics such as furosemide, spironolactone, and the like; antiulcer drugs such as rantidine HCl, cimetidine HCl, and the like, and calcium channel antagonist such as nimodipine and the like, lumefantrine, cilengitide, 3-hydroxy-3-methylglutaryl-coenzyme A reductase inhibitors such as lovastatin and the like.

The term "vasoconstriction" as used herein refers to the narrowing of the blood vessels resulting from contracting of the muscular wall of the vessels. When blood vessels constrict, the flow of blood is restricted or slowed. The term "vasodilation", which is the opposite of vasoconstriction as used herein, refers to the widening of blood vessels. The terms "vasoconstrictors," "vasopressors," or "pressors" as used herein refer to factors causing vasoconstriction. Vasoconstriction usually results in an increase of blood pressure and may be slight or severe. Vasoconstriction may result from disease, medication, or psychological conditions. Medications that cause vasoconstriction include, but are not limited to, catecholamines, antihistamines, decongestants, methylphenidate, cough and cold combinations, pseudoephedrine, and caffeine.

A vasodilator is a drug or chemical that relaxes the smooth muscle in blood vessels causing them to dilate. Dilation of arterial blood vessels (mainly arterioles) leads to a decrease in blood pressure. The relaxation of smooth muscle relies on removing the stimulus for contraction, which depends predominately on intracellular calcium ion concentrations and phosphorylation of myosin light chain (MLC). Thus, vasodilation predominantly works either 1) by lowering intracellular calcium concentration, or 2) by dephosphorylation of MLC, which includes the stimulation of myosin light chain phosphatase and the induction of calcium symporters and antiporters (which pump calcium ions out of the intracellular compartment). The re-uptake of ions into the sarcoplasmic reticulum of smooth muscle via exchangers and expulsion of ions across the plasma membrane also helps to accomplish vasodilation. The specific mechanisms to accomplish these effects vary from vasodilator to vasodilator and may be grouped as endogenous and exogenous. The term "endogenous" as used herein refers to proceeding from within or derived internally; or resulting from conditions within the organism rather than externally caused. The term "exogenous" as used herein refers to originating from outside; derived externally; or externally caused rather than resulting from conditions within the organism.

Vasodilation directly affects the relationship between mean arterial pressure and cardiac output and total peripheral resistance (TPR). Cardiac output may be computed by multiplying the heart rate (in beats/minute) and the stroke volume (the volume of blood ejected during systole). TPR depends on several factors, including, but not limited to, the length of the vessel, the viscosity of blood (determined by hematocrit), and the diameter of the blood vessel. Blood vessel diameter is the most important variable in determining resistance. An increase in either cardiac output or TPR cause a rise in the mean arterial pressure. Vasodilators work to decrease TPR and blood pressure through relaxation of smooth muscle cells in the tunica media layer of large arteries and smaller arterioles.

Vasodilation occurs in superficial blood vessels of warm-blooded animals when their ambient environment is hot; this process diverts the flow of heated blood to the skin of the animal, where heat may be more easily released into the atmosphere. Vasoconstriction is the opposite physiological process. Vasodilation and vasoconstriction are modulated naturally by local paracrine agents produced by endothelial cells (e.g., bradykinin, adenosine), as well as by an organism's autonomic nervous system and adrenal glands, both of which secrete catecholamines, such as norepinephrine and epinephrine, respectively.

Vasodilators are used to treat conditions such as hypertension, where the patient has an abnormally high blood pressure, as well as angina and congestive heart failure, where maintaining a lower blood pressure reduces the patient's risk of developing other cardiac problems.

In one aspect, disclosed herein are flowable sustained release microparticulate compositions comprising
  (i) a microparticulate formulation comprising a therapeutic amount of a substantially pure single polymorphic form of a bioactive agent, and
  (ii) a pharmaceutically acceptable carrier,
  wherein the microparticulate formulation comprises a plurality of microparticles of uniform size distribution, and wherein the substantially pure single polymorphic form of the bioactive agent is dispersed throughout each microparticle. In one aspect, the bioactive agent can be, for example, nimodipine.

In another aspect, the described invention provides a flowable sustained release microparticulate composition comprising:
  (i) a microparticulate formulation comprising a therapeutic amount of a substantially pure crystalline form I of nimodipine, and
  (ii) a pharmaceutically acceptable carrier,
  wherein the microparticulate formulation comprises a plurality of microparticles of uniform size distribution, and wherein the substantially pure crystalline form I of nimodipine is dispersed throughout each microparticle.

According to some embodiments, the substantially pure polymorphic form of nimodipine is selected from the group consisting of nimodipine Form I, nimodipine Form II, an amorphous form of nimodipine, and a combination thereof. According to some embodiments, the substantially pure polymorphic form of nimodipine is substantially pure nimodipine Form I. According to some embodiments, the substantially pure polymorphic form of nimodipine is substantially pure nimodipine Form II. According to some embodiments, the substantially pure polymorphic form of nimodipine is a substantially pure amorphous form of nimodipine.

According to some embodiments, the crystalline form I of nimodipine is characterized by a melting range of 122° C. to 127° C. According to some embodiments, the substantially pure crystalline form of nimodipine comprises nimodipine Form II characterized by a melting range of 110° C. to 117° C.

Figure 2:
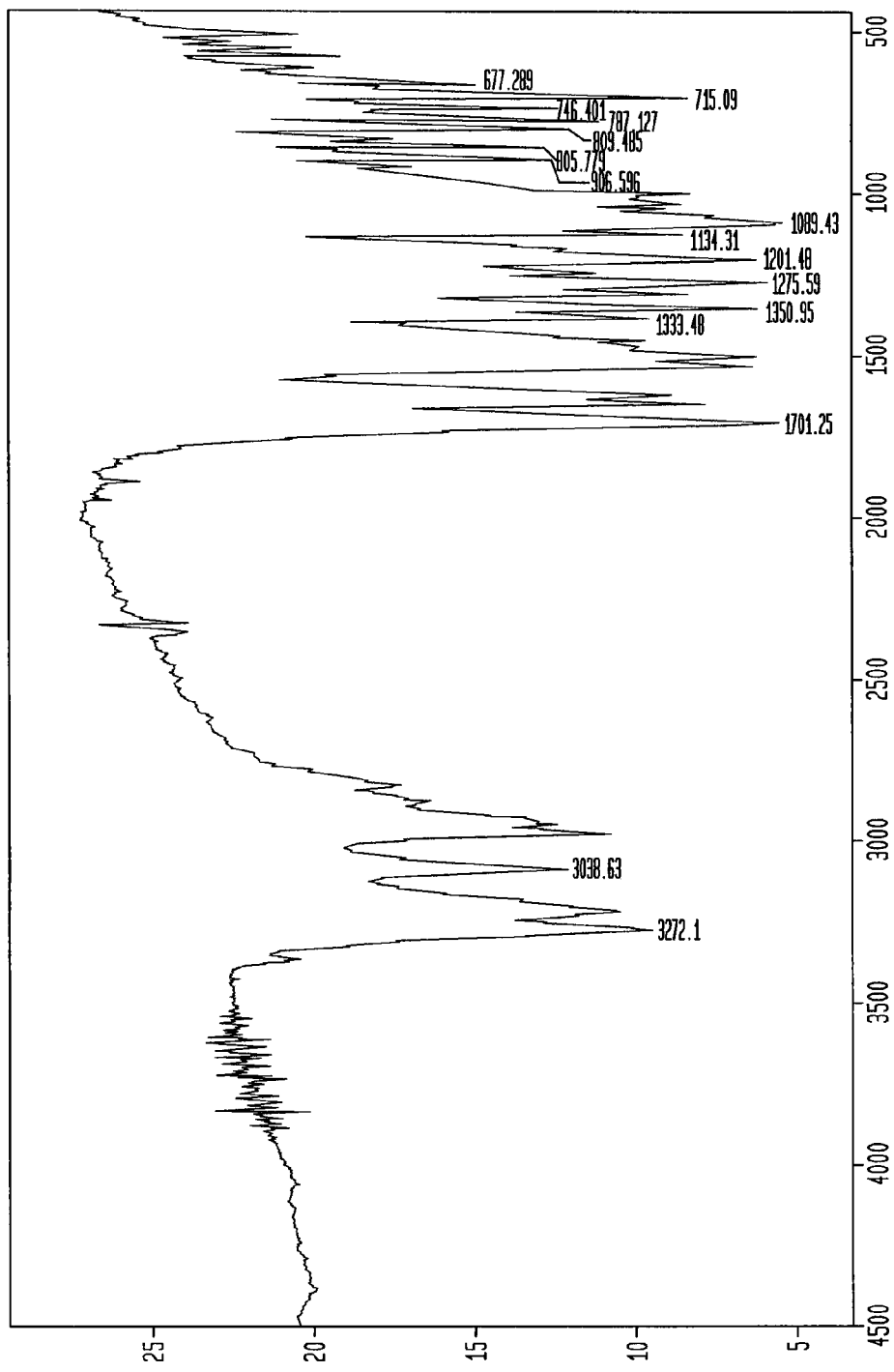
FIG. 2 shows an IR spectrum of nimodipine Form II as obtained using a sample of commercially available USP nimodipine Form II RS.

According to some embodiments, the substantially pure polymorphic form of nimodipine comprises nimodipine Form I characterized by an infra-red spectrum as depicted in FIG. 1. According to some embodiments, the substantially pure polymorphic form of nimodipine comprises nimodipine Form II characterized by an infra-red spectrum as depicted in FIG. 2.

Pharmaceutical compositions comprising a bioactive agent of the present invention in association with at least one pharmaceutically acceptable carrier or diluent can be manufactured in a conventional manner by mixing, granulating or coating methods. The pharmaceutical compositions may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Formulations of the pharmaceutical compositions include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active compounds may be in powder form for constitution with a suitable vehicle, e.g., sterile pyrogen-free water, before use.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, dichloromethane, acetonitrile, ethyl acetate, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

According to some embodiments, the combination of biodegradable polymers with a drug or pharmaceutically-active compound may allow a formulation that, when injected or inserted into body, is capable of sustained release of the drug.

Site-specific activity generally results if the location in the body into which the formulation is deposited is a fluid-filled space or some type of cavity, such as, for example, the subarachnoid space, the subdural cavity of a chronic subdural hematoma or the cavity left after the surgical evacuation of a hematoma, tumor or vascular malformation in the brain. This provides high concentrations of the drug at the site where activity is needed, and lower concentrations in the rest of the body, thus decreasing the risk of unwanted systemic side effects.

Site-specific delivery systems, for example, include use of microparticles (of about 1 μm to about 100 μm in diameter), thermoreversible gels (for example, PGA/PEG), and biodegradable polymers (for example, PLA, PLGA) that may be in the form of a film.

The delivery characteristics of the drug and the polymer degradation in vivo also can be modified. For example, polymer conjugation can be used to alter the circulation of the drug in the body and to achieve tissue targeting, reduce irritation and improve drug stability.

According to some embodiments, the pharmaceutically acceptable carrier includes, but is not limited to, a gel, a slow-release solid or semisolid compound, optionally as a sustained release gel, a slow-release solid or semisolid compound, the gel, slow-release solid or semisolid compound comprising the composition comprising a therapeutically effective amount of a compound of the invention. According to some such embodiments, the voltage-gated calcium channel antagonist is embedded into the pharmaceutically acceptable carrier or coated on at least one surface of the pharmaceutically acceptable carrier. The coating can be of any desired material, preferably a polymer or mixture of different polymers. Optionally, the polymer may be utilized during the granulation stage to form a matrix with the active ingredient so as to obtain a desired release pattern of the active ingredient. The gel, slow-release solid or semisolid compound is capable of releasing the active agent over a desired period of time. The gel, slow-release solid or semisolid compound can be implanted in a tissue within human brain, for example, but not limited to, in close proximity to a blood vessel, such as a cerebral artery. According to some such embodiments, the release of the active agent can produce a localized, site-specific pharmacologic effect over a desired amount of time.

According to some such embodiments, the release of the active agent can produce a diffuse pharmacologic effect over desired amount of time.

Suitable liquid or solid pharmaceutical preparations include, for example, microencapsulated dosage forms, and if appropriate, with one or more excipients, encochleated, coated onto microscopic particles, contained in liposomes, pellets for implantation into the tissue, or dried onto an object to be rubbed into the tissue. As used herein, the term "microencapsulation" refers to a process in which very tiny droplets or particles are surrounded or coated with a continuous film of polymeric material. Such pharmaceutical compositions also may be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The pharmaceutical compositions are suitable for use in a variety of drug delivery systems. For a brief review of methods for drug delivery, see Langer (1990) Science 249, 1527-1533, which is incorporated herein by reference.

Injectable depot forms are made by forming microencapsulated matrices of the drug in biodegradable polymers such as polylactide-polyglycolide. Depending upon the ratio of drug to polymer and the nature of the particular polymer employed, the rate of drug release may be controlled. Such long acting formulations may be formulated with suitable polymeric or hydrophobic materials (for example as an emulsion in an acceptable oil) or ion exchange resins, or as sparingly soluble derivatives, for example, as a sparingly soluble salt. Examples of other biodegradable polymers include poly (orthoesters) and poly(anhydrides). Depot injectable formulations are also prepared by entrapping the drug in liposomes or microemulsions which are compatible with body tissues.

For example, polyglycolide (PGA) is a linear aliphatic polyester developed for use in sutures. Studies have reported PGA copolymers formed with trimethylene carbonate, polylactic acid (PLA), and polycaprolactone. Some of these copolymers may be formulated as microparticles for sustained drug release.

Polyester-polyethylene glycol compounds can be synthesized; these are soft and may be used for drug delivery.

Poly (amino)-derived biopolymers may include, but are not limited to, those containing lactic acid and lysine as the aliphatic diamine (see, for example, U.S. Pat. No. 5,399,665), and tyrosine-derived polycarbonates and polyacrylates. Modifications of polycarbonates may alter the length of the alkyl chain of the ester (ethyl to octyl), while modifications of polyarylates may further include altering the length of the alkyl chain of the diacid (for example, succinic to sebasic), which allows for a large permutation of polymers and great flexibility in polymer properties.

Polyanhydrides are prepared by the dehydration of two diacid molecules by melt polymerization (see, for example, U.S. Pat. No. 4,757,128). These polymers degrade by surface erosion (as compared to polyesters that degrade by bulk erosion). The release of the drug can be controlled by the hydrophilicity of the monomers chosen.

Photopolymerizable biopolymers include, but are not limited to, lactic acid/polyethylene glycol/acrylate copolymers.

The term "hydrogel" refers to a substance resulting in a solid, semisolid, pseudoplastic or plastic structure containing a necessary aqueous component to produce a gelatinous or jelly-like mass. Hydrogels generally comprise a variety of polymers, including hydrophilic polymers, acrylic acid, acrylamide and 2-hydroxyethylmethacrylate (HEMA).

Naturally-occurring biopolymers include, but are not limited to, protein polymers, collagen, polysaccharides, and photopolymerizable compounds.

Protein polymers have been synthesized from self-assembling protein polymers such as, for example, silk fibroin, elastin, collagen, and combinations thereof.

Naturally-occurring polysaccharides include, but are not limited to, chitin and its derivatives, hyaluronic acid, dextran and cellulosics (which generally are not biodegradable without modification), and sucrose acetate isobutyrate (SAIB).

Chitin is composed predominantly of 2-acetamido-2-deoxy-D-glucose groups and is found in yeasts, fungi and marine invertebrates (shrimp, crustaceous) where it is a principal component of the exoskeleton. Chitin is not water soluble and the deacetylated chitin, chitosan, only is soluble in acidic solutions (such as, for example, acetic acid). Studies have reported chitin derivatives that are water soluble, very high molecular weight (greater than 2 million daltons), viscoelastic, non-toxic, biocompatible and capable of crosslinking with peroxides, gluteraldehyde, glyoxal and other aldehydes and carbodiamides, to form gels.

Hyaluronic acid (HA), which is composed of alternating glucuronidic and glucosaminidic bonds and is found in mammalian vitreous humor, extracellular matrix of the brain, synovial fluid, umbilical cords and rooster combs, from which it is isolated and purified, also can be produced by fermentation processes.

The formulations may be sterilized, for example, by terminal gamma irradiation, filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol, dichloromethane, ethyl acetate, acetonitrile, etc. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Formulations for parenteral (including but not limited to, subcutaneous, intradermal, intramuscular, intravenous, intrathecal and intraarticular) administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Another method of formulation of the compositions described herein involves conjugating a bioactive agent of the invention to a polymer that enhances aqueous solubility. Examples of suitable polymers include but are not limited to polyethylene glycol, poly-(d-glutamic acid), poly-(1-glutamic acid), poly-(1-glutamic acid), poly-(d-aspartic acid), poly-(1-aspartic acid), poly-(1-aspartic acid) and copolymers thereof. Polyglutamic acids having molecular weights between about 5,000 to about 100,000, with molecular weights between about 20,000 and about 80,000 may be used and with molecular weights between about 30,000 and about 60,000 may also be used. The polymer is conjugated via an ester linkage to one or more hydroxyls of an inventive epothilone using a protocol as essentially described by U.S. Pat. No. 5,977,163 which is incorporated herein by reference. Particular conjugation sites include the hydroxyl off carbon-21 in the case of 21-hydroxy-derivatives of the present invention. Other conjugation sites include, but are not limited, to the hydroxyl off carbon 3 and/or the hydroxyl off carbon 7.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

A bioactive agent of the invention may be provided in particles. According to some embodiments, the particles may contain the therapeutic agent(s) in a core surrounded by a coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, etc., and any combination thereof. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules that contain the bioactive agent of the invention in a solution or in a semi-solid state. According to some embodiments, the particle that may contain, in whole or in part, at least one therapeutic agent is a microparticle. According to some embodiments, the particle that may contain, in whole or in part, at least one therapeutic agent is a nanoparticle. According to some embodiments, the particles can be of virtually any shape. According to some embodiments, delivery of a bioactive agent of the invention using microparticle technology involves bioresorbable, polymeric particles that encapsulate the bioactive agent of the invention and at least one additional therapeutic agent.

According to another embodiment, the therapeutic agent(s) may be provided in strings. The strings may contain the therapeutic agent(s) in a core surrounded by a coating, or the therapeutic agent(s) may be dispersed throughout the string, or the therapeutic agent(s) may be absorbed into the string. The string may be of any order release kinetics, including zero order release, first order release, second order release, delayed release, sustained release, immediate release, etc., and any combination thereof. The string may include, in addition to the therapeutic agent(s), any of those materials routinely used in the art of pharmacy and medicine, including, but not limited to, erodible, nonerodible, biodegradable, or nonbiodegradable material or combinations thereof.

According to another embodiment, the bioactive agent of the invention may be provided in at least one sheet. The sheet may contain the bioactive agent of the invention and at least one additional therapeutic agent in a core surrounded by a coating, or the bioactive agent of the invention and at least one additional therapeutic agent may be dispersed throughout the sheet, or the therapeutic agent(s) may be absorbed into the sheet. The sheet may be of any order release kinetics, including zero order release, first order release, second order release, delayed release, sustained release, immediate release, etc., and any combination thereof. The sheet may include, in addition to the bioactive agent of the invention and at least one additional therapeutic agent, any of those materials routinely used in the art of pharmacy and medicine, including, but not limited to, erodible, nonerodible, biodegradable, or nonbiodegradable material or combinations thereof.

Both non-biodegradable and biodegradable polymeric materials may be used in the manufacture of particles for delivering a bioactive agent of the invention. Such polymers may be natural or synthetic polymers. The polymer is selected based on the period of time over which release is desired. Bioadhesive polymers of particular interest include bioerodible hydrogels as described by Sawhney et al in Macromolecules (1993) 26, 581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly (lauryl methacrylate), poly(phenyl methacrylate), poly(methyl acrylate), poly(isopropyl acrylate), poly(isobutyl acrylate), and poly(octadecyl acrylate). According to some embodiments, the bioadhesive polymers of the described invention include hyaluronic acid. According to some such embodiments, the bioadhesive polymer includes less than about 2.3% of hyaluronic acid.

II. Delivery Systems

According to another aspect, the present invention provides a delivery system for delivery of a composition comprising a therapeutic amount of a substantially pure form of nimodipine and optionally at least one additional therapeutic agent, where the composition is delivered locally to the cerebral arteries to prevent or reduce the incidence or severity of DCI, angiographic vasospasm, cortical spreading ischemia and/or microthromboembolism resulting from a disease, disorder, condition or injury. For example, the compositions can be delivered to the cerebral ventricles and then be carried by the flow of CSF to at least one cerebral artery of the subarachnoid space to effectuate a localized release of the pharmacologic agent(s), treating at least one of DCI, angiographic vasospasm, cortical spreading ischemia and microthromboembolism, and leading to an improved clinical outcome. The site of delivery is into at least one cerebral ventricle. This means a catheter is inserted into the ventricle and the pharmaceutical composition is injected through the catheter and eminates from the end of the catheter locally into the ventricle.

According to some embodiments, the therapeutic agent(s) may be contained in controlled release systems. In order to prolong the effect of a drug, it often is desirable to slow the absorption of the drug. This may be accomplished by the use of a liquid suspension of crystalline or amorphous material with poor water solubility. The rate of absorption of the drug then depends upon its rate of dissolution which, in turn, may depend upon crystal size and crystalline form. For example, according to some embodiments, a SABER™ Delivery System comprising a high-viscosity base component, such as sucrose acetate isobutyrate (SAIB), is used to provide controlled release of a bioactive agent of the invention. (See U.S. Pat. No. 5,747,058 and U.S. Pat. No. 5,968,542, incorporated herein by reference). When the high viscosity SAIB is formulated with drug, biocompatible excipients and other additives, the resulting formulation is liquid enough to inject easily with standard syringes and needles. After injection of a SABER™ formulation, the excipients diffuse away, leaving a viscous depot.

The term "controlled release" is intended to refer to any drug-containing formulation in which the manner and profile of drug release from the formulation are controlled. This refers to immediate as well as non-immediate release formulations, with non-immediate release formulations including, but not limited to, sustained release and delayed release formulations. The term "sustained release" (also referred to as "extended release") is used herein in its conventional sense to refer to a drug formulation that provides for gradual release of a drug over an extended period of time, and that preferably, although not necessarily, results in substantially constant blood levels of a drug over an extended time period. Alternatively, delayed absorption of a parenterally administered drug is accomplished by dissolving or suspending the drug in an oil vehicle. The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release formulation may be particularly suitable for treatment of chronic conditions. The term "long-term" release, as used herein, means that an implant is constructed and arranged to deliver therapeutic levels of the active ingredient for at least 7 days, and preferably about 30 to about 60 days. Long-term sustained release formulations are well-known to those of ordinary skill in the art and include some of the release systems described above.

Examples of microencapsulation processes and products; methods for the production of emulsion-based microparticles; emulsion-based microparticles and methods for the production thereof; solvent extraction microencapsulation with tunable extraction rates; microencapsulation process with solvent and salt; a continuous double emulsion process for making microparticles; drying methods for tuning microparticle properties, controlled release systems from polymer blends; polymer mixtures comprising polymers having different non-repeating units and methods for making and using the same; and an emulsion based process for preparing microparticles and workhead assembly for use with same are disclosed and described in, but not limited to U.S. Pat. No. 5,407,609 (entitled Microencapsulation Process and Products Thereof), U.S. Application Publication No. US 2007-0190154 A1 (entitled Method for the production of emulsion-based microparticles), U.S. Application Publication No. US 2007-0207211 A1 (entitled Emulsion-based microparticles and methods for the production thereof), U.S. Application Publication No. US 2010-0063179 A1 (entitled Solvent Extraction Microencapsulation With Tunable Extraction Rates), U.S. Application Publication No. US 2010-0291027 A1 (entitled Hyaluronic Acid (HA) Injection Vehicle), U.S. Application Publication No. US 2010-0069602 A1 entitled Microencapsulation Process With Solvent And Salt), U.S. Application No. US 2009-0162407 A1 (entitled Process For Preparing Microparticles Having A Low Residual Solvent Volume); U.S. Application Publication No. US 2010-0189763 A1 (entitled Controlled Release Systems From Polymer Blends); U.S. Application Publication No. US 2010-0216948 A1 (entitled Polymer Mixtures Comprising Polymers Having Different Non-Repeating Units And Methods For Making And Using Same); U.S. Application Publication No. US 2007-0092574 A1 (entitled "Controlled release compositions"); U.S. application Ser. No. 12/692,029 (entitled "Drying Methods for Tuning Microparticle Properties); U.S. Application Publication No. US 2011-0204533 A1 (entitled "Emulsion Based Process for Preparing Microparticles and Workhead for Use with Same); and U.S. Application Publication No. US 2011-0236497 A1 (entitled Composition and Methods for Improved Retention of a Pharmaceutical Composition at a Local Administration Site") The contents of each of these patents and patent application publications are incorporated herein by reference in its entirety.

According to some embodiments, the present invention comprises a delivery system that utilizes a semisolid, biodegradable, biocompatible delivery system or a biodegradable, biocompatible multiparticulate or microsphere dispersed and suspended in a semisolid, biodegradable, biocompatible delivery system for injection, deposition or implantation within or upon the body so as to facilitate local therapeutic effects. The term "biodegradable" as used herein refers to material that will degrade actively or passively over time by simple chemical processes, by action of body enzymes or by other similar mechanisms in the human body. The term "biocompatible" as used herein refers to causing no clinically relevant tissue irritation or necrosis at local site necessitating removal of the device prior to end of therapy based on a clinical risk/benefit assessment. The terms "in the body", "void volume", "resection pocket", "excavation", "injection site", or "deposition site" as used herein are meant to include all tissues of the body without limit, and may refer to spaces formed therein from injections, surgical incisions, tumor or tissue removal, tissue injuries, abscess formation, or any other similar cavity, space, or pocket formed thus by action of clinical assessment, treatment or physiologic response to disease or pathology as non-limiting examples thereof.

According to some embodiments, the semisolid delivery system comprises partially or in whole a biocompatible, biodegradable, viscous semisolid wherein the semisolid comprises a hydrogel. The term "hydrogel" as used herein refers to a substance resulting in a solid, semisolid, pseudoplastic, or plastic structure containing a necessary aqueous component to produce a gelatinous or jelly-like mass. The hydrogel incorporates and retains significant amounts of $H_2O$, which eventually will reach an equilibrium content in the presence of an aqueous environment. According to one embodiment, glyceryl monooleate, hereinafter referred to as GMO, is the intended semisolid delivery system or hydrogel. However, many hydrogels, polymers, hydrocarbon compositions and fatty acid derivatives having similar physical/chemical properties with respect to viscosity/rigidity may function as a semisolid delivery system.

According to one embodiment, the gel system is produced by heating GMO above its melting point (40-50° C.) and by adding a warm aqueous-based buffer or electrolyte solution, such as, for example, phosphate buffer or normal saline, which thus produces a three-dimensional structure. The aqueous-based buffer may be comprised of other aqueous solutions or combinations containing semi-polar solvents.

GMO provides a predominantly lipid-based hydrogel, which has the ability to incorporate lipophilic materials. The term "lipophilic" as used herein refers to preferring or possessing an affinity for a non-polar environment compared to a polar or aqueous environment. GMO further provides internal aqueous channels that incorporate and deliver hydrophilic compounds. The term "hydrophilic" as used herein refers to a material or substance having an affinity for polar substances, such as water. It is recognized that at room temperature (~25°

C.), the gel system may exhibit differing phases which comprise a broad range of viscosity measures.

According to one embodiment, two gel system phases are utilized due to their properties at room temperature and physiologic temperature (about 37° C.) and pH (about 7.4). Within the two gel system phases, the first phase is a lamellar phase of approximately 5% to approximately 15% $H_2O$ content and approximately 95% to approximately 85% GMO content. The lamellar phase is a moderately viscous fluid, that may be easily manipulated, poured and injected. The second phase is a cubic phase consisting of approximately 15% to approximately 40% $H_2O$ content and approximately 85%-60% GMO content. It has an equilibrium water content of approximately 35% to approximately 40% by weight. The term "equilibrium water content" as used herein refers to maximum water content in the presence of excess water. Thus the cubic phase incorporates water at approximately 35% to approximately 40% by weight. The cubic phase is highly viscous. The viscosity exceeds 1.2 million centipoise (cp) when measured by a Brookfield viscometer; where 1.2 million cp is the maximum measure of viscosity obtainable via the cup and bob configuration of the Brookfield viscometer. According to some such embodiments, a bioactive agent of the invention may be incorporated into the semisolid so as to provide a system for sustained, continuous delivery. According to some such embodiments, other therapeutic agents, biologically-active agents, drugs, medicaments and inactives may be incorporated into the semisolid for providing a local biological, physiological, or therapeutic effect in the body at various release rates.

According to some embodiments, alternative semisolids, modified formulations and methods of production are utilized such that the lipophilic nature of the semisolid is altered, or in the alternative, the aqueous channels contained within the semisolid are altered. Thus, various therapeutic agents in varying concentrations may diffuse from the semisolid at differing rates, or be released therefrom over time via the aqueous channels of the semisolid. Hydrophilic substances may be utilized to alter semisolid consistency or therapeutic agent release by alteration of viscosity, fluidity, surface tension or the polarity of the aqueous component. For example, glyceryl monostearate (GMS), which is structurally identical to GMO with the exception of a double bond at Carbon 9 and Carbon 10 of the fatty acid moiety rather than a single bond, does not gel upon heating and the addition of an aqueous component, as does GMO. However, because GMS is a surfactant, GMS is miscible in $H_2O$ up to approximately 20% weight/weight. The term "surfactant" as used herein refers to a surface active agent that is miscible in $H_2O$ in limited concentrations as well as polar substances. Upon heating and stirring, the 80% $H_2O$/20% GMS combination produces a spreadable paste having a consistency resembling hand lotion. The paste then is combined with melted GMO so as to form the cubic phase gel possessing a high viscosity referred to above.

According to some embodiments, hydrolyzed gelatin, such as commercially available Gelfoam™, is utilized for altering the aqueous component. Approximately 6.25% to 12.50% concentration of Gelfoam™ by weight may be placed in approximately 93.75% to 87.50% respectively by weight $H_2O$ or another aqueous based buffer. Upon heating and stirring, the $H_2O$ (or other aqeuous buffer)/Gelfoam™ combination produces a thick gelatinous substance. The resulting substance is combined with GMO; a product so formed swells and forms a highly viscous, translucent gel being less malleable in comparison to neat GMO gel alone.

According to some embodiments, polyethylene glycols (PEG's) may be utilized for altering the aqueous component to aid in drug solubilization. Approximately 0.5% to 40% concentration of PEG's (depending on PEG molecular weight) by weight can be placed in approximately 99.5% to 60% $H_2O$ or other aqueous based buffer by weight. Upon heating and stirring, the $H_2O$ (or other aqueous buffer)/PEG combination produces a viscous liquid to a semisolid substance. The resulting substance is combined with GMO, whereby a product so formed swells and forms a highly viscous gel.

According to some embodiments, the therapeutic agent releases from the semisolid through diffusion, conceivably in a biphasic manner. A first phase involves, for example, a lipophilic drug contained within the lipophilic membrane that diffuses therefrom into the aqueous channel. The second phase involves diffusion of the drug from the aqueous channel into the external environment. Being lipophilic, the drug may orient itself inside the GMO gel within its proposed lipid bi-layer structure. Thus, incorporating greater than approximately 7.5% of the drug by weight into GMO causes a loss of the integrity of the three-dimensional structure whereby the gel system no longer maintains the semisolid cubic phase, and reverts to the viscous lamellar phase liquid. According to another embodiment, about 1% to about 45% of therapeutic agent is incorporated by weight into a GMO gel at physiologic temperature without disruption of the normal three-dimensional structure. As a result, this system allows the ability of significantly increased flexibility with drug dosages. Because the delivery system is malleable, it may be delivered and manipulated in an implant site, for example, adjacent to cerebral arteries or the subarachnoid space, so as to adhere and conform to contours of walls, spaces, or other voids in the body as well as completely fill all voids existing. The delivery system ensures drug distribution and uniform drug delivery throughout the implant site. Ease of delivery and manipulation of the delivery system within a space, for example, but not limited to the subarachnoid space, is facilitated via a semisolid delivery apparatus. A semisolid delivery apparatus facilitates targeted and controlled delivery of the delivery system.

According to one embodiments, the multiparticulate component is comprised of biocompatible, biodegradable, polymeric or non-polymeric systems utilized to produce solid structures including, but not limited to, nonpareils, pellets, crystals, agglomerates, microspheres, or nanoparticles. According to some embodiments, the particle size is between about 30 μm to about 80 μm.

According to another embodiment, the multiparticulate component comprises of poly(D, L-Lactide-co-glycolide) (PLGA's). PLGA's are biodegradable polymer materials used for controlled and extended therapeutic agent delivery within the body. Such delivery systems offer enhanced therapeutic efficacy and reduced overall toxicity as compared to frequent periodic, systemic dosing. According to some embodiments, PLGA's systems consisting of differing molar ratios of the monomeric subunits may facilitate greater flexibility in engineering precise release profiles for accommodating targeted therapeutic agent delivery through alterations in the rate of polymer degradation. According to one embodiment, the PLGA composition is sufficiently pure so as to be biocompatible and remains biocompatible upon biodegradation. According to another embodiment, the PLGA polymer is designed and configured into microspheres having a therapeutic agent or drug entrapped therein, whereby the therapeutic agent is subsequently released therefrom by a method to be described in greater detail below. According to some such embodiments, the therapeutic agent is a calcium channel antagonist. According to some such embodiments, the therapeutic agent is nimodipine.

According to some embodiments, the multiparticulate component is comprised of poly (D, L-lactic-co-caprolactone). This biodegradable polymer material may be used for controlled and extended therapeutic agent delivery within the body with a similar drug release mechanism to that of the PLGA polymers. According to one embodiment, the multiparticulate microspheres also are produced using biodegradable and/or biocompatible non-polymeric materials such as GMS.

According to some embodiments, the multiparticulate component is further modified by methods used to encapsulate or coat the multiparticulate components using polymers of the same composition with the same or different drug substances, different polymers with the same or different drug substances, or with multiple layering processes containing no drug, the same drug, a different drug, or multiple drug substances. This allows the production of a multi-layered (encapsulated) multiparticulate system with a wide range of drug release profiles for single or multiple drug agents simultaneously. According to another embodiment, coating materials which control the rate of physical drug diffusion from the multiparticulate may be utilized alone or in concert with the aforementioned embodiments.

Alternatively, the present invention provides a delivery system that utilizes PLGA. The PLGA polymer contains ester bonds, which are labile to hydrolysis. The term "labile" as used herein refers to subject to increased degradation. When $H_2O$ penetrates the PLGA polymer, the ester bonds thereof are hydrolyzed, and monomers, being water soluble, are removed from the PLGA polymer, thus facilitating the physical release of the entrapped drug over time. According to some such embodiments, other classes of synthetic biodegradable, biocompatible polymers may be used for controlled and extended therapeutic agent delivery within the body, including polyanhydrides, poly(phosphates), polydioxanone, cellulosics and acrylics which are extended as non-limiting examples. According to some such embodiments, nonpolymeric materials may be utilized for controlled and extended therapeutic agent delivery within the body, including but not limited to sterols, sucrose fatty acid esters, fatty acids, and cholesteryl esters, which are extended as non-limiting examples.

Alternatively, the present invention provides a semisolid delivery system, which acts as a vehicle for local delivery of therapeutic agents, comprising a lipophilic, hydrophilic or amphophilic, solid or semisolid substance, heated above its melting point and thereafter followed by inclusion of a warm aqueous component so as to produce a gelatinous composition of variable viscosity based on water content. The therapeutic agent(s) is incorporated and dispersed into the melted lipophilic component or the aqueous buffer component prior to mixing and formation of the semisolid system. The gelatinous composition is placed within the semisolid delivery apparatus for subsequent placement, or deposition. Being malleable, the gel system is easily delivered and manipulated via the semisolid delivery apparatus in an implant site, where it adheres and conforms to contours of the implantation site, spaces, or other voids in the body as well as completely filling all voids existing. Alternatively, a multiparticulate component, comprised of a biocompatible polymeric or non-polymeric system is utilized for producing microspheres having a therapeutic agent entrapped therein. Following final processing methods, the microspheres are incorporated into the semisolid system and subsequently placed within the semisolid delivery apparatus so as to be easily delivered therefrom into an implant site or comparable space, whereby the therapeutic agent is subsequently released therefrom by (a) drug release mechanism(s).

According to some embodiments, drug load of the composition of the present invention contained within a delivery system ranges from about 25% to about 75% by weight. According to one embodiment, a therapeutically effective amount of the bioactive agent of the present invention is released from at least about one day to at least about 30 days after administration.

Combination

According to the methods of the invention, a bioactive agent of the invention may be formulated with at least one additional therapeutic agent. According to the methods of the invention, when a combination of a bioactive agent of the present invention and at least one other pharmaceutical agent are administered together, such administration can be sequential in time or simultaneous. For sequential administration, a bioactive agent of the present invention and the additional pharmaceutical agent can be administered in any order.

The terms "co-administration" or "combined administration" or the like as used herein encompass administration of the selected therapeutic agents to a single patient, and include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a bioactive agent of the present invention and a co-agent, are both administered to a patient simultaneously in the form of a single entity or dosage. The term "non-fixed combination" means that the active ingredients, e.g. a bioactive agent of the present invention and a co-agent, are both administered to a patient as separate entities either simultaneously, concurrently or sequentially with no specific time limits, wherein such administration provides therapeutically effective levels of the two bioactive agents in the body of the patient. The latter also applies to cocktail therapy, e.g. the administration of three or more active ingredients.

III. Methods

According to one aspect, disclosed herein are disclosed herein are processes for producing a substantially pure polymorphic form of a bioactive agent encapsulated into microparticles, wherein the process comprises: (a) providing a substantially pure crystalline form of the bioactive agent; (b) adding the substantially pure crystalline form of the bioactive agent to a polymer solution, thereby creating a mixture of the bioactive agent and the polymer solution; (c) homogenizing the mixture to form a disperse phase; (d) mixing the disperse phase with a continuous phase comprising a continuous process medium, thereby forming an emulsion comprising the bioactive agent; (e) forming and extracting the microparticles comprising the substantially pure polymorphic form of the bioactive agent; and (f) drying the microparticles. It is understood and herein contemplated that where a polymer solution comprises a polymer in an organic solvent forming a oil/water emulsion in the disperse phase, mixing the disperse phase with the continuous phase results in a double emulsion (i.e., a water/oil/water emulsion). Where the polymer solution comprises a polymer in an aqueous solvent such as water, only a single emulsion is formed upon mixing the dispersed phase with the continuous phase.

According to one aspect, the continuous process medium comprises a surfactant and the bioactive agent saturated with the solvent used in the polymer solution.

According to a further aspect, the polymer solutions of the aforementioned processes comprise a polymer and a solvent. It is understood and herein contemplated that the disclosed polymers comprise in one aspect polylactide, polylactide-co-glycolide, poly(orthoester), and poly(anhydride). In one aspect, the polylactide co-glycolide can be in a 85:15, 75:25, 65:35, or 50:50 ratio of lactide to glycolide. In a further aspect, the polymer comprises 8515 DLG 6A, 8515 DLG 5A, 8515 DLG 4.5E, 88515 DLG 5E, 515 DLG 7A, 7525 DLG 7A, 7525 DLG 7E, 7525 DLG 5E, 6535DLG 5E, 6353 DLG 2E, 6535 DLG 4A, 5050DLG 4A, 5050 DLG2A, and 2000 MW DLPL. In another aspect, the solvent can comprise ethyl acetate or dichloromethane.

According to another aspect, the processes disclosed herein comprise drying the microparticle over a 10 to 48 hour period.

It is understood and herein contemplated that stability and purity of the end product generally increase with increased molecular weight and thus increased viscosity of the polymer. Thus a move from a 6535 DLG polymer of one molecular weight of a 6535 DLG polymer of increased molecular weight will increase the purity of the end product. Similarly, depending on the polymer used, a change from the solvent in the polymer solution to a different solvent can increase purity as well. For example a change from dichloromethane to ethylacetate can increase purity. It is further understood that purity can be increased by slowing down the drying rate of the microparticle.

According to another aspect, the disclosure herein also provides for the targeted selection of a particular polymorph form over other forms where desired. In one aspect, where a purified amorphous polymorphic form rather than a stable crystalline form of the polymorph is desired a decrease in the lactide to glycolide ratio of the polymer can be made. For example, a change from a 6535 DLG to a 5050 DLG can change the end product polymorphic form from Modification 1 of nimodipine to the amorphic form.

According to another aspect, it is understood that by slowing drying time, in addition to increasing purity, selection for the most stable form of the polymorph is selected as the drying process slows. For example, by slowing drying of a microparticle prepared from a 5050 GLG 4A polymer in ethyl acetate from 14 hours to 24 to 48 hours the end product moves from the amorphic form to the Modification II and eventually to Modification I. It is understood and herein contemplated that any end product can be achieved by adjusting the polymer and solvent for use in the polymer solution and adjusting drying time to achieve the desired result.

According to another aspect, the described invention provides a method of treating at least one cerebral artery in a subarachnoid space at risk of interruption due to a sudden brain injury in a human subject, comprising (a) providing a flowable sustained release microparticulate composition comprising (i) a microparticulate formulation containing a therapeutic amount of a substantially pure polymorphic form of nimodipine, wherein the microparticulate formulation comprises a plurality of microparticles of uniform size distribution, wherein the polymorph is dispersed throughout each microparticle, and wherein the therapeutic amount is effective to treat the delayed complication and (ii) a pharmaceutically acceptable carrier; and (b) administering the pharmaceutical composition locally into a cerebral ventricle so that the microparticulate formulation flows from the cerebrospinal fluid (CSF) in the cerebral ventricle into the cerebrospinal fluid (CSF) in the subarachnoid space before releasing the polymorph in the subarachnoid space, wherein the therapeutic agent contacts and flows around the at least one cerebral artery in the subarachnoid space without entering systemic circulation in an amount to cause unwanted side effects.

Delayed complications associated with sudden brain injury include, but are not limited to, a delayed cerebral ischemia, an intracerebral hematoma, an intraventricular hemorrhage, a fever, an angiographic vasospasm, a microthromboembolus, cortical spreading ischemia (CSI), a behavioral deficit, a neurological deficit, and neuronal cell death. According to some embodiments, the sudden brain injury is a subarachnoid hemorrhage.

According to some embodiments, the pharmaceutical composition is delivered into a subarachnoid space within about 0.001 mm to about 10 mm, within about 0.010 mm to about 10 mm, within about 0.020 mm to about 10 mm, within about 0.030 mm to about 10 mm, within about 0.040 mm to about 10 mm, within 0.050 mm to about 10 mm, within about 0.060 mm to about 10 mm, within about 0.070 mm to about 10 mm, within about 0.080 mm to about 10 mm, within about 0.090 mm to about 10 mm, within about 0.1 mm to about 10 mm, within about 0.2 mm to about 10 mm, within about 0.3 mm to about 10 mm, within about 0.4 mm to about 10 mm, within about 0.5 mm to about 10 mm, within about 0.6 mm to about 10 mm, within about 0.7 mm to about 10 mm, within about 0.8 mm to about 10 mm, within about 0.9 mm to about 10 mm, within about 1.0 mm to about 10 mm, within about 1.1 mm to about 10 mm, within about 1.2 mm to about 10 mm, within about 1.3 mm to about 10 mm, within about 1.4 mm to about 10 mm, within about 1.5 mm to about 10 mm, within about 1.6 mm to about 10 mm, within about 1.7 mm to about 10 mm, within about 1.8 mm to about 10 mm, within about 1.9 mm to about 10 mm, within about 2.0 mm to about 10 mm, within about 2.1 mm to about 10 mm, within about 2.2 mm to about 10 mm, within about 2.3 mm to about 10 mm, within about 2.4 mm to about 10 mm, within about 2.5 mm to about 10 mm, within about 2.6 mm to about 10 mm, within about 2.7 mm to about 10 mm, within about 2.8 mm to about 10 mm, within about 2.9 mm to about 10 mm, within about 3.0 mm to about 10 mm, within about 3.1 mm to about 10 mm, within about 3.2 mm to about 10 mm, within about 3.3 mm to about 10 mm, within about 3.4 mm to about 10 mm, within about 3.5 mm to about 10 mm, within about 3.6 mm to about 10 mm, within about 3.7 mm to about 10 mm, within about 3.8 mm to about 10 mm, within about 3.9 mm to about 10 mm, within about 4.0 mm to about 10 mm, within about 4.1 mm to about 10 mm, within about 4.2 mm to about 10 mm, within about 4.3 mm to about 10 mm, within about 4.4 mm to about 10 mm, within about 4.5 mm to about 10 mm, within about 4.6 mm to about 10 mm, within about 4.7 mm to about 10 mm, within about 4.8 mm to about 10 mm, within about 4.9 mm to about 10 mm, within about 5.0 mm to about 10 mm, within about 5.1 mm to about 10 mm, within about 5.2 mm to about 10 mm, within about 5.3 mm to about 10 mm, within about 5.4 mm to about 10 mm, within about 5.5 mm to about 10 mm, within about 5.6 mm to about 10 mm, within about 5.7 mm to about 10 mm, within about 5.8 mm to about 10 mm, within about 5.9 mm to about 10 mm, within about 6.0 mm to about 10 mm, within about 6.1 mm to about 10 mm, within about 6.2 mm to about 10 mm, within about 6.3 mm to about 10 mm, within about 6.4 mm to about 10 mm, within about 6.5 mm to about 10 mm, within about 6.6 mm to about 10 mm, within about 6.7 mm to about 10 mm, within about 6.8 mm to about 10 mm, within about 6.9 mm to about 10 mm, within about 7.0 mm to about 10 mm, within about 7.1 mm to about 10 mm, within about 7.2 mm to about 10 mm, within about 7.3 mm to about 10 mm, within about 7.4 mm to about 10 mm, within about 7.5 mm to about 10 mm, within about 7.6 mm to about 10 mm, within about 7.7 mm to about 10 mm, within about 7.8 mm to about 10 mm, within about 7.9 mm to about 10 mm, within about 8.0 mm to about 10 mm, within about 8.1 mm to about 10 mm, within about 8.2 mm to about 10 mm, within about 8.3 mm to about 10 mm, within about 8.4 mm to about 10 mm, within about 8.5 mm to about 10 mm, within about 8.6 mm to about 10 mm, within about 8.7 mm to about 10 mm, within about 8.8 mm to about 10 mm, within about 8.9 mm to about 10 mm, within about 9.0 mm to about 10 mm, within about 9.1 mm to about 10 mm, within about 9.2 mm to about 10 mm, within about 9.3 mm to about 10 mm, within about 9.4 mm to about 10 mm, within about 9.5 mm to about 10 mm, within about 9.6 mm to about 10 mm, within about 9.7 mm to about 10 mm, within about 9.8 mm to about 10 mm, or within about 9.9 mm to about 10 mm of a site of brain injury or into a blood vessel in close proximity to the site of brain injury.

According to some embodiments, the pharmaceutical composition is injected into the cerebral ventricles via a catheter or tube inserted into one of the lateral, third, or fourth ventricles, or the subarachnoid cisterns of the brain.

According to another embodiment, the pharmaceutically acceptable carrier comprises a slow-release solid compound. According to one such embodiment, the bioactive agent of the present invention is embedded in the slow-release solid compound or coated on the slow-release solid compound. According to yet another embodiment, the pharmaceutically acceptable carrier comprises a slow-release microparticle containing the bioactive agent of the present invention. According to another embodiment, for example, the microparticle contains poly (D, L-Lactide-co-glycolide). According to another embodiment, the pharmaceutically acceptable carrier is a gel compound, such as a biodegradable hydrogel.

According to another embodiment, administration of the pharmaceutical composition into the injured brain can improve appetite.

According to another embodiment, administration of the pharmaceutical composition into the injured brain can improve symptoms of focal neurological changes, such as hemiparesis, hemianesthesia, apraxia, ataxia or paresis.

According to another embodiment, the pharmaceutical composition can exert a local therapeutic effect. Alternatively, the pharmaceutical composition exerts a diffuse or general therapeutic effect throughout the brain.

According to one embodiment, a composition comprising the substantially pure polymorphic form of nimodipine, is administered to the subject having angiographic vasospasm or at risk of having angiographic vasospasm in a therapeutically effective amount to treat the angiographic vasospasm and subsequent development of DCI. A therapeutically effective amount of the substantially pure polymorphic form of nimodipine, is that amount necessary to treat as defined, including to ameliorate, reduce or eliminate altogether, one or more symptoms relating to angiographic vasospasm, preferably including brain damage that can result from the angiographic vasospasm, such as DCI. Brain damage may be measured anatomically using medical imaging techniques to measure infarct sizes. Alternatively or in conjunction, brain damage may be measured functionally in terms of cognitive, sensory or motor or other skills of the subject. According to another embodiment, a composition comprising the substantially pure polymorphic form of nimodipine, is administered to the subject having or at risk of having angiographic vasospasm in a therapeutically effective amount to treat the angiographic vasospasm. According to another embodiment, the present invention provides a method of treating, preventing or reducing the severity of angiographic vasospasm and/or DCI comprising the step of administering into the cerebral ventricles a composition comprising a suspension of sustained release microparticles comprising a therapeutically effective amount of the substantially pure polymorphic form of nimodipine, on or in microparticles.

According to another embodiment, the method comprises the step of administering into the cerebral ventricles a composition comprising the substantially pure polymorphic form of nimodipine in or on microparticles that are carried by the CSF flow into the subarachnoid space to deliver drug substance at the site of angiographic vasospasm and/or other sites in the subarachnoid space where blood vessels are located that participate in microthromboembolism and cortical spreading ischemia and thus are important potential mediators of DCI. Because the microparticles are delivered locally to the brain, the dosage required to prevent angiographic vasospasm will be appropriate to reduce, prevent or circumvent the main side effect that prevents the administration of higher systemic doses, e.g., hypotension.

According to one embodiment, the method comprises the step of administering into the cerebral ventricles the substantially pure polymorphic form of nimodipine in the form of a plurality of microparticles that is carried by CSF flow into the subarachnoid space to targeted cerebral arteries. In these embodiments, the site of delivery is into at least one cerebral ventricle. This means a catheter is inserted into the ventricle and the pharmaceutical composition is injected through the catheter and emanates from the end of the catheter locally into the ventricle. The CSF circulation then can carry the pharmaceutical composition from the site of administration in the ventricle. If the injection was in the lateral ventricle, the path would be from the lateral ventricle, through the foramen of Monro to the third ventricle, through the aqueduct of Sylvius to the fourth ventricle, out the lateral or medial apertures of the fourth ventricle into the perimedullary cisterns, then into the other cisterns of the cranial subarachnoid space. The circulation of CSF is often slowed after SAH and the subarachnoid space contains blood clots. Thus, the pharmaceutical composition may become trapped in the blood clots and thereby, there would be localized release of the pharmacological agent(s) from the composition where they would exert a pharmacological effect in the adjacent arteries and brain.

According to another embodiment, a method for treating a cerebral vasospasm in a human subject comprises (a) providing a flowable sustained release microparticle composition comprising: (i) a microparticulate formulation comprising a therapeutic amount of a substantially pure crystalline form I of nimodipine having an X-ray Powder Diffraction (XRPD) spectrum substantially the same as the X-ray Powder Diffraction (XRPD) spectrum shown in FIG. 11, wherein the microparticulate formulation comprises a plurality microparticles of uniform size distribution, wherein the therapeutic amount is effective to treat a delayed complication of the constriction of a cerebral artery, and (ii) a pharmaceutical carrier; and b) administering the pharmaceutical composition to the human subject locally via surgical injection in a subarachnoid cistern closest to a cerebral artery at risk for vasospasm, such that the composition flows around the cerebral artery without entering the systemic circulation in an amount to cause unwanted side effects; wherein the pharmaceutical composition produces a localized pharmacologic effect; and wherein the therapeutic amount is effective to treat the cerebral vasospasm. According to some embodiments, the pharmaceutical composition is trapped in the blood clot(s) facilitating localized release of the therapeutic amount of the substantially pure crystalline form 1 of nimodipine.

According to some embodiments, the carrier is a gel compound. According to some embodiments, the carrier is a slow-release solid compound.

According to some embodiments, the cistern closest to a cerebral artery at risk for vasospasm in step (b) is from about 0.001 mm to about 10 mm from the cerebral artery. According to some embodiments, the pharmaceutical composition is delivered into a cistern within about 0.001 mm to about 10 mm, within about 0.010 mm to about 10 mm, within about 0.020 mm to about 10 mm, within about 0.030 mm to about 10 mm, within about 0.040 mm to about 10 mm, within 0.050 mm to about 10 mm, within about 0.060 mm to about 10 mm, within about 0.070 mm to about 10 mm, within about 0.080 mm to about 10 mm, within about 0.090 mm to about 10 mm, within about 0.1 mm to about 10 mm, within about 0.2 mm to about 10 mm, within about 0.3 mm to about 10 mm, within about 0.4 mm to about 10 mm, within about 0.5 mm to about 10 mm, within about 0.6 mm to about 10 mm, within about 0.7 mm to about 10 mm, within about 0.8 mm to about 10 mm, within about 0.9 mm to about 10 mm, within about 1.0 mm to about 10 mm, within about 1.1 mm to about 10 mm, within about 1.2 mm to about 10 mm, within about 1.3 mm to about 10 mm, within about 1.4 mm to about 10 mm, within about 1.5 mm to about 10 mm, within about 1.6 mm to about 10 mm, within about 1.7 mm to about 10 mm, within about 1.8 mm to about 10 mm, within about 1.9 mm to about 10 mm, within about 2.0 mm to about 10 mm, within about 2.1 mm to about 10 mm, within about 2.2 mm to about 10 mm, within about 2.3 mm to about 10 mm, within about 2.4 mm to about 10 mm, within about 2.5 mm to about 10 mm, within about 2.6 mm to about 10 mm, within about 2.7 mm to about 10 mm, within about 2.8 mm to about 10 mm, within about 2.9 mm to about 10 mm, within about 3.0 mm to about 10 mm, within about 3.1 mm to about 10 mm, within about 3.2 mm to about 10 mm, within about 3.3 mm to about 10 mm, within about 3.4 mm to about 10 mm, within about 3.5 mm to about 10 mm, within about 3.6 mm to about 10 mm, within about 3.7 mm to about 10 mm, within about 3.8 mm to about 10 mm, within about 3.9 mm to about 10 mm, within about 4.0 mm to about 10 mm, within about 4.1 mm to about 10 mm, within about 4.2 mm to about 10 mm, within about 4.3 mm to about 10 mm, within about 4.4 mm to about 10 mm, within about 4.5 mm to about 10 mm, within about 4.6 mm to about 10 mm, within about 4.7 mm to about 10 mm, within about 4.8 mm to about 10 mm, within about 4.9 mm to about 10 mm, within about 5.0 mm to about 10 mm, within about 5.1 mm to about 10 mm, within about 5.2 mm to about 10 mm, within about 5.3 mm to about 10 mm, within about 5.4 mm to about 10 mm, within about 5.5 mm to about 10 mm, within about 5.6 mm to about 10 mm, within about 5.7 mm to about 10 mm, within about 5.8 mm to about 10 mm, within about 5.9 mm to about 10 mm, within about 6.0 mm to about 10 mm, within about 6.1 mm to about 10 mm, within about 6.2 mm to about 10 mm, within about 6.3 mm to about 10 mm, within about 6.4 mm to about 10 mm, within about 6.5 mm to about 10 mm, within about 6.6 mm to about 10 mm, within about 6.7 mm to about 10 mm, within about 6.8 mm to about 10 mm, within about 6.9 mm to about 10 mm, within about 7.0 mm to about 10 mm, within about 7.1 mm to about 10 mm, within about 7.2 mm to about 10 mm, within about 7.3 mm to about 10 mm, within about 7.4 mm to about 10 mm, within about 7.5 mm to about 10 mm, within about 7.6 mm to about 10 mm, within about 7.7 mm to about 10 mm, within about 7.8 mm to about 10 mm, within about 7.9 mm to about 10 mm, within about 8.0 mm to about 10 mm, within about 8.1 mm to about 10 mm, within about 8.2 mm to about 10 mm, within about 8.3 mm to about 10 mm, within about 8.4 mm to about 10 mm, within about 8.5 mm to about 10 mm, within about 8.6 mm to about 10 mm, within about 8.7 mm to about 10 mm, within about 8.8 mm to about 10 mm, within about 8.9 mm to about 10 mm, within about 9.0 mm to about 10 mm, within about 9.1 mm to about 10 mm, within about 9.2 mm to about 10 mm, within about 9.3 mm to about 10 mm, within about 9.4 mm to about 10 mm, within about 9.5 mm to about 10 mm, within about 9.6 mm to about 10 mm, within about 9.7 mm to about 10 mm, within about 9.8 mm to about 10 mm, or within about 9.9 mm to about 10 mm from the cerebral artery.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any method and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be considered as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Synthesis of (RS)-isopropyl-2-methoxyethyl-1,4-dihydro-2,6-dimethyl-4(3-nitrophenyl)pyridine-3,5-dicarboxylate

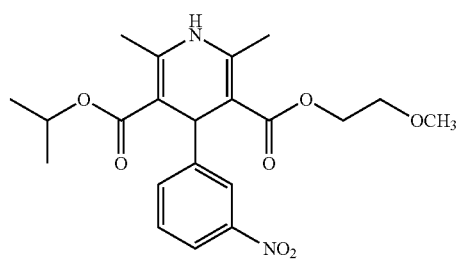 [SMILES: COCCOC(=O)C1=C(C)NC(C)=C(C(=O)OC(C)C)C1c1cccc([N+](=O)[O-])c1]

Nimodipine was synthesized according to the following schemes. In Scheme 1, a solution of ammonium hydroxide was added to 2-methoxyethyl acetoacetate (MEAA) and the reaction mixture was held until completion. The reaction mixture was then partitioned with toluene. The aqueous phase was back extracted using additional toluene. The combined organic phase was concentrated by distillation using heating and reduced pressure. The crude product Intermediate I, (2'-methoxyethyl)-3-amino-3-methylacrylate, was distilled using high vacuum distillation.

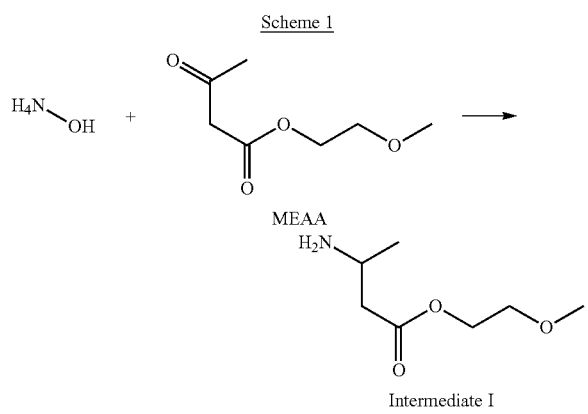

In Scheme 2, 3-nitrobenzaldehyde was added to cooled isopropanol. The mixture was heated to yield a completely dissolved solution, to which, was added isopropyl acetatoacetate, propionic acid and piperidine. The resultant solution was held until completion of reaction to yield crude Intermediate II, 3-oxo-2-)₃-nitrophenylmethylene)butanoic acid isopropyl ester. The resultant mixture was then cooled and held for crystal formation. The crude Intermediate II crystals were isolated by centrifugation, rinsed with additional isopropanol, subsequently charged into cooled isopropanol, heated and agitated, then isolated again by centrifugation and finally dried using vacuum and heating to yield pure Intermediate II.

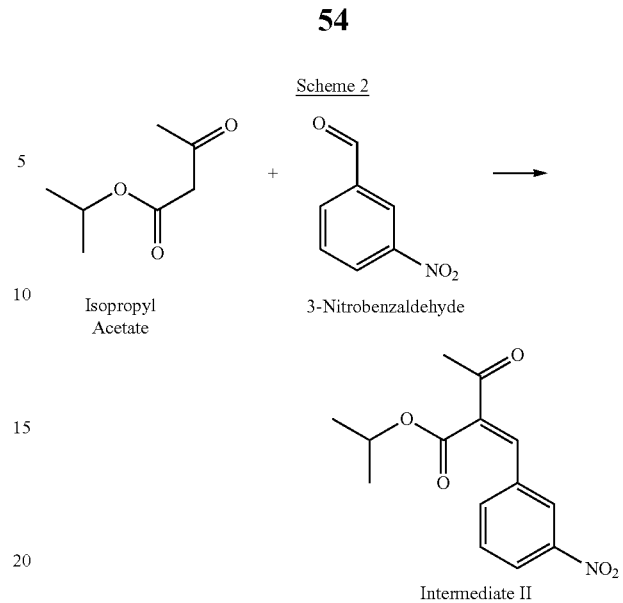

In Scheme 3, Intermediate I and Intermediate II were charged into isopropanol. The resulting mixture was heated and held at reflux under a nitrogen stream. Then, propionic acid and piperidine were added to the mixture, while being held at reflux until the reaction was completed. A portion of the isopropanol from the reaction mixture was removed by distillation. The mixture was cooled, charged with methanol and the mixture was heated until complete dissolution. The solution was cooled and held for crystal formation to yield crude crystals of Nimodipine, (RS)-isopropyl-2-methoxyethyl-1,4-dihydro-2,6-dimethyl-4(3-nitrophenyl)pyridine-3,5-dicarboxylate. The crude Nimodipine crystals were isolated by centrifugation, rinsed with isopropanol and dried using vacuum and heating and subjected to two further rounds of purification.

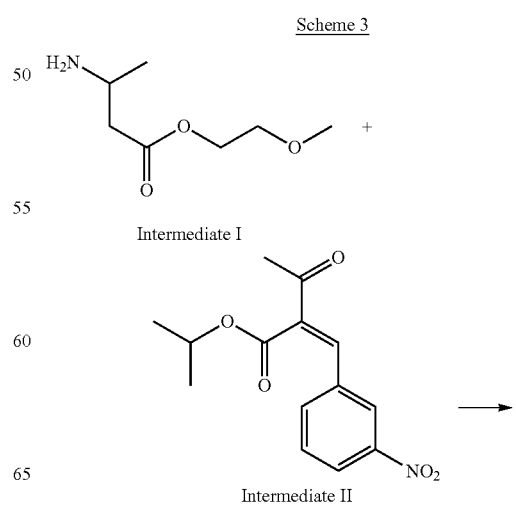

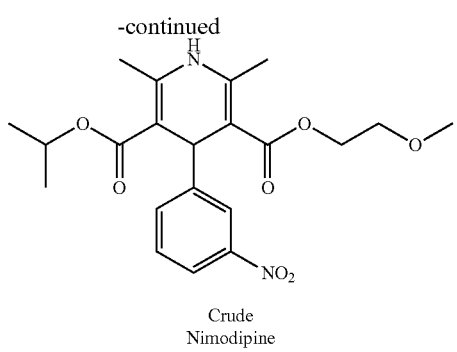

Crude Nimodipine

In the first purification step, the Crude Nimodipine crystals of Scheme 3 were dissolved in isopropanol. The resulting solution was heated to reflux and then cooled and held for crystal formation. The crystals were isolated by centrifugation. In the second purification step, Nimodipine crystals collected from the first purification step were once again dissolved in isopropanol. The resulting solution was heated until reflux, filtered and additional isopropanol were passed through the filter. The solution was then once again heated to reflux and a portion of the isopropanol was removed from the mixture by distillation. The reaction mixture was then charged with water and the mixture was heated until reflux, held and then cooled slowly for product precipitation. The remaining portions of isopropanol and water were removed by vacuum distillation. The mixture was cooled and held for crystal formation. The resulting crystals were isolated by centrifugation, further rinsed with water and dried using vacuum and heating to yield Pure Nimodipine. The purified product was then milled and subsequently micronized to yield Milled Nimodipine and Micronized Nimodipine, respectively. The particle size distribution of micronized nimodipine sample, as determined by diffraction produced when exposed to laser light at a wavelength of 633 nm, was found to range between about 0.4 µm to about 12 µm.

Figure 3:
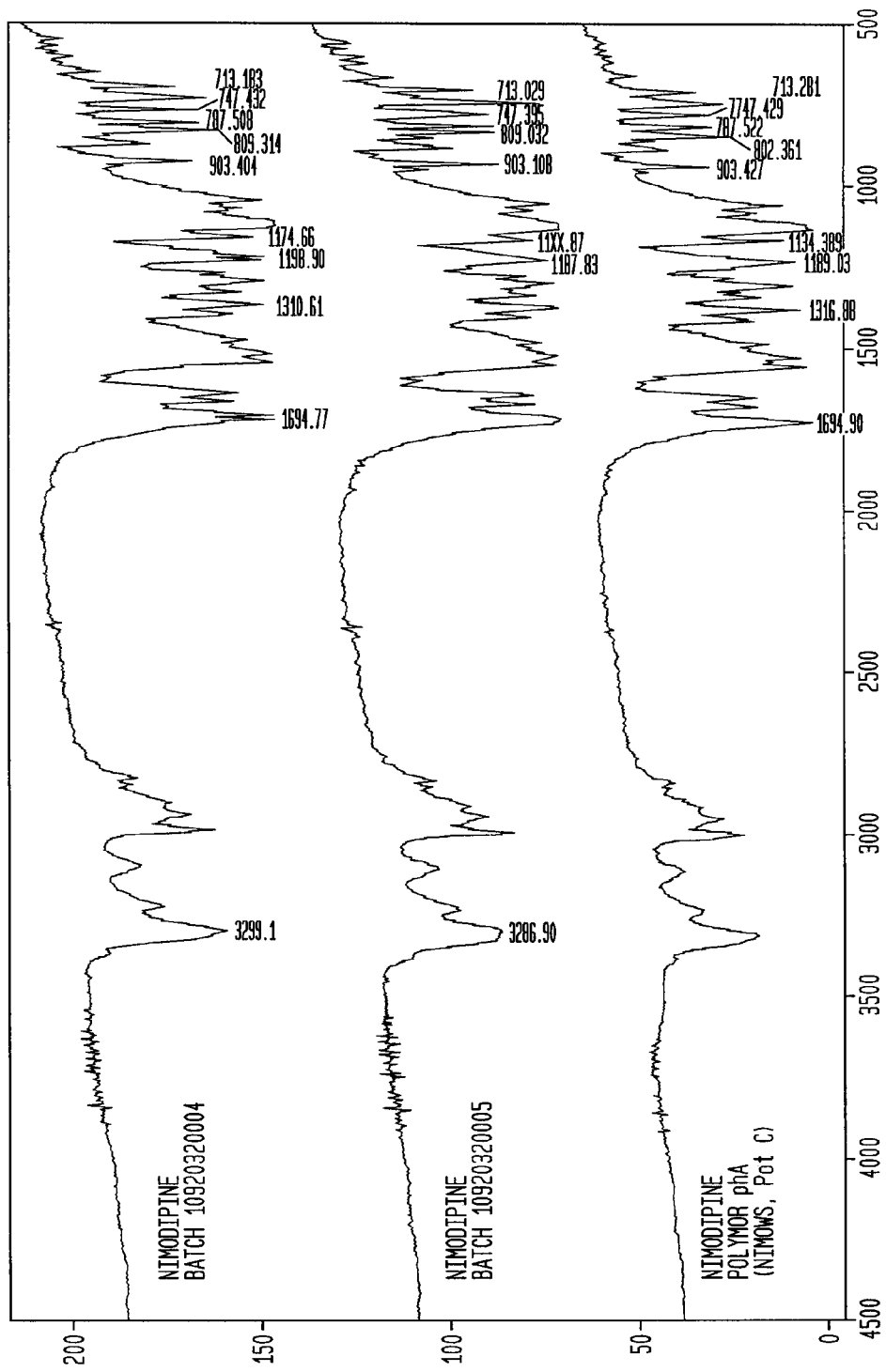
FIG. 3 shows an overlay of IR spectra, obtained with samples of two exemplary synthetic batches of nimodipine with the IR spectrum of Form I, obtained using a sample of the commercially available USP nimodipine Form I RS as a reference standard.

The nimodipine structure of the final product was confirmed by mass spectrum (MS), $^1$H NMR spectrum and $^{13}$C NMR spectrum using a sample of commercially available USP nimodipine as a reference standard. Molecular Mass: m/z 418 (M+); $^1$H NMR (250 MHz, CDCl$_3$); $^{13}$C NMR (62.8 MHz, CDCl$_3$). The melting range was found to be about 122° C. to about 127° C. The synthesized batches of nimodipine did not display any optical activity, confirming that they represent racemic mixture of opposite enantiomers. Nimodipine polymorphism analysis using infrared (IR) absorption spectrum measurements with the commercially available USP nimodipine as a reference standard revealed that the synthesized batches represented racemate Form I and not the conglomerate Form II, as shown in FIG. 3.

Example 2

Encapsulation Process and Characterization of the Resulting Microparticles

Nimodipine microparticles were prepared by an oil in water (o/w) empulsion process and dried in an agitated filter dryer under nitrogen flow.

Formulation, solvent and drying rate were varied for evaluation of nimodipine polymorph composition of the microparticles. Microparticle size was evaluated by laser diffraction. The particle size distribution for 63% nimodipine (wt %) and 1.3% water was 66 µm (mean), 95 µm (95$^{th}$ percentile) and 39 µm (10$^{th}$ percentile). The placebo microparticulate formulation containing a uniform size distribution of microparticles was prepared by combining a polymer solution (e.g., a 50-50 glycolide-lactide blend) with a solvent in the absence of nimodipine.

Formulation and processing parameters such as polymer selection, processing solvent, and drying rate were varied to evaluate the formation of drug polymorphs. In all cases, crystalline Form I of Nimodipine was used as the starting material in the production of the microparticles.

Figure 6:
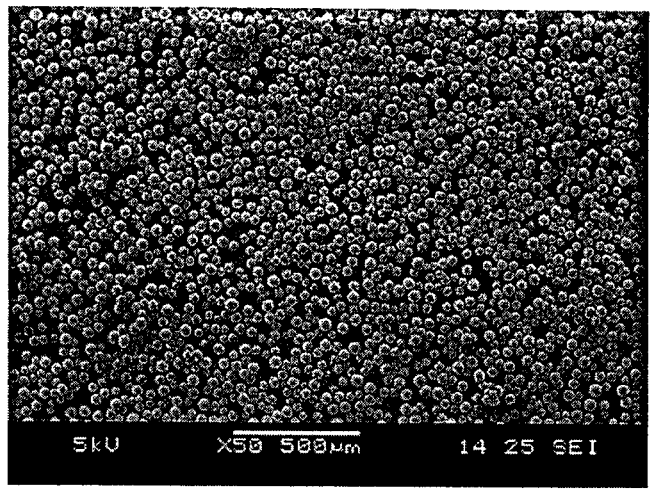
FIG. 6 shows scanning electron micrograph (SEM) image of a microparticulate nimodipine formulation according to the present invention.

Microparticle morphology was evaluated by Scanning Electron Microscopy (SEM). Scanning electron microscope imaging of nimodipine microsphere formulations were performed at 0° C., 25° C. and 30-35° C. FIG. 6 shows a scanning electron micrograph (SEM) image of a microparticulate nimodipine formulation according to the present invention.

The polymorph composition was characterized using X-ray powder diffraction, Raman spectroscopy, and Differential Scanning calorimetry.

Raman spectroscopy showed that the nimodipine microsphere formulations undergo phase transition and crystal formation upon change in storage temperature. For Raman imaging, cross-sections were prepared by mixing the nimodipine microspheres in epoxy and letting to harden. The hardened epoxy with embedded microspheres were then sliced with a microtome at −65° C. Full spectral images, 60×60 µm in size, 2 pixels (spectra) per µm, were taken over multiple microsphere cross sections per lot to determine the distribution of the drug within the microspheres. After data acquisition, an augmented classical least squares routine was implemented, which uses the entire reference spectra from the nimodipine drug, polymer and epoxy) to deconvolute the signals of each component. The resulting images showed the relative Raman intensity and spatial distribution of each component within the cross-sectional region examined.

Differential Scanning Calorimetry (DSC) showed the polymorph content of nimodipine microsphere formulations of the present invention. DSC is a thermoanalytical technique useful in detecting phase transitions in solid samples by measuring the amount of heat absorbed or released during such transitions. Characteristic DSC spectra indicating characteristic melting temperatures are used are signatures for identifying a specific polymorphic form of a sample.

Figure 11:
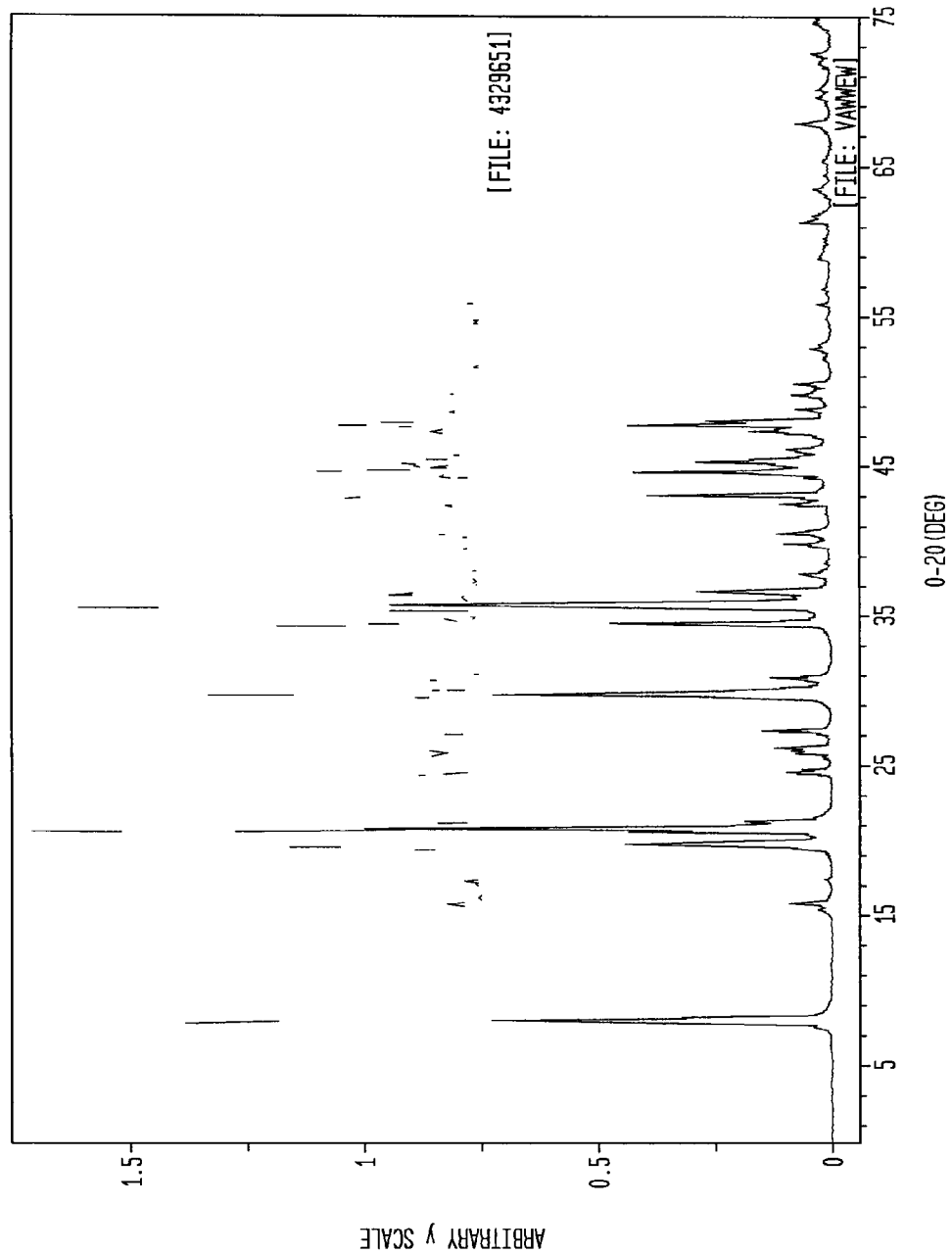
FIG. 11 shows an x-ray powder diffraction pattern of nimodipine form I.

X-ray powder diffraction shows the polymorph content of nimodipine microsphere formulations of the present invention. X-ray powder diffraction (XRPD) analysis was used to detect distinctive diffraction patterns characterizing a specific polymorphic form of a given sample. FIG. 11 shows an x-ray powder diffraction pattern of nimodipine form I.

Analysis revealed that up to three drug forms, in varying ratios, were present in the microparticle lots after processing: crystalline Form I, crystalline Form II, and amorphous nimodipine. Crystalline Form II and amorphous component caused aggregation of the resultant product, leading to poor product performance.

Polymer selection and solvent choice, and to a lesser extent, drying rate, were determined to be critical in producing stable microparticulate formulations containing the nimodipine Form I.

Example 3

In Vitro Release Kinetic Analysis

Figure 4:
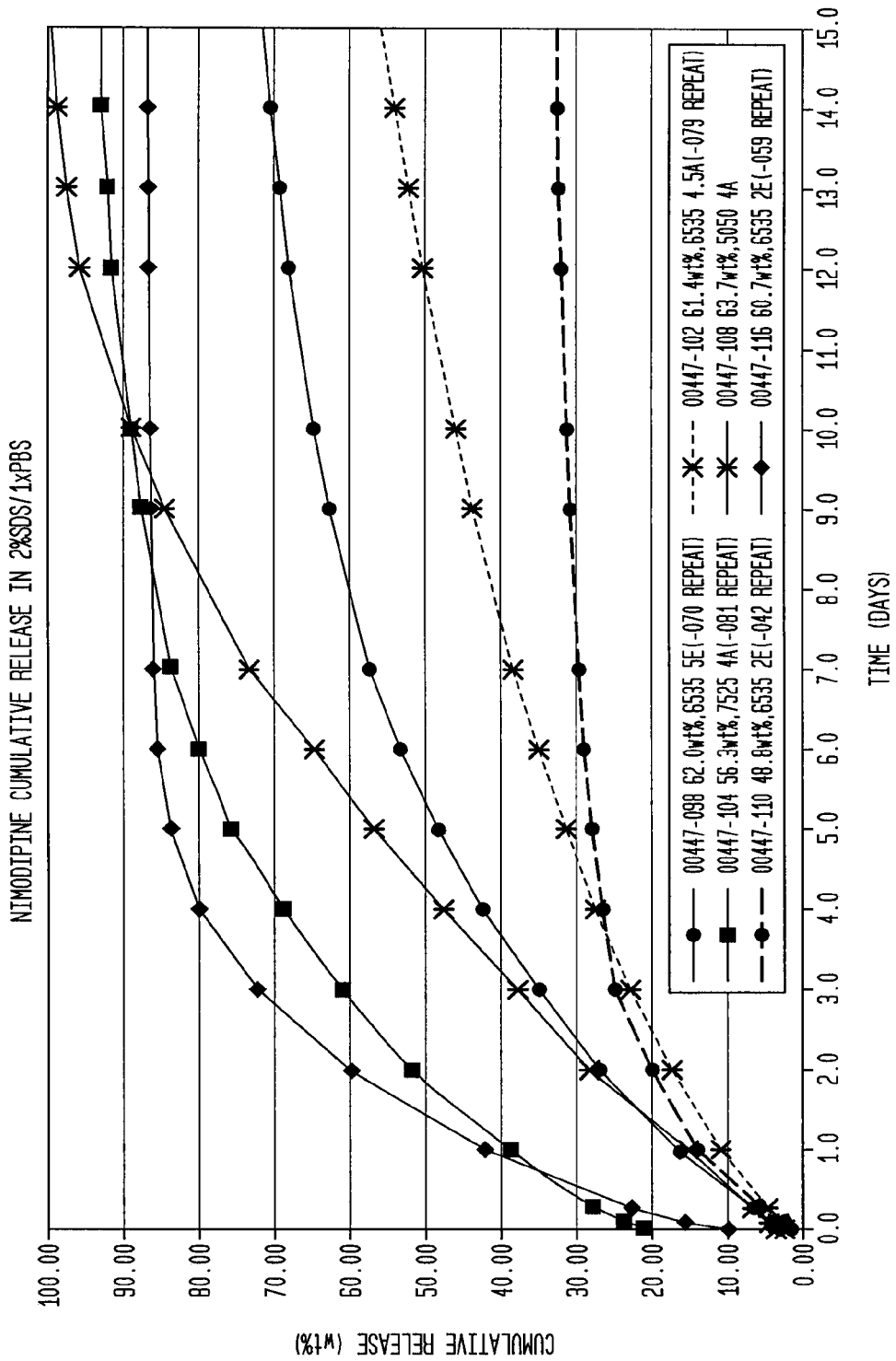
FIG. 4 shows the in vitro cumulative release of exemplary microparticulate nimodipine formulations expressed as weight % of the over time.

This example measures the percentage by weight of nimodipine drug released in vitro over time. 10 mg nimodipine microspheres were weighed into a 50 mL falcon tube and 20 mL freshly prepared solution of 2% sodium dodecyl sulfate in 1× phosphate buffered saline was added. Samples were inverted once to ensure microsphere suspension. The tubes were then incubated in a water bath at 37° C. and pulled at specific timepoints: 1 hr, 2 hrs, 6 hrs, 24 hrs and then each day till 14 days. The pulled samples were analyzed for nimodipine content by HPLC. FIG. 4 shows the in vitro cumulative release of exemplary microparticulate nimodipine formulations expressed as weight % of the over time.

Example 4

In Vivo Release

Figure 5:
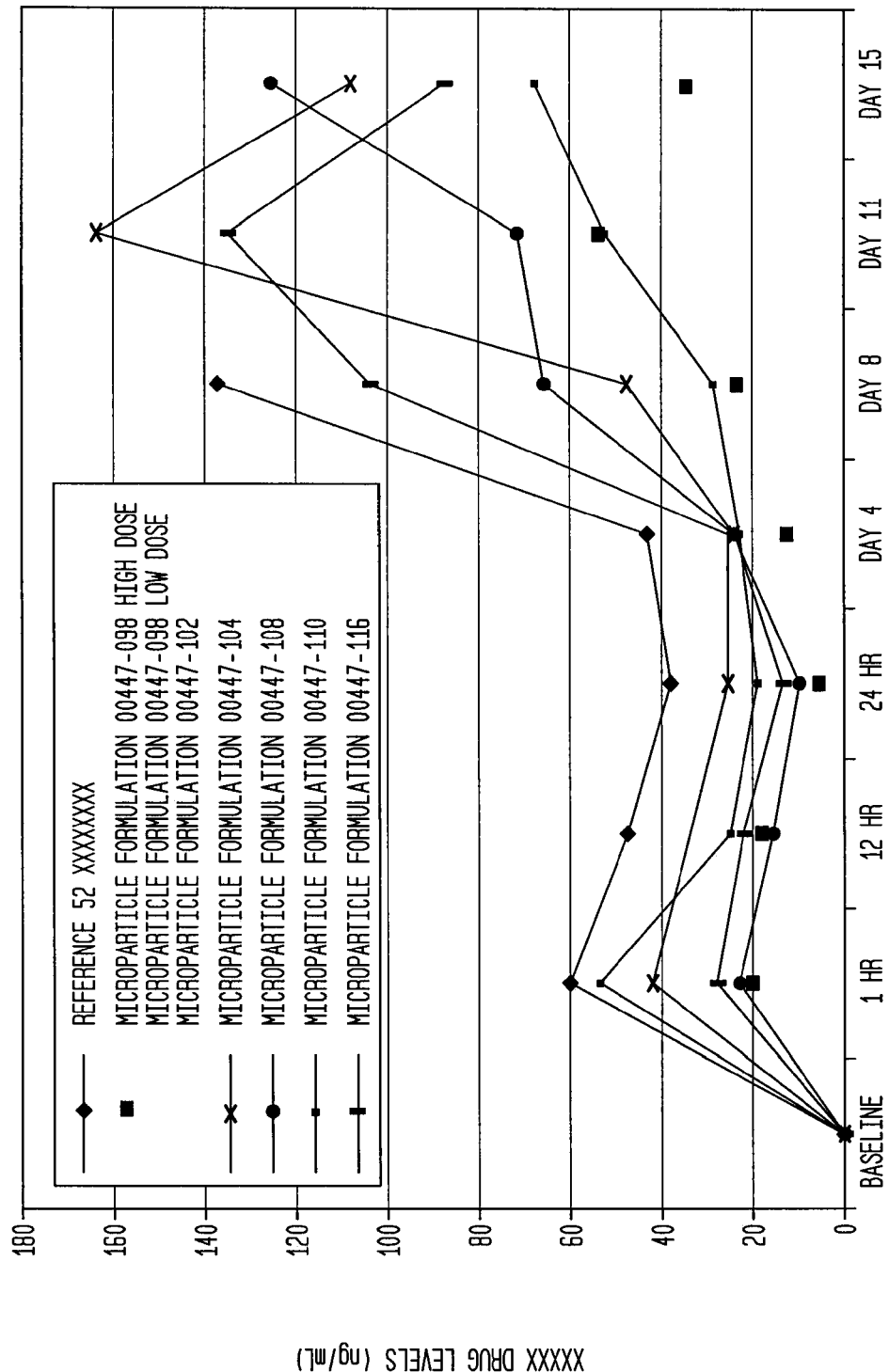
FIG. 5 shows rat plasma drug levels in ng/mL upon administration of nimodipine microsphere formulations.

This example shows that nimodipine plasma levels ranging between 40 ng/mL to about 160 ng/mL are achieved within 11 days of administration. In vivo release kinetic analysis was performed using a rat model. Blood plasma samples were drawn at indicated time points and plasma levels of nimodipine were analyzed. FIG. 5 shows rat plasma drug levels in ng/mL upon administration of nimodipine microsphere formulations.

Example 5

Analysis of Microparticle Formation

Nimodipine microparticles were prepared by an o/w emulsion process and dried in an agitated filter dryer under nitrogen flow. Formulation and processing parameters such as polymer selection, processing solvent, and drying rate were varied to evaluate the formation of drug polymorphs. In all cases, the crystalline Form I of Nimodipine was used as the starting material in the production of the microparticles. Microparticle morphology was evaluated by Scanning Electron Microscopy (SEM). Microparticle size was evaluated by laser diffraction. Drug polymorphs were characterized using various techniques including X-ray Powder Diffraction (XRPD), Raman Spectroscopy, and DSC.

Figure 12A:
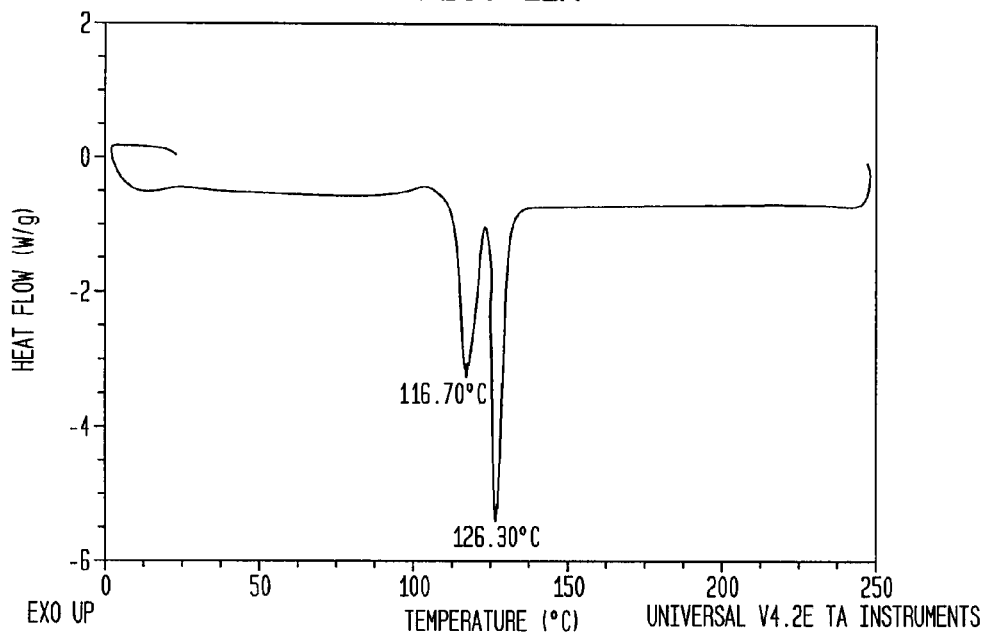
FIG. 12A shows nimopidine prepared in dichloromethane (DCM) showing the presence of polymorphic forms.
Figure 12B:
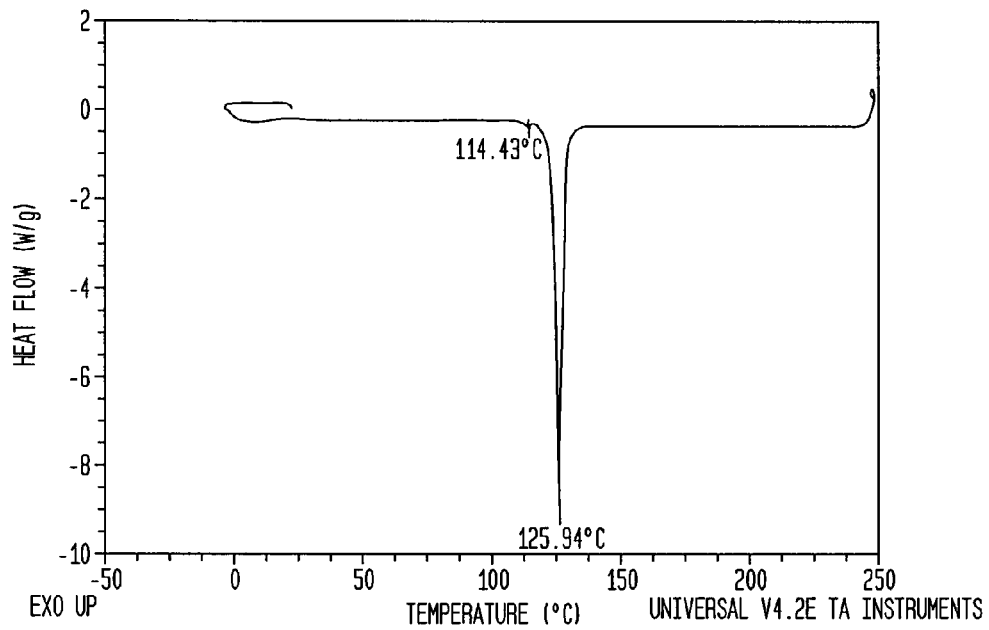
FIG. 12B shows large pure nimodipine prepared in ethyl acetate (EtOAc).
Figure 12C:
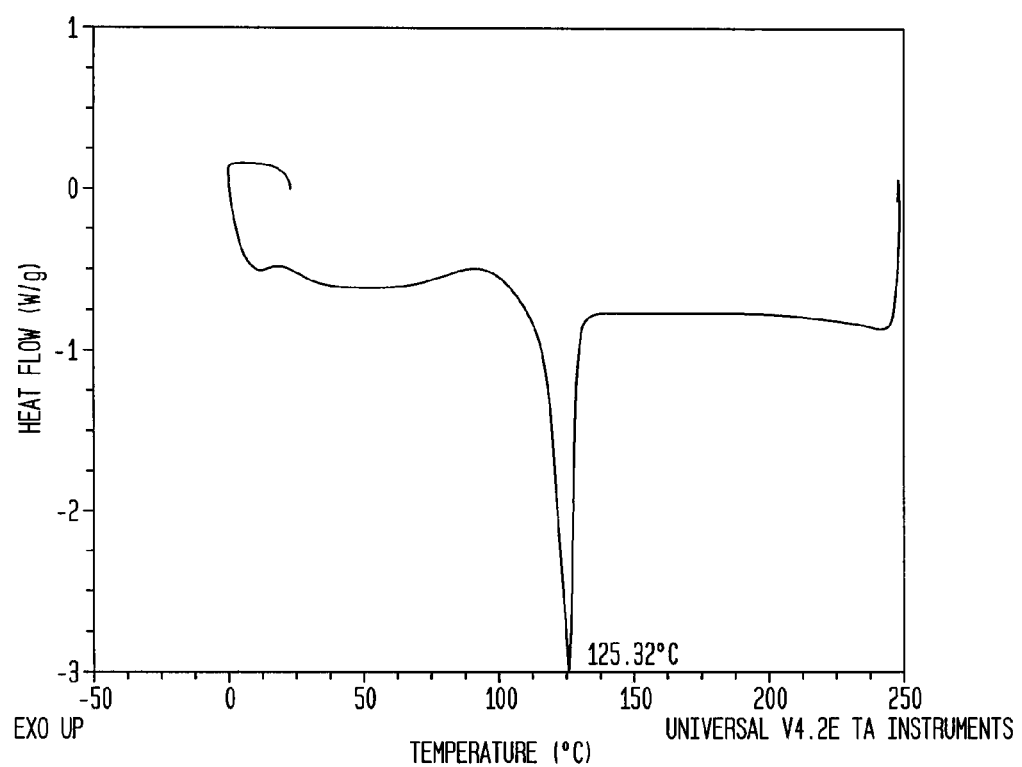
FIG. 12C shows that microencapsulation under the same parameters does not effect the purity of the nimodipine.

Analysis revealed that up to three drug forms, in varying ratios, were present in the microparticle lots after processing: crystalline Form I, crystalline Form II, and amorphous Nimodipine. Crystalline Form II and the amorphous component caused aggregation of the resultant product, leading to poor product performance. Spectra confirmed the presence of polymorphism, showing melting points of 116° C. and 126° C. (in a ratio of approximately 1:2) for Nimodipine prepared in DCM, FIG. 12A. Pre-Formulation for Nimodipine prepared in EtOAc, showed a slight melting point peak at 114° C. which corresponded to Modification II form of the active. It also had a main, sharp melting peak of 125° C., FIG. 12B. DSC of the pre-formulation active DLG encapsulated Nimodipine, prepared in EtOAc showed one melting point peak only at 125° C., FIG. 12C.

Nimodipine Lot 00447-098—This material showed the presence of Modification I only. This lot was produced using a single emulsion process with suspended drug in a ethyl acetate polymer solution. A 6535 DLG 5E polymer was used with 65% theoretical drug load. A 10 g batch was prepared where the dispersed phase consisted of a 20% polymer solution in ethyl acetate with drug added directly to the polymer solution to form a suspension. The continuous phase comprised a continuous process medium comprising a surfactant of 2% polyvinyl alcohol (PVA) solution saturated with 3% ethyl acetate. A FormEZE column packed with 500 μm beads was used to form the emulsion. The dispersed phase and continuous phase were added at a rate of 2 mL/min and 4 mL/min, respectively. The emulsified particles were extracted into water that was added at a rate of 300 mL/min. The particles were collected over 125 and 25 μm sieves and then dried by lyophilization.

Nimodipine Lot 00447-108—This material was amorphous. This lot was produced using a single emulsion process with suspended drug in an ethyl acetate polymer solution. A 5050 DLG 4A polymer was used with 65% theoretical drug load. A 10 g batch was prepared where the dispersed phase consisted of a 20% polymer solution in ethyl acetate with drug added directly to the polymer solution to form a suspension. The continuous phase comprised a continuous process medium comprising 2% polyvinyl alcohol solution saturated with 3% ethyl acetate. A FormEZE column packed with 500 μm beads was used to form the emulsion. The dispersed phase and continuous phase were added at a rate of 2 mL/min and 4 mL/min, respectively. The emulsified particles were extracted into water that was added at a rate of 300 mL/min. The particles were collected over 125 and 25 μm sieves and then dried by lyophilization.

Nimodipine Lot 00447-110—This material showed the presence of Modification I & II. This lot was produced using a single emulsion process with suspended drug in an ethyl acetate polymer solution. A 6535 DLG 2E polymer was used with 50% theoretical drug load. A 10 g batch was prepared where the dispersed phase consisted of a 20% polymer solution in ethyl acetate with drug added directly to the polymer solution to form a suspension. The continuous phase comprised a continuous process medium comprising 2% polyvinyl alcohol solution saturated with 3% ethyl acetate. A FormEZE column packed with 500 μm beads was used to form the emulsion. The dispersed phase and continuous phase were added at a rate of 2 mL/min and 4 mL/min, respectively. The emulsified particles were extracted into water that was added at a rate of 300 mL/min. The particles were collected over 125 and 25 μm sieves and then dried by lyophilization.

Nimodipine Lot ML695 (GMP material)—This lot showed the presence of Modification II. This lot was produced using a single emulsion process with suspended drug in an ethyl acetate polymer solution. A 5050 DLG 4A polymer was used with 65% theoretical drug load. Material was dried under nitrogen at a much slower rate than previous lots of the same formulation. This slowed drying caused the formation of the modification II polymorph where previous lots dried at a faster rate contained only amorphous drug. A 250 g batch was prepared where the dispersed phase consisted of a 20% polymer solution in ethyl acetate with drug added directly to the polymer solution to form a suspension. The continuous phase comprised a continuous process medium comprising 2% polyvinyl alcohol solution saturated with 3% ethyl acetate. A FormEZE column packed with 500 μm beads was used to form the emulsion. The dispersed phase and continuous phase were added at a rate of 20 mL/min and 40 mL/min, respectively. The emulsified particles were extracted into water that was added at a rate of 1500 mL/min. The particles were collected over 125 and 25 μm sieves and then dried under nitrogen flow.

EQUIVALENTS

While the described invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the described invention. All such modifications are intended to be within the scope of the claims appended hereto.

What is claimed is:

1. A process for producing microparticles encapsulating a crystalline polymorphic Form I of Nimodipine that has an X-ray Powder Diffraction (XRPD) spectrum substantially the same as the X-ray Powder Diffraction (XRPD) spectrum shown in FIG. 11, the process comprising:
    (a) providing the polymorphic Form I of Nimodipine;
    (b) adding the polymorphic Form I of Nimodipine to a polymer solution, thereby creating a mixture of the polymorphic Form I of Nimodipine and the polymer solution;
    (c) homogenizing the mixture to form a disperse phase;
    (d) mixing the disperse phase with a continuous phase comprising a continuous process medium, thereby forming an emulsion comprising the polymorphic Form I of Nimodipine;
    (e) forming and extracting the microparticles comprising the polymorphic Form I of Nimodipine; and
    (f) drying the microparticles,
    the microparticles being characterized by:
    (i) dispersal of the polymorphic Form I of Nimodipine throughout each microparticle; and
    (ii) at least 70 percent by weight relative to the total weight of Nimodipine of Form I of Nimodipine.

2. The process according to claim 1, wherein the polymer solution comprises a solvent and a biodegradable polymer.

3. The process according to claim 2, wherein the biodegradable polymer is selected from the group consisting of polylactide, polylactide-co-glycolide, poly(orthoester), and poly(anhydride).

4. The process according to claim 3, wherein the polylactide co-glycolide comprises a 85:15, 75:25, 65:35, or 50:50 mole ratio of lactide to glycolide.

5. The process according to any of claim 2 wherein the solvent in the polymer solution in (b) comprises ethyl acetate or dichloromethane or a mixture thereof.

6. The process according to claim 1 wherein time for drying in (f) is from 4 to 48 hours.

7. The process according to claim 1, wherein the continuous process medium comprises water, dichloromethane, ethanol or a combination thereof.

8. The process according to claim 1, further comprising a surfactant in the continuous process medium.

9. The process according to claim 8, wherein the surfactant is polyvinyl alcohol (PVA).

10. The process according to claim 1, further comprising rinsing the microparticles prior to drying.

11. The process according to claim 1, wherein rate of drying in (f) is between 0.2 mLs per minute and 2 liters per minute.

12. The process according to claim 1, wherein the process further comprises:
    (g) analyzing a morphology of the microparticles via X-ray powder diffraction (XRPD), Raman spectroscopy, Differential Scanning Calorimetry, or a combination thereof.

13. A semisolid, biodegradable, biocompatible delivery system capable of sustained release kinetics comprising
    (i) a flowable microparticulate formulation comprising a crystalline polymorphic Form I of Nimodipine, with an X-ray Powder Diffraction (XRPD) spectrum substantially the same as the X-ray Powder Diffraction (XRPD) spectrum shown in FIG. 11, the microparticulate formulation being characterized by:
    (a) a plurality of microparticles;
    (b) dispersal of the polymorphic Form I of Nimodipine throughout each microparticle;
    (c) at least 70 percent by weight relative to the total weight of Nimodipine of Form I of Nimodipine; and
    (ii) a pharmaceutically acceptable carrier,
    the delivery system being characterized by delayed release of the polymorphic Form I of Nimodipine from the delivery system, wherein one half of the polymorphic Form I of Nimodipine is released from the delivery system within 1 day to 30 days in vivo.

14. The delivery system according to claim 13, wherein each microparticle comprises a matrix.

15. The delivery system according to claim 13, wherein the microparticulate formulation comprises a powder suspension of microparticles.

16. The delivery system according to claim 13, wherein the microparticulate formulation further comprises a biodegradable polymer.

17. The delivery system according to claim 13, wherein Nimodipine load of the formulation contained within the delivery system ranges from about 25% to 75% by weight relative to the total weight of the formulation.

18. The delivery system according to claim 16, wherein the biodegradable polymer is selected from the group consisting of polylactide-polyglycolide, poly(orthoester), and poly(anhydride).

19. The semisolid, biodegradable, biocompatible delivery system capable of sustained release kinetics according to claim 13, wherein the microparticulate formulation is characterized by a Nimodipine load of from about 25% to 75% by weight relative to the total weight of the formulation and each microparticle comprises a matrix.

20. The semisolid, biodegradable, biocompatible delivery system capable of sustained release kinetics according to claim 19, wherein the flowable microparticulate formulation is prepared by a process comprising:
    (a) providing the polymorphic Form I of Nimodipine with an X-ray Powder Diffraction (XRPD) spectrum substantially the same as the X-ray Powder Diffraction (XRPD) spectrum shown in FIG. 11;
    (b) adding the polymorphic Form I of Nimodipine to a polymer solution, thereby creating a mixture of the polymorphic Form I of Nimodipine and the polymer solution;
    wherein the polymer solution comprises a solvent and a biodegradable polymer, the solvent in the polymer solution comprises ethyl acetate or dichloromethane or a mixture thereof and the biodegradable polymer is selected from the group consisting of polylactide, polylactide-co-glycolide, poly(orthoester), and poly(anhydride);
    (c) homogenizing the mixture to form a disperse phase;
    (d) mixing the disperse phase with a continuous phase comprising a continuous process medium, thereby forming an emulsion comprising the polymorphic Form I of Nimodipine;
    (e) forming and extracting the microparticles comprising the polymorphic Form I of Nimodipine; and
    (f) drying the microparticles for a time from 4 to 48 hours, wherein the microparticulate formulation is characterized by:
    (i) a plurality of microparticles;
    (ii) dispersal of the polymorphic Form I of Nimodipine throughout each microparticle;
    (iii) at least 70 percent by weight relative to the total weight of Nimodipine of Form I of Nimodipine.

21. A method for treating at least one cerebral artery in a subarachnoid space at risk of interruption due to a brain injury in a human subject, comprising:
 (a) providing a flowable sustained release microparticle composition comprising the semisolid, biodegradable, biocompatible delivery system according to claim 19, and
 (b) administering the flowable, sustained release microparticle composition locally, either
  (i) intraventricularly so that the microparticulate formation is carried by cerebrospinal fluid (CSF) flow from the cerebral ventricle to the subarachnoid space before releasing the nimodipine form I in the subarachnoid space,
  (ii) intracisternally into the subarachnoid space in a subarachnoid cistern closest to a cerebral artery at risk for interruption, or
  (iii) intrathecally into spinal subarachnoid space so the composition is carried by cerebrospinal fluid (CSF) flow from the spinal subarachnoid space to the subarachnoid space of the brain before releasing the Form I of Nimodipine in the subarachnoid space of the brain;
wherein interruption of the cerebral artery is accompanied by at least one delayed complication selected from the group consisting of an angiographic vasospasm, formation of a plurality of microthromboemboli, a cortical spreading ischemia, a delayed cerebral ischemia (DCI), or a combination thereof; and
wherein a therapeutic amount of the substantially pure crystalline Form I of Nimodipine having an X-ray Powder Diffraction (XRPD) spectrum substantially the same as the X-ray Powder Diffraction (XRPD) spectrum shown in FIG. 11 that contacts and flows around the at least one cerebral artery in the subarachnoid space is effective to treat the delayed complication without entering systemic circulation in an amount to cause hypotension.

* * * * *

UNITED STATES PATENT AND TRADEMARK OFFICE
CERTIFICATE OF CORRECTION

PATENT NO. : 8,821,944 B1
APPLICATION NO. : 13/943547
DATED : September 2, 2014
INVENTOR(S) : R. Loch Macdonald et al.

Page 1 of 1

It is certified that error appears in the above-identified patent and that said Letters Patent is hereby corrected as shown below:

In the Specification

Column 57, line 65 and column 58, lines 14, 31 and 51: add the symbol "®" after the term "FormEZE".

Signed and Sealed this
Sixteenth Day of December, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,821,944 B1 | Page 1 of 1 |
| APPLICATION NO. | : 13/943547 | |
| DATED | : September 2, 2014 | |
| INVENTOR(S) | : Macdonald et al. | |

It is certified that error appears in the above-identified patent and that said Letters Patent is hereby corrected as shown below:

Title page

Item (72) Inventors: Add "Parissa Heshmati"

Signed and Sealed this
Second Day of August, 2016

Michelle K. Lee
*Director of the United States Patent and Trademark Office*